US011982668B2

(12) United States Patent
King et al.

(10) Patent No.: US 11,982,668 B2
(45) Date of Patent: May 14, 2024

(54) USE OF ENGINEERED RENAL TISSUES IN ASSAYS

(71) Applicant: Organovo, Inc., San Diego, CA (US)

(72) Inventors: Shelby Marie King, San Diego, CA (US); Deborah Lynn Greene Nguyen, San Diego, CA (US); Sharon C. Presnell, San Diego, CA (US)

(73) Assignee: Organovo, Inc., San Diego, CA (US)

( * ) Notice: Subject to any disclaimer, the term of this patent is extended or adjusted under 35 U.S.C. 154(b) by 135 days.

(21) Appl. No.: 17/584,932

(22) Filed: Jan. 26, 2022

(65) Prior Publication Data

US 2022/0229045 A1 Jul. 21, 2022

Related U.S. Application Data

(62) Division of application No. 16/334,937, filed as application No. PCT/US2017/053997 on Sep. 28, 2017, now Pat. No. 11,268,950.

(60) Provisional application No. 62/400,894, filed on Sep. 28, 2016, provisional application No. 62/453,367, filed on Feb. 1, 2017.

(51) Int. Cl.
| | |
|---|---|
| C12N 5/00 | (2006.01) |
| C12N 5/071 | (2010.01) |
| G01N 33/50 | (2006.01) |
| G01N 33/573 | (2006.01) |

(52) U.S. Cl.
CPC ....... *G01N 33/5088* (2013.01); *C12N 5/0062* (2013.01); *C12N 5/0697* (2013.01); *G01N 33/573* (2013.01); *C12N 2503/04* (2013.01); *G01N 2800/347* (2013.01)

(58) Field of Classification Search
None
See application file for complete search history.

(56) References Cited

U.S. PATENT DOCUMENTS

| | | | |
|---|---|---|---|
| 6,417,185 B1 | 7/2002 | Goff et al. | |
| 6,477,783 B1 | 9/2002 | Yayon | |
| 6,489,344 B1 | 12/2002 | Nuss et al. | |
| 6,517,872 B1 | 2/2003 | Yayon et al. | |
| 7,005,252 B1 | 2/2006 | Thomson | |
| 7,037,918 B2 | 5/2006 | Nuss et al. | |
| 7,045,519 B2 | 5/2006 | Nuss et al. | |
| 7,326,570 B2 | 2/2008 | Nigam et al. | |
| 7,425,557 B2 | 9/2008 | Nuss et al. | |
| 7,439,064 B2 | 10/2008 | Thomson et al. | |
| 8,148,149 B2 | 4/2012 | Nigam et al. | |
| 8,263,403 B2 | 9/2012 | Perry et al. | |
| 8,278,105 B2 | 10/2012 | Pera et al. | |
| 8,431,395 B2 | 4/2013 | Ying et al. | |
| 8,518,700 B2 | 8/2013 | You et al. | |
| 8,546,140 B2 | 10/2013 | Mack et al. | |
| 8,569,061 B2 | 10/2013 | Nistor | |
| 8,597,947 B2 | 12/2013 | Reubinoff | |
| 8,906,677 B2 | 12/2014 | Li et al. | |
| 8,951,798 B2 | 2/2015 | Palecek et al. | |
| 8,962,322 B2 | 2/2015 | Shi et al. | |
| 9,074,180 B2 | 7/2015 | Smith et al. | |
| 9,080,145 B2 | 7/2015 | Nelson | |
| 9,149,952 B2 | 10/2015 | Murphy et al. | |
| 9,481,868 B2 | 11/2016 | Nguyen et al. | |
| 10,094,821 B2 | 10/2018 | Nguyen et al. | |
| 10,962,526 B2 | 3/2021 | Nguyen et al. | |
| 2006/0177925 A1 | 8/2006 | Rosenberg et al. | |
| 2008/0263683 A1 | 10/2008 | Miyata et al. | |
| 2010/0092432 A1 | 4/2010 | Ozaki et al. | |
| 2010/0317104 A1 | 12/2010 | Elefanty et al. | |
| 2012/0116568 A1 | 5/2012 | Murphy et al. | |
| 2012/0149110 A1 | 6/2012 | Kitamura et al. | |
| 2012/0207744 A1 | 8/2012 | Mendlein et al. | |

(Continued)

FOREIGN PATENT DOCUMENTS

| | | |
|---|---|---|
| CN | 103555660 A | 2/2014 |
| EP | 3 020 803 A1 | 5/2016 |

(Continued)

OTHER PUBLICATIONS

Desrochers et al. "Tissue-engineered kidney disease models." Advanced Drug Delivery Reviews 69 (2014): 67-80. (Year: 2014).*
Bülow et al. "Extracellular matrix in kidney fibrosis: more than just a scaffold." Journal of Histochemistry & Cytochemistry 67.9 (2019): 643-661. (Year: 2019).*
Astashkina, A.I., et al., "A 3-D Organoid Kidney Culture Model Engineered for High-throughput Nephrotoxicity Assays," Biomaterials 33(18):4700-4711, Elsevier Science, Netherlands (2012).
Baer, P.C., et al., "Effects of Mycophenolic Acid on Il-6 Expression of Human Renal Proximal and Distal Tubular Cells in Vitro," Nephrol Dial Transplant 19(1):47-52, Oxford University Press, England (2004).
Banu, N. and Meyers, C.M., "IFN-gamma And LPS Differentially Modulate Class II MHC and B7-1 Expression on Murine Renal Tubular Epithelial Cells," Kidney International 55(6):2250-63, Elsevier, United States (1999).

(Continued)

*Primary Examiner* — Emily A Cordas
(74) *Attorney, Agent, or Firm* — STERNE, KESSLER, GOLDSTEIN & FOX P.L.L.C.

(57) ABSTRACT

Disclosed are methods of assessing the ability of a candidate therapeutic agent to reverse, reduce or prevent renal injury by a potential toxic agent using a three-dimensional, engineered, bioprinted, biological renal tubule model. Also disclosed are methods of assessing the effect of an agent on renal function, the method comprising contacting the agent with a three-dimensional, engineered, bioprinted, biological renal tubule model. Also disclosed are models of renal disorder. In one embodiment, disclosed are models of renal fibrosis, comprising a three-dimensional, engineered, bioprinted, biological renal tubule model. Also disclosed are methods of making the model of renal disorder. In one embodiment disclosed are methods of making the model of renal fibrosis comprising contacting a three-dimensional, engineered, bioprinted, biological renal tubule model with an agent that is capable of inducing interstitial fibrotic tissue formation.

14 Claims, 21 Drawing Sheets

(56) References Cited

U.S. PATENT DOCUMENTS

| | | |
|---|---|---|
| 2012/0288938 A1 | 11/2012 | Forgacs et al. |
| 2013/0059325 A1 | 3/2013 | Dekel |
| 2013/0164339 A1 | 6/2013 | Murphy et al. |
| 2013/0190210 A1 | 7/2013 | Murphy et al. |
| 2014/0012407 A1 | 1/2014 | Murphy et al. |
| 2014/0363888 A1 | 12/2014 | Osafune et al. |
| 2015/0004273 A1 | 1/2015 | Forgacs et al. |
| 2015/0037445 A1 | 2/2015 | Murphy et al. |
| 2015/0037883 A1 | 2/2015 | Baharvand et al. |
| 2015/0057786 A1 | 2/2015 | Murphy et al. |
| 2015/0079675 A1 | 3/2015 | Li et al. |
| 2015/0087058 A1 | 3/2015 | Nam |
| 2015/0093932 A1 | 4/2015 | Ning et al. |
| 2015/0118748 A1 | 4/2015 | Ra et al. |
| 2016/0097039 A1 | 4/2016 | Nguyen et al. |
| 2016/0120938 A1 | 5/2016 | Jalan et al. |
| 2016/0237409 A1 | 8/2016 | Little et al. |
| 2018/0258404 A1 | 9/2018 | Boneventre, V et al. |
| 2019/0032020 A1 | 1/2019 | Takasato et al. |
| 2021/0208132 A1 | 7/2021 | Nguyen et al. |

FOREIGN PATENT DOCUMENTS

| | | |
|---|---|---|
| WO | WO 199809582 A1 | 3/1998 |
| WO | WO 03/046141 A2 | 6/2003 |
| WO | WO 2005/075636 A1 | 8/2005 |
| WO | WO 2012/011610 A1 | 1/2012 |
| WO | WO 2012/013969 A1 | 2/2012 |
| WO | WO 2012/168167 A1 | 12/2012 |
| WO | WO 2013/040087 A2 | 3/2013 |
| WO | WO 2013/067498 A1 | 5/2013 |
| WO | WO 2013/094771 A1 | 6/2013 |
| WO | WO 2014/197934 A1 | 12/2014 |
| WO | WO 2014/200115 A1 | 12/2014 |
| WO | WO 2015/069619 A1 | 5/2015 |
| WO | WO 2016/057571 A1 | 4/2016 |
| WO | WO 2016/094948 A1 | 6/2016 |
| WO | WO 2018/064323 A1 | 5/2018 |

OTHER PUBLICATIONS

Basile, D.P., et al., "Increased Transforming Growth Factor-beta 1 Expression in Regenerating Rat Renal Tubules Following Ischemic Injury," The American Journal of Physiology 270(3 Pt 2): F500-F509, American Physiological Society, United States (1996).

Boulpaep, E.L. and Seely, J.F., "Electrophysiology of Proximal and Distal Tubules in the Autoperfused Dog Kidney," The American Journal of physiology 221(4):1084-96, American Physiological Society, United States (1971).

Bryant, D.M. and Mostov, K.E., "From Cells to Organs: Building Polarized Tissue," Nature Reviews Molecular Cell Biology 9(11):887-901, Nature Pub. Group, England (2008).

Choudhury, D. and Ahmed, Z., "Drug-associated Renal Dysfunction and Injury," Nature Clinical Practice. Nephrology 2(2):80-91, Nature Pub. Group, England (2009).

Ciarimboli, G., et al., "Cisplatin Nephrotoxicity is Critically Mediated via the Human Organic Cation Transporter 2," The American Journal of Pathology 167(6):1477-84, Elsevier, United States (2005).

Ciarimboli, G., et al., "Organic Cation Transporter 2 Mediates Cisplatin-Induced Oto- and Nephrotoxicity and is a Target for Protective Interventions," The American Journal of Pathology 176(3):1169-80, Elsevier, United States (2010).

Clarke, L.L., "A Guide to Ussing Chamber Studies of Mouse Intestine," American Journal of Physiology. Gastrointestinal and Liver Physiology 296(6):G1151-66, American Physiological Society, United States (2009).

Farris, A.B. and Colvin, R.B., "Renal Interstitial Fibrosis: Mechanisms and Evaluation," Current Opinion in Nephrology and Hypertension 21(3):289-300, Lippincott Williams & Wilkins, England (2012).

Farris, A.B., et al., "Morphometric and Visual Evaluation of Fibrosis in Renal Biopsies," Journal of the American Society of Nephrology 22(1):176-86, American Society of Nephrology, United States (2011).

Ferrell, N., et al., "Albumin Handling by Renal Tubular Epithelial Cells in a Microfluidic Bioreactor," Biotechnology and Bioengineering 109(3):797-803, Wiley, United States (2012).

Gesualdo, L., et al., "Angiotensin IV Stimulates Plasminogen Activator Inhibitor-1 Expression in Proximal Tubular Epithelial Cells," Kidney International 56(2):461-70, Elsevier, United States (1999).

Godoy, P., et al., "Recent Advances in 2D And 3D in Vitro Systems Using Primary Hepatocytes, Alternative Hepatocyte Sources and Non-parenchymal Liver Cells and their use in Investigating Mechanisms of Hepatotoxicity, Cell Signaling and ADME," Archives of Toxicology 87(8):1315-530, Springer-Verlag, Germany (2013).

Granata, S., et al., "Mitochondria: A New Therapeutic Target in Chronic Kidney Disease," Nutrition and metabolism 12:49, BioMed Central, England (2015).

Griffith, L.G., et al., "Engineering Liver," Hepatology 60(4):1426-1434, Wiley, United States (2014).

Guinee, D.G. Jr., et al., "Clinically Silent Progressive Renal Tubulointerstitial Disease During Cisplatin Chemotherapy," Cancer 71(12):4050-4054, Wiley, United States (1993).

Hanigan, M.H. and Devarajan, P. "Cisplatin Nephrotoxicity: Molecular Mechanisms," Cancer Therapy 1:47-61, Gene Therapy Press, Greece (2003).

Ichihara, A., et al., "Renal Renin-angiotensin System," Contributions to Nephrology 143:117-30, Karger, Switzerland (2004).

Ishikura, H., et al., "Cytokine Regulation Of ICAM-1 Expression on Human Renal Tubular Epithelial Cells in Vitro," Transplantation 51(6):1272-1275, Lippincott Williams & Wilkins, United States (1991).

Jakab, K., et al., "Tissue Engineering by Self-assembly and Bio-printing of Living Cells," Bio Fabrication 2(2):022001, IOP Publishing, England (Jun. 2010).

Jakab, K., et al., "Tissue Engineering by Self-assembly of Cells Printed Into Topologically Defined Structures," Tissue Engineering Part A 14(3):413-421, Mary Ann Liebert, Inc, United States (Mar. 2008).

Jang, K-J., et al., "Human Kidney Proximal Tubule-on-a-chip for Drug Transport and Nephrotoxicity Assessment," Integrative Biology 5(9):1119-1129, RSC Publishing, England (2013).

Joraku, A., et al., "In Vitro Generation of Three-dimensional Renal Structures," Methods 47(2):129-133, Academic Press, United States (2009).

Kaissling, B. and Hir, M.L. "The Renal Cortical Interstitium: Morphological and Functional Aspects," Histochemistry and Cell Biology 130(2):247-262, Springer, Germany (2008).

Kamiie, J., et al., "Quantitative Atlas of Membrane Transporter Proteins: Development and Application of a Highly Sensitive Simultaneous LC/MS/MS Method Combined with Novel in-silico Peptide Selection Criteria," Pharmaceutical research 25(6):1469-1483, Kluwer Academic/Plenum Publishers, United States (2008).

Katsuda, H., et al., "Protecting Cisplatin-induced Nephrotoxicity with Cimetidine does not Affect Antitumor Activity," Biological & Pharmaceutical Bulletin 33(11):1867-71, Pharmaceutical Society of Japan, Japan (2010).

King, S.M., et al., "Early Transformative Changes in Normal Ovarian Surface Epithelium Induced by Oxidative Stress Require Akt Upregulation, DNA Damage and Epithelial-stromal Interaction," Carcinogenesis 34(5):1125-33, Irl Press At Oxford University Press, England (2013).

Kleinknecht, D., et al., "Drug-associated Acute Renal Failure. A Prospective Collaborative Study of 81 Biopsied Patients," Advances in Experimental Medicine and Biology 212:125-8, Kluwer Academic/Plenum Publishers, United States (1987).

Kobori, H., et al., "The Intrarenal Renin-angiotensin System: from Physiology to the Pathobiology of Hypertension and Kidney Disease," Pharmacological Reviews 59(3):251-87, American Society for Pharmacology and Experimental Therapeutics, United States (2007).

(56) References Cited

OTHER PUBLICATIONS

Kumar, S., "Measurement of Caspase Activity in Cells Undergoing Apoptosis," Methods in Molecular Biology 282:19-30, Humana Press, United States (2004).
Kunz-Schughart, L.A., et al., "Potential of Fibroblasts to Regulate the Formation of Three-dimensional Vessel-like Structures from Endothelial Cells in Vitro," American Journal of Physiology Cell Physiology 290(5):C1385-98, American Physiological Society, United States (2006).
Lemley, K. V. and Kriz, W., "Anatomy of the Renal Interstitium," Kidney International 39(3):370-81, Elsevier, United States (1991).
Li, D., et al., "Complement Factor B Production in Renal Tubular Cells and its Role in Sodium Transporter Expression During Polymicrobial Sepsis," Critical Care Medicine 44(5):e289-99, Kolen, United States (2016).
Li, W., et al., "Developmental Origins and Functions of Stromal Cells in the Normal and Diseased Mammalian Kidney," Developmental Dynamics 243(7):853-63, Wiley, United States (2014).
Liang, M., et al., "The Paracellular Permeability of Opossum Kidney Cells, a Proximal Tubule Cell Line," Kidney International 56(6):2304-8, Elsevier, United States (1999).
Lin, Z. and Will, Y., "Evaluation of Drugs With Specific Organ Toxicities in Organ-specific Cell Lines," Toxicological Sciences 126(1):114-127, Oxford University Press, United States (Mar. 2012).
Loghman-Adham, M., et al., "Detection and Management of Nephrotoxicity During Drug Development," Expert Opinion on Drug Safety 11(4):581-596, Taylor & Francis, England (Jul. 2012).
Lohr, J.W., et al., "Renal Drug Metabolism," Pharmacological Reviews 50(1):107-141, American Society for Pharmacology and Experimental Therapeutics, United States (Mar. 1998).
Melenhorst W.B.W.H., et al., "Epidermal Growth Factor Receptor Signaling in the Kidney: Key Roles in Physiology and Disease, " Hypertension 52(6):987-993, Lippincott, Williams & Wilkins, United States (Dec. 2008).
Meran, S. and Steadman, R., "Fibroblasts and Myofibroblasts in Renal Fibrosis," International Journal of Experimental Pathology 92(3):158-167, Wiley, England (Jun. 2011).
Moll, S., et al., "Epithelial Cells as Active Player in Fibrosis: Findings From an in Vitro Model," PloS one 8(2):e56575, Public Library of Science, United States (2013).
Mulay, S.R., et al., "Molecular Mechanisms of Crystal-related Kidney Inflammation and Injury. Implications for Cholesterol Embolism, Crystalline Nephropathies and Kidney Stone Disease," Nephrology, Dialysis, Transplantation 29(3):507-514, Oxford University Press, England (Mar. 2014).
Nadasdy, T., et al., "Proliferative Activity of Intrinsic Cell Populations in the Normal Human Kidney," Journal of the American Society of Nephrology 4(12):2032-2039, American Society of Nephrology, United States (Jun. 1994).
Nagle, M.A., et al., "Analysis of Three-dimensional Systems for Developing and Mature Kidneys Clarifies the Role of OAT1 and OAT3 in Antiviral Handling," The Journal of Biological Chemistry 286(1):243-251, American Society for Biochemistry and Molecular Biology, United States (Jan. 2011).
Norotte, C., et al., "Scaffold-free Vascular Tissue Engineering Using Bioprinting," Biomaterials 30(30):5910-5917, Elsevier Science, Netherlands (Oct. 2009).
Okada, H., et al., "Connective Tissue Growth Factor Expressed in Tubular Epithelium Plays a Pivotal Role in Renal Fibrogenesis," Journal of the American Society of Nephrology 16(1):133-143, American Society of Nephrology, United States (Jan. 2005).
Okada, H., et al., "Dexamethasone Induces Connective Tissue Growth Factor Expression in Renal Tubular Epithelial Cells in a Mouse Strain-specific Manner," The American Journal of Pathology 168(3):737-747, Elsevier, United States (Mar. 2006).
Ozbolat, I.T. and Hospodiuk, M., "Current Advances and Future Perspectives in Extrusion-based Bioprinting," Biomaterials 76:321-343, Elsevier Science, Netherlands (Jan. 2016).

Paulsson, M., "Basement Membrane Proteins: Structure, Assembly, and Cellular Interactions," Critical Reviews in Biochemistry and Molecular Biology 27(1-2):93-127, Informa Healthcare, England (1992).
Prasad, B. and Unadkat, J.D., "Optimized Approaches for Quantification of Drug Transporters in Tissues and Cells by MRM Proteomics ," The AAPS Journal 16(4):634-648, American Association of Pharmaceutical Scientists, United States (Jul. 2014).
Rahman, M., et al., "Acute Kidney Injury: A Guide to Diagnosis and Management," American Family Physician 86(7):631-639, American Academy of General Practice, United States (Oct. 2012).
Rampersad, S.N., "Multiple Applications of Alamar Blue as an Indicator of Metabolic Function and Cellular Health in Cell Viability Bioassays," Sensors 12(9):12347-12360, Basel, Switzerland (2012).
Redfern, W.S., et al., "Impact and Frequency of Different Toxicities Throughout the Pharmaceutical Life Cycle," Toxicologist 114(S1), (Jan. 2010).
Schulz, W.W., et al., "Ultrastructural Localization of Angiotensin I-converting Enzyme (EC 3.4.15.1) and Neutral Metalloendopeptidase (EC 3.4.24.11) in the Proximal Tubule of the Human Kidney," Laboratory Investigation 59(6):789-797, Nature Pub. Group, United States (Dec. 1988).
Sonomura, K., et al., "The Kinase Pyk2 Is Involved in Renal Fibrosis by Means of Mechanical Stretch-induced Growth Factor Expression in Renal Tubules," Kidney International 81(5):449-457, Elsevier, United States (Mar. 2012).
Stokman, G., et al., "Stem Cell Factor Expression After Renal Ischemia Promotes Tubular Epithelial Survival," PLoS One 5(12):e14386, Public Library of Science, United States (Dec. 2010).
Subramanian, B., et al., "Tissue-engineered Three-dimensional in Vitro Models for Normal and Diseased Kidney," Tissue Engineering 16(9):2821-2831, Mary Ann Liebert, Inc., United States (Sep. 2010).
Tang, J. and Zhuang, S., "Epigenetics in Acute Kidney Injury," Current Opinion in Nephrology and Hypertension 24(4):351-358, Lippincott Williams & Wilkins, England (Jul. 2015).
Taniyama, Y., et al., "Renal Tubule-specific Transcription and Chromosomal Localization of Rat Thiazide-sensitive Na-Cl Cotransporter Gene," The Journal of Biological Chemistry 276(28):26260-26268, American Society for Biochemistry and Molecular Biology, United States (Jul. 2001).
Tasnim, F. and Zink, D., "Cross Talk Between Primary Human Renal Tubular Cells and Endothelial Cells in Cocultures," American Journal of Physiology Renal Physiology 302(8):F1055-F1062, American Physiological Society, United States (Apr. 2012).
Tay, L.K., et al., "Effects of cis-diamminedichloroplatinum(II) on Rabbit Kidney in Vivo and on Rabbit Renal Proximal Tubule Cells in Culture," Cancer Research 48(9):2538-2543, American Association for Cancer Research, United States (May 1988).
Tran, T.T., et al., "Exact Kinetic Analysis of Passive Transport Across a Polarized Confluent MDCK Cell Monolayer Modeled as a Single Barrier," Journal of pharmaceutical sciences 93(8):2108-23, Elsevier, United States (2004).
Tsuboi, N., et al., "Roles of Toll-like Receptors in C—C Chemokine Production by Renal Tubular Epithelial Cells," Journal of Immunology 169(4):2026-2033, American Association of Immunologists, United States (Aug. 2002).
Ussing, H.H., et al., "Transport Pathways in Biological Membranes," Annual Review of Physiology 36:17-49, Annual Reviews, United States (1974).
Vaidya, V.S., et al. ,"Biomarkers of Acute Kidney Injury," Annual Review of Pharmacology and Toxicology 48:463-493, Annual Reviews, United States (2008).
Vesey, D.A., et al., "Isolation and Primary Culture of Human Proximal Tubule Cells," Methods in Molecular Biology 466:19-24, Humana Press, United States (2009).
Wang, W.M., et al., "PPAR-gamma Agonists Inhibit Tgf-beta1-induced Chemokine Expression in Human Tubular Epithelial Cells," Acta Pharmacologica Sinica 30(1):107-112, Nature Publishing Group, United States (Jan. 2009).

(56) References Cited

OTHER PUBLICATIONS

Weng, Z., et al., "The Novel Flavone Tetramethoxyluteolin Is a Potent Inhibitor of Human Mast Cells," The Journal of Allergy and Clinical Immunology 135(4):1044-1052, Mosby, United States (Apr. 2015).
Wieser, M., et al., "hTERT Alone Immortalizes Epithelial Cells of Renal Proximal Tubules Without Changing Their Functional Characteristics," American Journal of Physiology 295(5):F1365-F1375, American Physiological Society, United States (Nov. 2008).
Yonezawa, A., et al., "Association Between Tubular Toxicity of Cisplatin and Expression of Organic Cation Transporter rOCT2 (Slc22a2) in the Rat," Biochemical Pharmacology 70(12):1823-1831, Elsevier Science, England (Dec. 2005).
Zeisberg, M. and Kalluri, R., "Physiology of the Renal Interstitium," Clinical Journal of the American Society of Nephrology 10(10):1831-1840, American Society of Nephrology, United States (Oct. 2015).
Zhang, J. and Zhou, W., "Ameliorative Effects of SLC22A2 Gene Polymorphism 808 G/T and Cimetidine on Cisplatin-induced Nephrotoxicity in Chinese Cancer Patients," Food and Chemical Toxicology 50(7):2289-2293, Elsevier Science Ltd, England (Jul. 2012).
Zoja, C., et al., "Proteinuria and Phenotypic Change of Proximal Tubular Cells," Journal of the American Society of Nephrology 14(Suppl 1):S36-S41, American Society of Nephrology, United States (Jun. 2003).
Barak, H., et al., "FGF9 and FGF20 maintain the stemness of nephron progenitors in mice and man," *Dev. Cell* 22:1191-1207, Elsevier Inc., United States (2012).
Batchelder, C.A., et al., "Renal ontogeny in the rhesus monkey (*Macaca mulatta*) and directed differentiation of human embryonic stem cells toward kidney precursors," *Differentiation* 78:45-56, Elsevier Ltd., England (2009).
Beattie, G.M., et al., "Activin A Maintains Pluripotency of Human Embryonic Stem Cells in the Absence of Feeder Layers," *Stem Cells* 23:489-495, AlphaMed Press, United States (2005).
Blank, U., et al., "BMP7 promotes proliferation of nephron progenitor cells via a JNK-dependent mechanism," *Development*, 136(21):3557-3566, The Company of Biologists. United Kingdom (2009).
Bruce, S.J., et al., "In vitro differentiation of murine embryonic stem cells toward a renal lineage," *Differentiation* 75:337-349, International Society of Differentiation, United States (2007).
Colvin, J.S. et al., "Genomic Organization and Embryonic Expression of the Mouse Fibroblast Growth Factor 9 Gene," *Developmental Dynamics*, 216:72-88, Wiley-Liss, Inc., United States (1999).
D'Amour, K.A., et al., "Efficient differentiation of human embryonic stem cells to definitive endoderm," *Nature Biotechnology*, 23(12):1534-1541, Nature Publishing Group, United Kingdom (2005).
Fakhry, A., et al., "Effects of FGF-2/-9 in calvarial bone cell cultures: differentiation stage-dependent mitogenic effect, inverse regulation of BMP-2 and noggin, and enhancement of osteogenic potential," *Bone* 36:254-266, Elsevier Inc., United States (2005).
James, R.G., et al.. , "Bmp signaling promotes intermediate mesoderm gene expression in a dose-dependent, cell-autonomous and translation-dependent manner," Developmental Biology, 288:113-125, Elsevier, Netherlands (2005).
Little, M.H., et al., "Generating a self-organizing kidney from pluripotent cells," *Current Opinion in Organ Transplantation* 20(2):178-186, Wolters Kluwer Health, Inc., The Netherlands (2015).
Little, M.H., et al., "Understanding kidney morphogenesis to guide renal tissue regeneration," Nature Reviews Nephrology 12:624-635, Macmillan Publishers Limited, England (2016).
Metsuyanim, S., et al., "Expression of Stem Cell Markers in the Human Fetal Kidney," *PLoS One* 4(8):e6709, 15 pages, Public Library of Science, United States (2009).
Miyamoto, M., et al., "Molecular Cloning of a Novel Cytokine cDNA Encoding the Ninth Member of the Fibroblast Growth Factor Family, Which Has a Unique Secretion Property," *Molecular and Cellular Biology* 13(7):4251-4259, American Society for Microbiology, United States (1993).

Morizane, R., et al., "Differentiation of murine embryonic stem and induced pluripotent stem cells to renal lineage in vitro" *Biochemical and Biophysical Research Communications* 390:1334-1339, Elsevier Inc., United States (2009).
Ng, E.S., et al., "A protocol describing the use of a recombinant protein-based, animal product-free medium (APEL) for human embryonic stem cell differentiation as spin embryoid bodies," *Nature Protocols* 3(5):768-776, Nature Publishing Group, England (2008).
Ornitz, D.M., et al., "Ligand Specificity and Heparin Dependence of Fibroblast Growth Factor Receptors 1 and 3," *The Journal of Biological Chemistry* 267(23): 16305-16311, The American Society for Biochemistry and Molecular Biology, Inc., United States (1992).
Osafune, K., "Kidney regeneration and disease modeling research using iPS cell technology," Nihon Shoni Jinzobyo Gakkai Zasshi 26(1):64-69, The Japanese Society for Pediatric Nephrology, Japan (2013).
Schuldiner, M., et al., "Effects of eight growth factors on the differentiation of cells derived from human embryonic stem cells," *Proceedings of the National Academy of Sciences* 97(21):11307-11312, National Academy of Sciences, United States (2000).
Shoufu, T., et al., "Experimental Study on Differentiation of Embryonic Stem Cell into Renal Progenitor Cells with Cell Growth Factors," Chinese Journal of Integrated Traditional and Western Nephrology 13(12):1058-1063 (2012).
Taguchi, A., et al., "Redefining the In Vivo Origin of Metanephric Nephron Progenitors Enables Generation of Complex Kidney Structures from Pluripotent Stem Cells," *Cell Stem Cell* 14:53-67, Elsevier Inc., United States (2014).
Takasato, M., et al., "Directing human embryonic stem cell differentiation towards a renal lineage generates a self-organizing kidney," *Nature Cell Biology* 16(1):118-127, Macmillan Publishers Limited, England (2014).
Takasato, M., et al., "The origin of the mammalian kidney: implications for recreating the kidney in vitro," *Development* 142:1937-1947, The Company of Biologists Ltd., United States (2015).
Takasato, M., et al., "Generating kidney organoids from human pluripotent stem cells," Nature Protocols 11(9):1681-1692, Nature Publishing Group, England (2016).
Toyohara, T., et al., "Development of Differentiation Methods From Human IPSCS/ESCS Into Nephron Progenitor Cells," International Society for Stem Cell Research, Abstract No. F-2184, Poster Abstracts, 11th Annual Meeting, Jun. 12-15, Boston, MA (2013).
Trueb, B., et al., "Role of FGFRL1 and other FGF signaling proteins in early kidney development," *Cell. Mol. Life Sci.* 70:2505-2518, Springer Basel, Switzerland (2013).
Unverified Machine Translation of Chinese Patent Publication No. CN 103555660 A, Chinese Patent Office, 10 pages (listed as document FP4 on accompanying form PTO/SB/08A).
Yasuo, H. and Hudson, C.,"FGF8/17/18 functions together with FGF9/16/20 during formation of the notochord in *Ciona embryos,*" *Developmental Biology,* 302:92-103, Elsevier, Netherlands (2008).
Zhang, P., et al., "Short-term BMP-4 treatment initiates mesoderm induction in human embryonic stem cells," *Blood* 111(4):1933-1941, The American Society of Hematology, United States (2008).
Abu-Abed, S., et al., "The retinoic acid-metabolizing enzyme, CYP26A1, is essential for normal hindbrain patterning, vertebral identity, and development of posterior structures," Genes & Development 15:226-240, Cold Spring Harbor Laboratory Press, United States (2001).
Briggs, J.A., et al., "Integration-Free Induced Pluripotent Stem Cells Model Genetic and Neural Developmental Features of Down Syndrome Etiology," Stem Cells 31:467-478, Wiley Online Library, United States (2013).
Brown, A. C., et al., "Role for compartmentalization in nephron progenitor differentiation," PNAS, 110(12):4640-4645, United States National Academy of Science, United States (2013).
Brunskill, E.W., et al., "Atlas of Gene Expression in the Developing Kidney at Microanatomic Resolution," Developmental Cell 15:781-791, Elsevier Inc., Netherlands (2008).
Brunskill, E.W., et al., "Defining the Molecular Character of the Developing and Adult Kidney Podocyte," PLoS ONE 6(9):e24640, Public Library of Science, United States (2011).

(56) References Cited

OTHER PUBLICATIONS

Cebrian, C., et al., "The Number of Fetal Nephron Progenitor Cells Limits Ureteric Branching and Adult Nephron Endowment," Cell Reports, 7:127-137, Cell Press, United States (2014).

Cheng, X., et al., "Tissue Distribution, Ontogeny, and Hormonal Regulation of Xenobiotic Transporters in Mouse Kidneys," Drug Metabolism and Disposition 37(11):2178-2185, The American Society for Pharmacology and Experimental Therapeutics, United States (2009).

Cummings, S., et al., "Cisplatin-Induced Renal Cell Apoptosis: Caspase 3-Dependent and -Independent Pathways," The Journal of Pharmacology and Experimental Therapeutics 302(1):8-17, The American Society for Pharmacology and Experimental Therapeutics, United States (2002).

Dobin, A., et al., "STAR: ultrafast universal RNA-seq aligner," Bioinformatics 29(1):15-21, Oxford University Press, United Kingdom (2013).

Duester, G., "Retinoic Acid Synthesis and Signaling During Early Organogenesis," Cell 134(6):921-931, Cell Press, United States (2008).

Floege, J., et al., "Localization of PDGF α- receptor in the developing and mature human kidney," Kidney International 51:1140-1150, International Society of Nephrology, United States (1997).

James, R. G., and Schultheiss, T. M., "Patterning of the Avian Intermediate Mesoderm by Lateral Plate and Axial Tissues," Dev. Biol 253: 109-124, Elsevier, Netherlands (2003).

Kang, M., and Han, Y.- M., "Differentiation of human pluripotent stem cells into nephron progenitor cells in a serum and feeder free system," *PLoS One* 9: e94888, Public Library of Science, United States (2014).

Kobayashi, A., et al., "Identification of a Multipotent Self-Renewing Stromal Progenitor Population during Mammalian Kidney Organogenesis," *Stem Cell Reports* 3:650-662, Cell Press, United States (2014).

Lam, A.Q., et al., "Rapid and Efficient Differentiation of Human Pluripotent Stem Cells into Intermediate Mesoderm that Forms Tubules Expressing Kidney Proximal Tubular Markers," J. Am. Soc. Nephrol. 25:1211-1225, American Society of Nephrology (2014).

Loughna, S., et al., "Effects of oxygen on vascular patterning in Tie1/LacZ Metanephric kidneys in vitro," *Biochem. Biophys. Res. Commun.* 247: 361-366, Elsevier, Netherlands (1998).

Love, M., et al., "Moderated estimation of fold change and dispersion for RNA-seq data with DESeq2," *Genome Biol* 15: 550, BioMed Central, United Kingdom (2014).

Mae, S., et al., "Monitoring and robust induction of nephrogenic intermediate mesoderm from human pluripotent stem cells," *Nat. Commun.* 4: 1367, Nature Publishing Group, United States (2013).

Mese, H., et al., "The role of caspase family protease, caspase-3 on cisplatin-induced apoptosis in cisplatin30 resistant A431 cell line," *Cancer Chemother. Pharmacol.* 46: 241-245, Springer-Verlag, Germany (2000).

Mugford, J. W., et al., "Osr1 expression demarcates a multi-potent population of intermediate mesoderm that undergoes progressive restriction to an Osr1-dependent nephron progenitor compartment within the mammalian kidney," *Dev. Biol.* 324:88-98, Elsevier, Netherlands (2008).

Murphy, S.V. and Atala, A., "3D bioprinting of tissues and organs," Nat. Biotechnol. 32:773-785, Nature America, Inc. (2014).

Naujok, O., et al., "The Generation of Definitive Endoderm from Human Embryonic Stem Cells is Initially Independent from Activin A but Requires Canonical Wnt-Signaling," Stem Cell Rev. and Rep. 10:480-493, Springer, New York (2014).

Orlova, V.V., et al., "Generation, expansion and functional analysis of endothelial cells and pericytes derived from human pluripotent stem cells," *Nat Protoc.* 9(6):1514-1531, Nature Publishing Groups, United States (2014).

Park, J., et al., "Six2 and Wnt regulate self-renewal and commitment of nephron progenitors through shared gene regulatory networks," *Dev. Cell* 23: 637-651, Elsevier Inc., Netherlands (2012).

Roost, M.S., et al., "KeyGenes, a Tool to Probe Tissue Differentiation Using a Human Fetal Transcriptional Atlas," *Stem Cell Reports* 4: 1112-1124, Cell Press, United States (2015).

Sakai, Y., et al., "The retinoic acid-inactivating enzyme CYP26 is essential for establishing an uneven distribution of retinoic acid along the anterior-posterior axis within the mouse embryo." Genes & Development 15:213-225, Cold Spring Harbor Laboratory Press, United States (2001).

Short, K.M., et al., "Global quantification of tissue dynamics in the developing mouse kidney," Dev. Cell 29:188-202, Elsevier Inc., Netherlands (2014).

Sims-Lucas, S., et al., "Endothelial Progenitors Exist within the Kidney and Lung Mesenchyme," PLoS One 8(6):e65993, Public Library of Science, United States (2013).

Sweetman, D., et al., "The migration of paraxial and lateral plate mesoderm cells emerging from the late primitive streak is controlled by different Wnt signals," BMC Dev. Biol. 8: 63, Biomed Central, United Kingdom (2008).

Takasato, M., et al., "Kidney organoids from human iPS cells contain multiple lineages and model human nephrogenesis," Nature 526:564-568, Macmillan Publishers Limited, United Kingdom (2015).

Thiagarajan, R.D., et al., "Identification of anchor genes during kidney development defines ontological relationships, molecular subcompartments and regulatory pathways," PLoS One 6(2):e17286, Public Library of Science, United States (2011).

Xia, Y., et al., "Directed differentiation of human pluripotent cells to ureteric bud kidney progenitor-like cells," Nat. Cell Biol. 15:1507-1515, Nature Publishing Group, United States (2013).

Xinaris, C., et al., "In Vivo Maturation of Functional Renal Organoids Formed from Embryonic Cell Suspensions," J. Am. Soc. Nephrol. 23:1857-1868, American Society of Nephrology (2012).

Xu, J., et al., "Eya1 interacts with Six2 and Myc to regulate expansion of the nephron progenitor pool during nephrogenesis," Dev. Cell 31: 434-447, Elsevier Inc., Netherlands (2014).

Abrahamson, D.R., et al., "Development of kidney tubular basement membranes," Kidney International, 39(1991), pp. 382-393 (1991).

Co-pending U.S. Appl. No. 17/212,480, inventors Lynn, D., et al., filed Mar. 25, 2021 (Not Published).

Corning: Transwell permeable supports selection and use guide. Jun. 2013. Downloaded from http://csmedia2.corning.com/LifeSciences/Media/pdf/transwell_guide.pdf. On Feb. 4, 2016, p. 1-12.

Desrochers, T.M., et al., "Bioengineered 3D Human Kidney Tissue, a Platform for the Determination of Nephrotoxicity," PLoS ONE, 8(3): e59219, pp. 1-12, (2013).

International Search Report and Written Opinion for International Application No. PCT/US2017/053997, U.S. Patent and Trademark Office, Alexandria, Virginia, dated Jan. 23, 2018, 12 pages.

King, S.M., et al., "3D Proximal Tubule Tissues Recapitulate Key Aspects of Renal Physiology to Enable Nephrotoxicity Testing," Frontiers in Physiology, 3(123): 1-8, Frontiers Media S.A., Switzerland (2017).

Office Action dated Apr. 13, 2020 in U.S. Appl. No. 16/154,447, Nguyen, D., et al., filed Oct. 8, 2018, 6 pages.

Office Action dated Feb. 9, 2016 in U.S. Appl. No. 14/876,659, Nguyen, D., et al., filed Oct. 6, 2015, 12 pages.

Office Action dated Nov. 16, 2017 in U.S. Appl. No. 15/259,264, Nguyen, D., et al., filed Sep. 8, 2016, 7 pages.

Sanchez-Romero, N., et al., "In vitro systems to study nephropharmacology: 2D versus 3D models," European Journal of Pharmacology, 790: 36-45, Elsevier B.V., Netherlands (2016).

Supplementary European Search Report for EP Application No. EP 17 85 7412.5, Munich, Germany, dated Jul. 3, 2020, 10 pages.

Non-Final Office Action dated Apr. 15, 2021 in U.S. Appl. No. 16/334,937, King, S.M., et al., filed Mar. 20, 2019, 22 pages.

\* cited by examiner

- Vehicle
- 1 mM cimetidine
- 5 µM cisplatin
- 5 µM cisplatin + 1 mM cimetidine

- Vehicle Control
- 1 mM cimetidine
- 5 µM cisplatin
- 5 µM cisplatin + 1 mM cimetidine

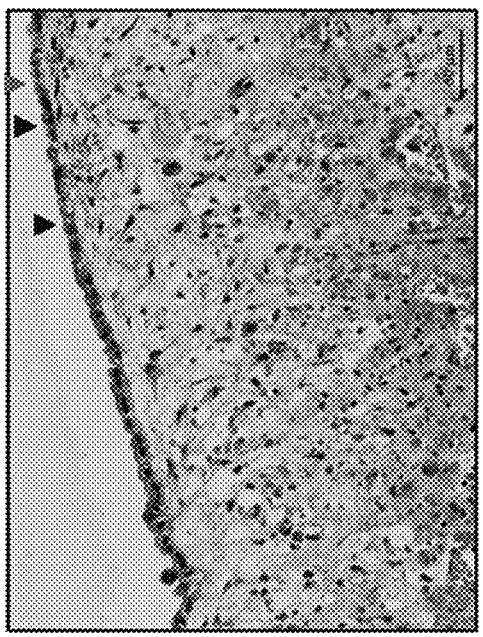
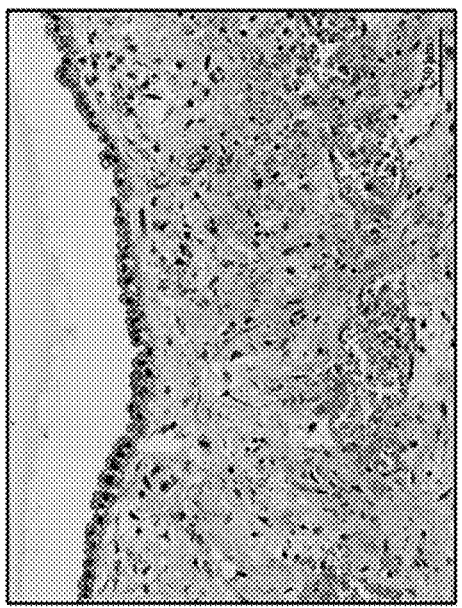
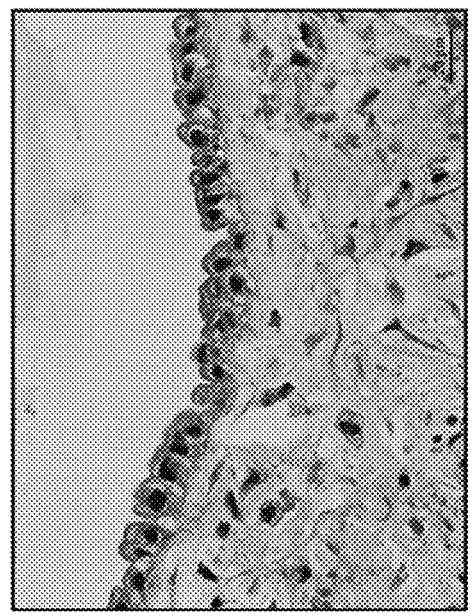

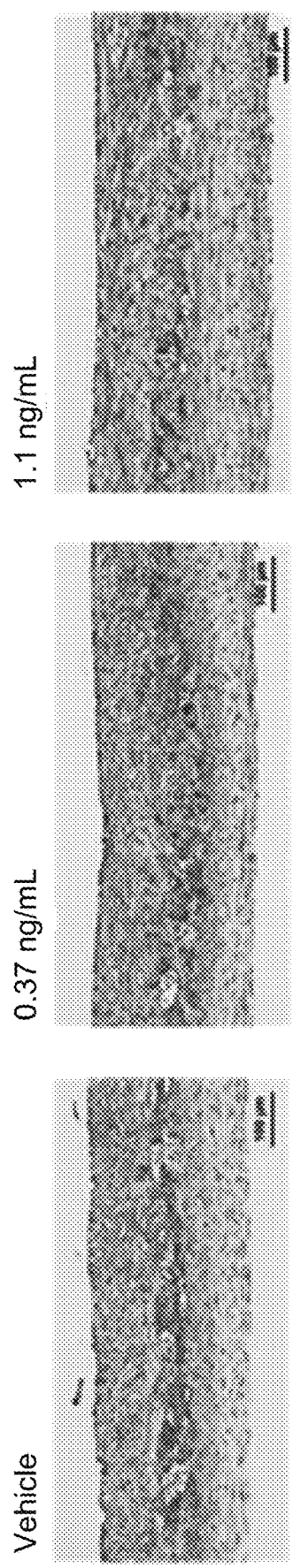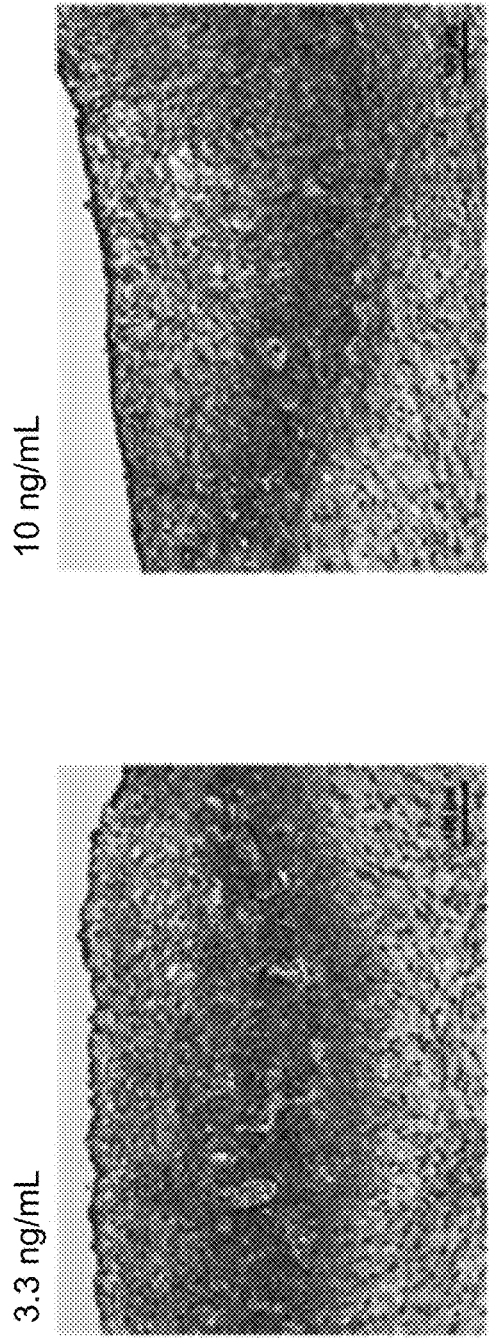

USE OF ENGINEERED RENAL TISSUES IN ASSAYS

CROSS-REFERENCE TO RELATED APPLICATIONS

This application is a division of application Ser. No. 16/334,937, filed Mar. 20, 2019, now allowed, which is a National Stage of International Application No. PCT/US2017/053997, filed Sep. 28, 2017, which claims the benefit under 35 U.S.C. § 119(e) of U.S. Provisional Application Nos. 62/453,367, filed Feb. 1, 2017, and 62/400,894, filed Sep. 28, 2016, the disclosures of each of which are incorporated herein by reference.

BACKGROUND OF THE INVENTION

Field of the Invention

The invention is in the field of renal tubule models and their use in assays. Disclosed are methods of assessing the ability of a candidate therapeutic agent to reverse, reduce, or prevent renal injury by a potential toxic agent using a three-dimensional, engineered, bioprinted, biological renal tubule model. Also disclosed are methods of assessing the effect of an agent on renal function, the method comprising contacting the agent with a three-dimensional, engineered, bioprinted, biological renal tubule model. Also disclosed are models of a renal disorder. In one embodiment, disclosed are models of renal fibrosis, comprising a three-dimensional, engineered, bioprinted, biological renal tubule model. Also disclosed are methods of making the model of a renal disorder. In one embodiment, disclosed are methods of making the model of renal fibrosis comprising contacting a three-dimensional, engineered, bioprinted, biological renal tubule model with an agent that is capable of inducing interstitial fibrotic tissue formation.

Background Art

The kidneys play a central role in the metabolism and elimination of a variety of drugs, with the proximal tubule (PT) being exposed to high concentrations of reactive hydrophilic metabolites at both the luminal surface following filtration of plasma at the glomerulus, as well as the basolateral surface following absorption from the peritubular capillaries. Due to the action of renal xenobiotic transporters expressed in the PT epithelium, pharmaceutical compounds can accumulate and become concentrated in the PT and may then undergo further metabolism by cytochrome P450 enzymes and UDP-glucuronyltransferases (Lohr et al., 1998). While this serves a role in detoxifying these compounds to generate more hydrophilic molecules that are secreted into the urine, highly toxic intermediate metabolites can accumulate and cause damage to the tubular epithelium and surrounding cells (Choudhury and Ahmed, 2006). As such, a major challenge in bringing new drugs to market is the risk of nephrotoxicity, which is often detected late in drug development; attrition due to nephrotoxicity accounts for 2% of preclinical drug attrition but 19% of attrition during more costly phase 3 clinical trials (Redfern, 2010). Post-approval, drug-induced nephrotoxicity accounts for as much as 18-27% of cases of acute kidney injury (AKI) (Loghman-Adham et al., 2012), with up to 36% of these injuries related to commonly used antibiotics such as aminoglycosides (Kleinknecht et al., 1987). While many of these AKI cases are reversible, some drugs can induce chronic renal injury resulting in tubular necrosis, tubulointerstitial inflammation, and fibrosis (Kleinknecht et al., 1987; Choudhury and Ahmed, 2006). Currently, diagnosis of AKI or renal failure relies on elevated creatinine or blood urea nitrogen levels, which do not become reliably clinically significant until the injury is severe (Rahman et al., 2012). The lasting effects of AKI are significant, with 13% of patients requiring continued dialysis and 41% of patients requiring kidney transplant due to renal insufficiency (Vaidya et al., 2008). Better predictive tools for identifying nephrotoxic drugs during the drug development process would therefore reduce the costs associated both with bringing a new drug to market and in treating the downstream effects of AKI, as well as improving patients' lives.

Currently, widely used screening tools for nephrotoxic compounds consist primarily of panels of human and animal renal proximal tubule epithelial cells (RPTEC) or small animal models. However, these systems often fail to accurately predict organ-specific toxicity, either as a result of species-specific differences, or the inability to recapitulate relevant aspects of kidney physiology, including toxicity following xenobiotic transport and biotransformation (Lin and Will, 2012). While freshly isolated primary human RPTEC obviate differences in species specificity, the cells rapidly dedifferentiate and senesce when cultured in isolation, losing expression of key transporters and metabolic enzymes (Wieser et al., 2008; Vesey et al., 2009). In the human kidney, the RPTEC exist in close connection with the renal interstitium, defined as the space between the cortical tubules comprising cells, extracellular matrix, proteoglycans, glycoproteins, and interstitial fluid (Lemley and Kriz, 1991). The cell types found in the cortical interstitium include fibroblast-like cells and immune cells, which are interspersed with the microvasculature of peritubular capillaries (Brenner, 2008). These supporting cell types may play a key role in maintaining the continued function of RPTEC, as co-culture of primary RPTEC with endothelial cells results in a robust paracrine signaling network that improves RPTEC proliferation and differentiation (Tasnim and Zink, 2012). Thus, placing primary RPTEC together with supporting interstitial cells in a more native, three-dimensional (3D) architecture may aid in maintaining their function over time, as well as allowing for assessment of additional types of kidney injury that are difficult to model using epithelial cells alone, such as fibrosis (Subramanian et al., 2010).

One of the primary aims of tissue engineering is to use living cells and biomaterials to generate 3D tissues that recapitulate key aspects of the architecture and function of a native tissue or organ. With proper in vitro or in vivo conditioning, the cells within these structures can respond to soluble and mechanical cues by establishing cell-cell and cell-matrix interactions that mimic some aspects of native tissue (Griffith et al., 2014). It is well established that cells cultured in 3D configurations, such as spheroids or collagen gels, perform differently in functional assays than 2D cultures, and the physiologic responses of cells in 3D more closely approximate responses observed in vivo (Godoy et al., 2013). One such means for fabricating these 3D structures is bioprinting. In this approach, bioinks composed of cellular material are extruded in reproducible, geometrically-defined patterns created by the investigator (Ozbolat and Hospodiuk, 2016). The bioink is composed of self-assembling multicellular aggregates that adhere to one another following deposition, leading to formation of complex, patterned tissues (Jakab et al., 2008; Jakab et al., 2010). Combining the use of self-assembling multicellular aggregates with computer-controlled bioprinting allows the creation of highly reproducible, scaffold-free tissues that form and mature in the absence of exogenous extracellular matrix that can interfere with direct cell-cell contacts (Norotte et al., 2009).

SUMMARY OF THE INVENTION

Bioprinting technology was leveraged to design and create layered tissue models of the human PT that incorporate key interstitial cell types supporting RPTEC to facilitate both cell-cell interactions and paracrine signaling between renal fibroblasts, endothelial cells, and epithelial cells. The resulting tissues supported epithelial morphology and function for at least 30 days in culture, and were effectively used to model the role of the organic cation transporter OCT2 in nephrotoxic responses to cisplatin using a combination of biochemical, transcriptional, and histological endpoints. Thus, this system is useful in predicting nephrotoxicity of pharmaceutical compounds earlier in the drug development process.

The engineered tissues described herein represent a model of the tubulointerstitial interface in which human renal interstitial tissue is supporting human renal proximal tubule epithelial cells to facilitate their optimal morphology and function. Creation of a three-dimensional tubulointerstitial interface facilitates the correct localization of drug transporters and receptors required for metabolism in order to accurately study how small molecules, chemicals, contaminants, or biologics affect the renal proximal tubule. This represents a more physiologically relevant alternative to two-dimensional monolayers of human or canine kidney epithelial cells and serves as an adjunct to, or in some cases, replacement of animal studies in which species difference in renal functions hamper interpretation of results.

The engineered tissues described herein provide an opportunity to accurately study how compounds affect the renal proximal tubule as well as modeling pathogenic processes that involve tubular transport, cell-cell interactions, and the development of renal disorders such as may occur in chronic renal disease, polycystic kidney disease, or type II diabetes.

The engineered tissues described herein provide an opportunity to accurately study how compounds affect the renal proximal tubule as well as modeling pathogenic processes that involve tubular transport, cell-cell interactions, and the development of renal disorders such as may occur in chronic renal disease, polycystic kidney disease, or type II diabetes.

The engineered tissues described herein provide an opportunity to accurately study how compounds affect the renal proximal tubule as well as modeling pathogenic processes that involve tubular transport, cell-cell interactions, and the development of tubulointerstitial fibrosis such as may occur in chronic renal disease, polycystic kidney disease, or type II diabetes.

Provided are methods of assessing the ability of a candidate therapeutic agent to reverse, reduce, or prevent renal injury by a potential toxic agent, the method comprising: contacting the potential toxic agent with a three-dimensional, engineered, bioprinted, biological renal tubule model; contacting the renal tubule model with the candidate therapeutic agent; determining the viability or functionality of the renal tubular epithelial cells; and assessing the ability of the candidate therapeutic agent to reverse, reduce, or prevent renal injury by the potential toxic agent based on the determined viability or functionality of the renal tubular epithelial cells compared to a control renal tubule model that has not been contacted with the candidate therapeutic agent. In some embodiments, the three-dimensional, engineered, bioprinted, biological renal tubule model comprises a layer of renal interstitial tissue, the renal interstitial tissue comprising renal fibroblasts and endothelial cells; and a layer of renal epithelial tissue, the renal epithelial tissue comprising renal tubular epithelial cells; provided that the interstitial tissue comprises an interstitial bio-ink, the epithelial tissue comprises an epithelial bio-ink, and form a three-dimensional, engineered, biological renal tubule model.

In some embodiments, the renal tubular epithelial cells are polarized. In some embodiments, the layer of renal interstitial tissue possesses an apical and basolateral surface.

In some embodiments, the model further comprises a layer of basement membrane between the renal interstitial tissue layer and the renal epithelial tissue layer. In some embodiments, the layer of renal epithelial tissue is in continuous contact with the layer of basement membrane, and the layer of basement membrane is in continuous contact with the layer of renal interstitial tissue.

In some embodiments, the layer of renal epithelial tissue is substantially a monolayer.

In some embodiments, the renal tubular epithelial cells are the only cells present in the layer of renal epithelial tissue. In other embodiments, the fibroblasts and endothelial cells are the only cells present in the layer of renal interstitial tissue. In other embodiments, the layer of renal interstitial tissue further comprises interstitial fibrotic tissue.

In some embodiments, the fibroblasts and endothelial cells are present in the layer of renal interstitial tissue at a ratio of about 50:50 fibroblasts to endothelial cells. In some embodiments, the layer of renal interstitial tissue or layer of renal epithelial tissue is between 70%-100% living cells by volume. In other embodiments, the layer of renal interstitial tissue further comprises interstitial fibrotic tissue.

In some embodiments, the renal tubule model further comprises a biocompatible membrane.

In some embodiments, the renal tubular model is of uniform thickness. In some embodiments, the renal tubular model is at least 2 cell layers thick.

In some embodiments, the fibroblasts and endothelial cells are present in a ratio at which the renal tubule model is planar six days post-printing.

In some embodiments, a plurality of the renal tubule models are configured to form an array. In some embodiments, the array is present in the wells of a microtiter plate.

In some embodiments, the potential toxic agent is a toxin, a therapeutic agent, an antimicrobial agent, a metal, or an environmental agent.

In other embodiments, the potential toxic agent is an antiviral, an analgesic agent, an antidepressant agent, a diuretic agent, or a proton pump inhibitor.

In other embodiments, the potential toxic agent is a cytokine, a chemokine, a small molecule drug, a large molecule drug, a protein or a peptide.

In other embodiments, the potential toxic agent is a chemotherapeutic agent which is an aromatase inhibitor; an anti-estrogen; an anti-androgen; a gonadorelin agonist; a topoisomerase I inhibitor; a topoisomerase II inhibitor; a microtubule active agent; an alkylating agent; a retinoid, a carontenoid, or a tocopherol; a cyclooxygenase inhibitor; an MMP inhibitor; an mTOR inhibitor; an antimetabolite; a platin compound; a methionine aminopeptidase inhibitor; a bisphosphonate; an antiproliferative antibody; a heparanase inhibitor; an inhibitor of Ras oncogenic isoforms; a telomerase inhibitor; a proteasome inhibitor; a compound used in the treatment of hematologic malignancies; a Flt-3 inhibitor; an Hsp90 inhibitor; a kinesin spindle protein inhibitor; a MEK inhibitor; an antitumor antibiotic; a nitrosourea; a compound targeting/decreasing protein or lipid kinase activity, a compound targeting/decreasing protein or lipid phosphatase activity, or an anti-angiogenic compound.

In other embodiments, the potential toxic agent is a chemotherapeutic agent which is daunorubicin, adriamycin, Ara-C, VP-16, teniposide, mitoxantrone, idarubicin, cisplatin, carboplatinum, PKC412, 6-mercaptopurine (6-MP), fludarabine phosphate, octreotide, SOM230, FTY720, 6-thioguanine, cladribine, 6-mercaptopurine, pentostatin, hydroxyurea, 2-hydroxy-1H-isoindole-1,3-dione derivatives, 1-(4-chloroanilino)-4-(4-pyridylmethyl)phthalazine, 1-(4-chloroanilino)-4-(4-pyridylmethyl)phthalazine succinate, angiostatin, endostatin, anthranilic acid amides, ZD4190, ZD6474, SU5416, SU6668, bevacizumab, rhuMAb, rhuFab, macugon, FLT-4 inhibitors, FLT-3 inhibitors, VEGFR-2 IgGI antibody, RPI 4610, bevacizumab, porfimer sodium, anecortave, triamcinolone, hydrocortisone, 11-α-epihydrocotisone, cortex olone, 17a-hydroxyprogesterone, corticosterone, desoxycorticosterone, testosterone, estrone, dexamethasone, fluocinolone, a plant alkaloid, a hormonal compound and/or antagonist, a biological response modifier, such as a lymphokine or interferon, an antisense oligonucleotide or oligonucleotide derivative, shRNA, siRNA, or a pharmaceutically acceptable salt thereof.

In other embodiments, the potential toxic agent is acetaminophen, lithium, acyclovir, amphotericin B, and aminoglycoside, a beta lactams, foscavir, ganciclovir, pentamidine, a quinolone, a sulfonamide, vancomycin, rifampin, adefovir, indinavir, didofovir, tenofovir, methotrexate, lansoprazole, omeprazole, pantoprazole, allopurinol, phenytoin, ifosfamide, gentamycin, or zoledronate.

In other embodiments, the potential toxic agent is radiation.

In some embodiments, the viability or functionality of the renal tubular epithelial cells is determined by measuring an indicator of metabolic activity. In some embodiments, the indicator of metabolic activity is resazurin reduction or tetrazolium salt reduction in the renal tubule mode compared to a control.

In other embodiments, the viability or functionality of the renal tubular epithelial cells is determined by measuring lactate dehydrogenase (LDH) activity, gamma glutamyl-transferase (GGT) activity, protease activity, ATP utilization, glucose uptake activity, sodium-glucose co-transporter-2 (SGLT2) activity or RNA expression compared to a control.

In other embodiments, the viability or functionality of the renal tubular epithelial cells is determined by measuring a renal transport molecule activity in the model compared to a control. In some embodiments, the transport molecule activity is excretion and/or uptake of at least one macromolecule. In some embodiments, the macromolecule is albumin.

In other embodiments, the viability or functionality of the renal tubular epithelial cells is determined by identifying regeneration of the renal tubular epithelial cells compared to a control.

In other embodiments, the viability or functionality of the renal tubular epithelial cells is determined by measuring the trans-epithelial electrical resistance or the passive permeability of the renal tubule model compared to a control.

In other embodiments, the viability or functionality of the renal tubular epithelial cells is determined by measuring changes in vitamin D production, changes in angiotensin conversion, alterations to ion exchange, alterations to pH, alterations to acid/base balance, alterations to renal tubule barrier function, or alterations to the intrarenal renin/angiotensin system (RAS), alterations in physiology, alterations in pathology, alterations to transport of molecules, alterations to sodium-glucose cotransporter-2 (SGLT2) activity, amounts of interstitial fibrotic tissue, or regeneration of the renal tubule model compared to a control.

In other embodiments, the viability or functionality of the renal tubular epithelial cells is determined by measuring amounts of interstitial fibrotic tissue compared to a control.

In other embodiments, the viability or functionality of the renal tubular epithelial cells is measured over time.

In some embodiments, the renal tubule model is contacted first with the potential toxic agent and then with the candidate therapeutic agent. In other embodiments, the renal tubule model is contacted first with the candidate therapeutic agent and then with the potential toxic agent.

In some embodiments, the renal tubule model has been cultured in a cell culture medium prior to being contacted with the candidate therapeutic agent and the potential toxic agent.

In some embodiments, the renal tubule model has been cultured for 3 or more days in the cell culture medium.

Also provided are methods of assessing the effect of an agent on renal function, the method comprising contacting the agent with a three-dimensional, engineered, bioprinted, biological renal tubule model; and measuring the effect of the agent on the viability or functionality of the renal tubular epithelial cells. In some embodiments, the three-dimensional, engineered, bioprinted, biological renal tubule model comprises a layer of renal interstitial tissue, the renal interstitial tissue comprising renal fibroblasts and endothelial cells; and a layer of renal epithelial tissue, the renal epithelial tissue comprising renal tubular epithelial cells, to form the three-dimensional, engineered, biological renal tubule model; provided that the interstitial tissue comprises an interstitial bio-ink, the epithelial tissue comprises an epithelial bio-ink, and form a three-dimensional, engineered, biological renal tubule model.

In some embodiments, the fibroblasts and endothelial cells are present in a ratio of fibroblasts to endothelial cells at which the renal tubule model is planar six days post-printing.

In some embodiments, the renal tubular epithelial cells are polarized. In some embodiments, the layer of renal interstitial tissue possesses an apical and basolateral surface.

In some embodiments, the model further comprises a layer of basement membrane between the renal interstitial tissue layer and the renal epithelial tissue layer. In some embodiments, the layer of renal epithelial tissue is in continuous contact with the layer of basement membrane and wherein the layer of basement membrane is in continuous contact with the layer of renal interstitial tissue.

In some embodiments, the layer of renal epithelial tissue is substantially a monolayer.

In some embodiments, renal tubular epithelial cells are the only cells present in the layer of renal epithelial tissue. In other emobodiments, the fibroblasts and endothelial cells are the only cells present in the layer of renal interstitial tissue. In some embodiments, the layer of renal interstitial tissue further comprises interstitial fibrotic tissue.

In some embodiments, the fibroblasts and endothelial cells are present in the layer of renal interstitial tissue at a ratio of about 50:50 fibroblasts to endothelial cells.

In some embodiments, any of the layer of renal interstitial tissue or layer of renal epithelial tissue is between 70%-100% living cells by volume.

In some embodiments, the renal tubule model further comprises a biocompatible membrane.

In some embodiments, the renal tubular model is of uniform thickness. In other embodiments, the renal tubule model is 2 or more cell layers thick.

In some embodiments, a plurality of the renal tubule models are configured to form an array. In some embodiments, the array is present in the wells of a microtiter plate.

In some embodiments, the agent is a toxin, a therapeutic agent, an antimicrobial agent, a metal, or an environmental agent.

In other embodiments, the agent is an antiviral, an analgesic agent, an antidepressant agent, a diuretic agent, or a proton pump inhibitor.

In other embodiments, the agent is a cytokine, a chemokine, a small molecule drug, a large molecule drug, a protein or a peptide.

In other embodiments, the agent is a chemotherapeutic agent which is an aromatase inhibitor; an anti-estrogen; an anti-androgen; a gonadorelin agonist; a topoisomerase I inhibitor; a topoisomerase II inhibitor; a microtubule active agent; an alkylating agent; a retinoid, a carontenoid, or a tocopherol; a cyclooxygenase inhibitor; an MMP inhibitor; an mTOR inhibitor; an antimetabolite; a platin compound; a methionine aminopeptidase inhibitor; a bisphosphonate; an antiproliferative antibody; a heparanase inhibitor; an inhibitor of Ras oncogenic isoforms; a telomerase inhibitor; a proteasome inhibitor; a compound used in the treatment of hematologic malignancies; a Flt-3 inhibitor; an Hsp90 inhibitor; a kinesin spindle protein inhibitor; a MEK inhibitor; an antitumor antibiotic; a nitrosourea; a compound targeting/decreasing protein or lipid kinase activity, a compound targeting/decreasing protein or lipid phosphatase activity, or an anti-angiogenic compound.

In other embodiments, the agent is a chemotherapeutic agent which is daunorubicin, adriamycin, Ara-C, VP-16, teniposide, mitoxantrone, idarubicin, cisplatin, carboplatinum, PKC412, 6-mercaptopurine (6-MP), fludarabine phosphate, octreotide, SOM230, FTY720, 6-thioguanine, cladribine, 6-mercaptopurine, pentostatin, hydroxyurea, 2-hydroxy-1H-isoindole-1,3-dione derivatives, 1-(4-chloroanilino)-4-(4-pyridylmethyl)phthalazine, 1-(4-chloroanilino)-4-(4-pyridylmethyl)phthalazine succinate, angiostatin, endostatin, anthranilic acid amides, ZD4190, ZD6474, SU5416, SU6668, bevacizumab, rhuMAb, rhuFab, macugon, FLT-4 inhibitors, FLT-3 inhibitors, VEGFR-2 IgGI antibody, RPI 4610, bevacizumab, porfimer sodium, anecortave, triamcinolone, hydrocortisone, 11-α-epihydrocotisone, cortex olone, 17a-hydroxyprogesterone, corticosterone, desoxycorticosterone, testosterone, estrone, dexamethasone, fluocinolone, a plant alkaloid, a hormonal compound and/or antagonist, a biological response modifier, such as a lymphokine or interferon, an antisense oligonucleotide or oligonucleotide derivative, shRNA, siRNA, or a pharmaceutically acceptable salt thereof.

In other embodiments, the agent is acetaminophen, lithium, acyclovir, amphotericin B, an aminoglycoside, a beta lactam, foscavir, ganciclovir, pentamidine, a quinolone, a sulfonamide, vancomycin, rifampin, adefovir, indinavir, didofovir, tenofovir, methotrexate, lansoprazole, omeprazole, pantopraxole, allopurinol, phenytoin, ifosfamide, gentamycin, or zoledronate.

In other embodiments, the agent is radiation.

In some embodiments, the viability or functionality of the renal tubular epithelial cells is determined by measuring an indicator of metabolic activity. In some embodiments, the indicator of metabolic activity is resazurin reduction or tetrazolium salt reduction in the renal tubule mode compared to a control.

In other embodiments, the viability or functionality of the renal tubular epithelial cells is determined by measuring lactate dehydrogenase (LDH) activity, gamma glutamyltransferase (GGT) activity, protease activity, ATP utilization, SGLT2 activity, glucose uptake activity or RNA expression compared to a control.

In other embodiments, the viability or functionality of the renal tubular epithelial cells is determined by measuring a renal transport molecule activity in the model compared to a control. In some embodiments, the transport molecule activity is excretion and/or uptake of at least one macromolecule. In some embodiments, the macromolecule is albumin.

In other embodiments, the viability or functionality of the renal tubular epithelial cells is determined by identifying regeneration of the renal tubular epithelial cells compared to a control.

In other embodiments, the viability or functionality of the renal tubular epithelial cells is determined by measuring the trans-epithelial electrical resistance or the passive permeability of the renal tubule model compared to a control.

In other embodiments, the viability or functionality of the renal tubular epithelial cells is determined by measuring changes in vitamin D production, changes in angiotensin conversion, alterations to ion exchange, alterations to pH, alterations to acid/base balance, alterations to renal tubule barrier function, alterations to the intrarenal renin/angiotensin system (RAS), alterations in physiology, alterations in pathology, alterations to transport of molecules, alterations to sodium-glucose cotransporter-2 (SGLT2) activity, amounts of interstitial fibrotic tissue, or regeneration of the renal tubule model compared to a control.

In other embodiments, the viability or functionality of the renal tubular epithelial cells is measured over time.

In some embodiments, the renal tubule model has been cultured in a cell culture medium prior to being contacted with the agent. In some embodiments, the renal tubule model has been cultured for 3 or more days in the cell culture medium.

In some embodiments, the agent is removed, and the renal tubule model is assessed to determine whether the absence of the agent results in improved viability or functionality of the renal tubular epithelial cells.

Also provided are models of renal fibrosis, comprising a three-dimensional, engineered, bioprinted, biological renal tubule model. The three-dimensional, engineered, bioprinted, biological renal tubule model comprises a layer of renal interstitial tissue, the renal interstitial tissue comprising renal fibroblasts, endothelial cells and fibrotic tissue; and a layer of renal epithelial tissue, the renal epithelial tissue comprising renal tubular epithelial cells, to form the three-dimensional, engineered, biological renal tubule model; provided that the interstitial tissue comprises an interstitial bio-ink, the epithelial tissue comprises an epithelial bio-ink, and form a three-dimensional, engineered, biological renal tubule model. In some embodiments, the model displays contraction, curling, expansion of the tissue, or another fibrosis phenotype when fibrosis is present in the model.

In some embodiments, the renal tubular epithelial cells are polarized. In some embodiments, the layer of renal interstitial tissue possesses an apical and basolateral surface.

In some embodiments, the model further comprises a layer of basement membrane between the renal interstitial tissue layer and the renal epithelial tissue layer. In some embodiments, the layer of renal epithelial tissue is in continuous contact with the layer of basement membrane, and the layer of basement membrane is in continuous contact with the layer of renal interstitial tissue.

In some embodiments, the layer of renal epithelial tissue is substantially a monolayer.

In some embodiments, renal tubular epithelial cells are the only cells present in the layer of renal epithelial tissue. In some embodiments, the fibroblasts and endothelial cells are the only cells present in the layer of renal interstitial tissue.

In some embodiments, the fibroblasts and endothelial cells are present in the layer of renal interstitial tissue at a ratio of about 50:50 fibroblasts to endothelial cells.

In some embodiments, the layer of renal interstitial tissue or layer of renal epithelial tissue is between 70%-100% living cells by volume.

In some embodiments, the renal tubule model further comprises a biocompatible membrane.

In some embodiments, the renal tubular model displays deformation of the planar tissue structure and excess extracellular matrix deposition.

In some embodiments, the renal tubular model is 2 or more cell layers thick.

In some embodiments, a plurality of the renal tubule models are configured to form an array. In some embodiments, the array is present in the wells of a microtiter plate.

In some embodiments, the fibroblasts and endothelial cells are present at a ratio at which the renal tubule model is planar six days post printing.

Also provided are methods of making the model of renal fibrosis comprising contacting a three-dimensional, engineered, bioprinted, biological renal tubule model with an agent that is capable of inducing interstitial fibrotic tissue formation, wherein the renal tubule model comprises a layer of renal interstitial tissue, the renal interstitial tissue comprising renal fibroblasts and endothelial cells; and a layer of renal epithelial tissue, the renal epithelial tissue comprising renal tubular epithelial cells, to form the three-dimensional, engineered, biological renal tubule model; provided that the interstitial tissue comprises an interstitial bio-ink, the epithelial tissue comprises an epithelial bio-ink, and form a three-dimensional, engineered, biological renal tubule model.

In some embodiments, the fibroblasts and endothelial cells are present in a ratio of fibroblasts to endothelial cells at which the renal tubule model is planar six days post printing.

In some embodiments, the agent that is capable of inducing interstitial fibrotic tissue deposition is cyclosporine A, aristolochoic acid, tacrolimus, TGFbeta, cisplatin, acyclovir, allopurinol, beta lactam antibiotics, indinavir, lansoprazole, omeprazole, pantoprazole, phenytoin, ranitidine, or vancomycin.

Also provided is a model of a renal disorder, comprising a three-dimensional, engineered, bioprinted, biological tubule model comprising:
(a) a layer of renal interstitial tissue, the renal interstitial tissue comprising renal fibroblasts and endothelial cells; and
(b) a layer of renal epithelial tissue, the renal epithelial tissue comprising renal tubular epithelial cells, to form the three-dimensional, engineered, biological renal tubule model; provided that the interstitial tissue comprises an interstitial bio-ink, the epithelial tissue comprises an epithelial bio-ink, and form a three-dimensional, engineered, biological renal tubule model, wherein the model comprises a phenotype that is characteristic of a renal disorder in the renal tubule.

In some embodiments, the phenotype includes at least one of contraction, curling, expansion, necrosis, apoptosis, tubular regeneration, compensatory proliferation, epithelial-mesenchymal transition, inflammation, ischemia, ischemia/reperfusion, reactive oxygen species, changes in the mitochondria, changes to cell morphology, changes to nuclear morphology, hyperproliferation, alterations in gene expression, secretion of biomarkers, epigenetic modifications, crystal deposition, cyst formation, a change to a cellular function, angiogenesis, hypoxia, extraceullar matrix deposition, or death of surrounding tissue.

In some embodiments, the renal tubular epithelial cells are polarized.

In some embodiments, the layer of renal interstitial tissue possesses an apical and basolateral surface.

In some embodiments, the model further comprises a layer of basement membrane between the renal interstitial tissue layer and the renal epithelial tissue layer.

In some embodiments, the layer of renal epithelial tissue is in continuous contact with the layer of basement membrane and wherein the layer of basement membrane is in continuous contact with the layer of renal interstitial tissue.

In some embodiments, the layer of renal epithelial tissue is substantially a monolayer.

In some embodiments, renal tubular epithelial cells are the only cells present in the layer of renal epithelial tissue.

In some embodiments, the fibroblasts and endothelial cells are the only cells present in the layer of renal interstitial tissue.

In some embodiments, the fibroblasts and endothelial cells are present in the layer of renal interstitial tissue at a ratio of about 50:50 fibroblasts to endothelial cells.

In some embodiments, the layer of renal interstitial tissue or layer of renal epithelial tissue is between 70%-100% living cells by volume.

In some embodiments, the renal tubule model further comprises a biocompatible membrane.

In some embodiments, the renal tubular model displays deformation of the planar tissue structure and excess extracellular matrix deposition.

In some embodiments, the renal tubular model is at least 2 cell layers thick.

In some embodiments, a plurality of the renal tubule models are configured to form an array.

In some embodiments, the array is present in the wells of a microtiter plate.

In some embodiments, the fibroblasts and endothelial cells are present at a ratio at which the renal tubule model is planar six days post printing.

In some embodiments, the renal disorder is associated with a congenital abnormality, diabetes, an immune complex disease, vascular sclerosis, renal ablation, renal fibrosis, hypertension, arterionephrosclerosis, lupus nephritis, vascular disease, inflammation, hemolytic-uremic syndrome, obstructive nephropathy, dyslipoproteinemia, recurrent dehydration, reflux nephropathy, radiation nephropathy, atheroembolic renal disease, scleroderma, sickle cell anemia, retention of lipids, infection, ischemia, ischemia/reperfusion, a transport deficiency, crystal deposition, a genetic disorder, a chronic system disorder, renal cancer, or a combination thereof.

In some embodiments, the phenotype is induced by contacting the renal tubule model with a treatment, compound, or infectious agent that gives rise to the phenotype.

In some embodiments, the phenotype is the presence of a tumor, a tumor fragment, a tumor cell, or an immortalized cell in the the renal tubule model.

In some embodiments, the fibroblasts, endothelial cells, epithelial cells, or combinations thereof of the renal tubule model are primary cells obtained from a diseased donor.

In some embodiments, further comprising a genetically modified cell, wherein the phenotype is induced by the genetically modified cell.

In some embodiments, the treatment, compound, or infectious agent that gives rise to the phenotype is a toxin, a potential toxic agent, an antimicrobial agent, a metal, or an environmental agent.

In some embodiments, the potential toxic agent is an anti-infective, an analgesic agent, an antidepressant agent, a diuretic agent, or a proton pump inhibitor.

In some embodiments, the potential toxic agent is a cytokine, a chemokine, a small molecule drug, a large molecule drug, a protein, or a peptide.

In some embodiments, the potential toxic agent is a chemotherapeutic agent which is an aromatase inhibitor; an anti-estrogen; an anti-androgen; a gonadorelin agonist; a topoisomerase I inhibitor; a topoisomerase II inhibitor; a microtubule active agent; an alkylating agent; a retinoid, a carontenoid, or a tocopherol; a cyclooxygenase inhibitor; an MMP inhibitor; an mTOR inhibitor; an antimetabolite; a platin compound; a methionine aminopeptidase inhibitor; a bisphosphonate; an antiproliferative antibody; a heparanase inhibitor; an inhibitor of Ras oncogenic isoforms; a telomerase inhibitor; a proteasome inhibitor; a compound used in the treatment of hematologic malignancies; a Flt-3 inhibitor; an Hsp90 inhibitor; a kinesin spindle protein inhibitor; a MEK inhibitor; an antitumor antibiotic; a nitrosourea; a compound targeting/decreasing protein or lipid kinase activity; a compound targeting/decreasing protein or lipid phosphatase activity; or an anti-angiogenic compound.

In some embodiments, the potential toxic agent is a chemotherapeutic agent which is daunorubicin, adriamycin, Ara-C, VP-16, teniposide, mitoxantrone, idarubicin, cisplatin, carboplatinum, PKC412, 6-mercaptopurine (6-MP), fludarabine phosphate, octreotide, SOM230, FTY720, 6-thioguanine, cladribine, 6-mercaptopurine, pentostatin, hydroxyurea, 2-hydroxy-1H-isoindole-1,3-dione derivatives, 1-(4-chloroanilino)-4-(4-pyridylmethyl)phthalazine, 1-(4-chloroanilino)-4-(4-pyridylmethyl)phthalazine succinate, angiostatin, endostatin, anthranilic acid amides, ZD4190, ZD6474, SU5416, SU6668, bevacizumab, rhuMAb, rhuFab, macugon, FLT-4 inhibitors, FLT-3 inhibitors, VEGFR-2 IgGI antibody, RPI 4610, bevacizumab, porfimer sodium, anecortave, triamcinolone, hydrocortisone, 11-α-epihydrocotisone, cortex olone, 17a-hydroxyprogesterone, corticosterone, desoxycorticosterone, testosterone, estrone, dexamethasone, fluocinolone, a plant alkaloid, a hormonal compound and/or antagonist, a biological response modifier, such as a lymphokine or interferon, an antisense oligonucleotide or oligonucleotide derivative, shRNA, siRNA, or a pharmaceutically acceptable salt thereof.

In some embodiments, the potential toxic agent is acetaminophen, lithium, acyclovir, amphotericin B, an aminoglycoside, a beta lactam, foscavir, ganciclovir, pentamidine, a quinolone, a sulfonamide, vancomycin, rifampin, adefovir, indinavir, didofovir, tenofovir, methotrexate, lansoprazole, omeprazole, pantopraxole, allopurinol, phenytoin, ifosfamide, gentamycin, or zoledronate.

In some embodiments, the potential toxic agent is radiation.

In some embodiments, the renal disorder is acute renal disorder, chronic renal disorder, or renal cancer.

Also provided is a method of assessing the ability of a candidate therapeutic agent to reverse, reduce, induce, or prevent a renal disorder, the method comprising:
(a) contacting a renal tubule model with a candidate therapeutic agent;
(b) determining a viability or functionality of the renal tissue cells; and
(c) assessing an ability of the candidate therapeutic to reverse, reduce, induce, or prevent a renal disorder based on the determined viability or functionality of the renal tissue cells compared to a control renal tubule model that has not been contacted with the candidate therapeutic agent.

In some embodiments, the method of assessing a candidate therapeutic further comprises:
(d) removing the candidate therapeutic agent; and
(e) assessing whether the absence of the agent results in improved viability or functionality of the renal tissue cells.

In some embodiments, the phenotype is the presence of a tumor, a tumor fragment, a tumor cell, or an immortalized cell in the the renal tubule model.

In some embodiments, the fibroblasts, endothelial cells, epithelial cells, or combinations thereof of the renal tubule model are primary cells obtained from a diseased donor.

In some embodiments, the candidate therapeutic agent is an antiviral, an analgesic agent, an antidepressant agent, a diuretic agent, or a proton pump inhibitor.

In some embodiments, the candidate therapeutic agent is a cytokine, a chemokine, a small molecule drug, a large molecule drug, a protein, or a peptide.

In some embodiments, the candidate therapeutic agent is a chemotherapeutic agent which is an aromatase inhibitor; an anti-estrogen; an anti-androgen; a gonadorelin agonist; a topoisomerase I inhibitor; a topoisomerase II inhibitor; a microtubule active agent; an alkylating agent; a retinoid, a carontenoid, or a tocopherol; a cyclooxygenase inhibitor; an MMP inhibitor; an mTOR inhibitor; an antimetabolite; a platin compound; a methionine aminopeptidase inhibitor; a bisphosphonate; an antiproliferative antibody; a heparanase inhibitor; an inhibitor of Ras oncogenic isoforms; a telomerase inhibitor; a proteasome inhibitor; a compound used in the treatment of hematologic malignancies; a Flt-3 inhibitor; an Hsp90 inhibitor; a kinesin spindle protein inhibitor; a MEK inhibitor; an antitumor antibiotic; a nitrosourea; a compound targeting/decreasing protein or lipid kinase activity; a compound targeting/decreasing protein or lipid phosphatase activity; or an anti-angiogenic compound.

In some embodiments, the candidate therapeutic agent is a chemotherapeutic agent which is daunorubicin, adriamycin, Ara-C, VP-16, teniposide, mitoxantrone, idarubicin, cisplatin, carboplatinum, PKC412, 6-mercaptopurine (6-MP), fludarabine phosphate, octreotide, SOM230, FTY720, 6-thioguanine, cladribine, 6-mercaptopurine, pentostatin, hydroxyurea, 2-hydroxy-1H-isoindole-1,3-dione derivatives, 1-(4-chloroanilino)-4-(4-pyridylmethyl)phthalazine, 1-(4-chloroanilino)-4-(4-pyridylmethyl)phthalazine succinate, angiostatin, endostatin, anthranilic acid amides, ZD4190, ZD6474, SU5416, SU6668, bevacizumab, rhuMAb, rhuFab, macugon, FLT-4 inhibitors, FLT-3 inhibitors, VEGFR-2 IgGI antibody, RPI 4610, bevacizumab, porfimer sodium, anecortave, triamcinolone, hydrocortisone, 11-α-epihydrocotisone, cortex olone, 17a-hydroxyprogesterone, corticosterone, desoxycorticosterone, testosterone, estrone, dexamethasone, fluocinolone, a plant alkaloid, a hormonal compound and/or antagonist, a biological response modifier, such as a lymphokine or interferon, an antisense oligonucleotide or oligonucleotide derivative, shRNA, siRNA, or a pharmaceutically acceptable salt thereof.

In some embodiments, the candidate therapeutic agent is acetaminophen, lithium, acyclovir, amphotericin B, an aminoglycoside, a beta lactam, foscavir, ganciclovir, pentamidine, a quinolone, a sulfonamide, vancomycin, rifampin, adefovir, indinavir, didofovir, tenofovir, methotrexate, lansoprazole, omeprazole, pantopraxole, allopurinol, phenytoin, ifosfamide, gentamycin, or zoledronate.

In some embodiments, the candidate therapeutic agent is radiation.

In some embodiments, the viability or functionality of the renal tissue cells is determined by measuring an indicator of metabolic activity.

In some embodiments, the indicator of metabolic activity is resazurin reduction or tetrazolium salt reduction in the renal tubule mode compared to a control.

In some embodiments, the viability or functionality of the renal tissue cells is determined by measuring lactate dehydrogenase (LDH) activity, gamma glutamyl-transferase (GGT) activity, protease activity, ATP utilization, SGLT2 activity, glucose uptake activity or RNA expression compared to a control.

In some embodiments, the viability or functionality of the renal tissue cells is determined by measuring a renal transport molecule activity in the model compared to a control.

In some embodiments, the transport molecule activity is excretion and/or uptake of at least one macromolecule.

In some embodiments, the macromolecule is a protein.

In some embodiments, the viability or functionality of the renal tissue cells is determined by identifying regeneration of the renal tubular epithelial cells compared to a control.

In some embodiments, the viability or functionality of the renal tissue cells is determined by measuring the transepithelial electrical resistance or the passive permeability of the renal tubule model compared to a control.

In some embodiments, the viability or functionality of the renal tissue cells is determined by measuring changes in vitamin D production, changes in angiotensin conversion, alterations to ion exchange, alterations to pH, alterations to acid/base balance, alterations to renal tubule barrier function, alterations to the intrarenal renin/angiotensin system (RAS), alterations in physiology, alterations in pathology, alterations to transport of molecules, alterations to sodium-glucose cotransporter-2 (SGLT2) activity, amounts of interstitial fibrotic tissue, or regeneration of the renal tubule model compared to a control.

In some embodiments, the viability or functionality of the renal tissue cells is determining by measuring changes in cytoplasmic proline-rich tyrosine kinase-2 (Pyk2) expression, thiazide-sensitive cotransporter (TSC) expression, epidermal growth factor (EGF) expression, transforming growth factor-alpha (TGF-α) expression, stem cell factor (SCF) expression, transforming growth factor-beta (TGF-β) expression, connective growth tissue factor (CTGF) expression, complement factor B expression, toll-like receptor 2 (TLR2) expression, toll-like receptor 4 (TLR4) expression, interleukin-6 (IL-6) expression, Class II major histocompatibility complex (MHC) expression, intercellular adhesion moleculare-1 (ICAM-1) expression, monocyte chemoattractant protein-1 (MCP-1) expression, or plasminogen activator inhibitor-1 (PAI-1) compared to a control.

In some embodiments, the viability or functionality of the renal tissue cells is determined by measuring induction of an apoptotic pathway, changes in cellular or nuclear morphology, changes in the number or morphology of mitochondria, changes in mitochondrial function, secretion of chemokines, secretion of cytokines, changes in the amount or pattern of deposition of extracellular matrix, deposition of protein crystals or salt crystals, tubular regeneration, epithelial-mesenchymal transition, inflammation, ischemia, ischemia/reperfusion, hyperproliferation, alterations in gene expression, secretion of biomarkers, or epigenetic modifications.

In some embodiments, the viability or functionality of the renal tissue cells is measured over time.

In some embodiments, the renal tubule model has been cultured in a cell culture medium prior to being contacted with the candidate therapeutic agent.

In some embodiments, the renal tubule model has been cultured for at least 3 days in the cell culture medium.

In some embodiments, the diseased donor has a congenital abnormality, diabetes, an immune complex disease, vascular sclerosis, renal ablation, renal fibrosis, hypertension, arterionephrosclerosis, lupus nephritis, vascular disease, inflammation, hemolytic-uremic syndrome, obstructive nephropathy, dyslipoproteinemia, recurrent dehydration, reflux nephropathy, radiation nephropathy, atheroembolic renal disease, scleroderma, sickle cell anemia, retention of lipids, infection, ischemia, a transport deficiency, crystal deposition, a genetic disorder, a chronic system disorder, renal cancer, In some embodiments, further comprising a genetically modified cell, wherein the phenotype is induced by the genetically modified cell.

Also provided is a method of predicting the effective dosing concentration and dosing schedule of a candidate therapeutic agent, the method comprising contacting varying concentrations or amounts of the agent with the three-dimensional, engineered, bioprinted, biological renal tissue model; and measuring the effect of the agent on the viability or functionality of the renal tissue cells over time.

In some embodiments, the method further comprises measuring a recovery of the renal tissue cells over time to determine a minimum timing between doses that provide efficacy.

The present invention also provides a method of making a renal tubule disorder model, the method comprising forming a three-dimensional, engineered, biological renal tubule disorder model by contacting a first layer of renal tissue with a second layer of renal tissue, provided that the first layer of renal tissue comprises renal interstitial tissue, the second layer of renal tissue comprises epithelial tissue, and at least one renal tissue layer comprises a bio-ink having diseased cells.

In some embodiments, the diseased cells of the bio-ink comprise genetically modified cells specific to a disease.

In some embodiments, the genetically modified cells are genetically modified stem cells.

In some embodiments, the genetically modified cells are genetically modified fibroblast cells, endothelial cells, epithelial cells, or any combination thereof. In some embodiments, the genetically modified cells include a polycystic mutation in a transporter, a retrovirus, a CRISPR, a viral transduction, a chemical mutagenesis, or any combination thereof.

In some embodiments, the diseased cells of the bio-ink comprise cells isolated from a donor with a specific disease.

In some embodiments, the donor has a genetic dysfunction corresponding to the specific disease.

In some embodiments, the cells isolated from the donor are induced pluripotent stem cells.

In some embodiments, at least a second renal tissue layer comprises a bio-ink having diseased cells.

In some embodiments, the renal interstitial tissue comprises renal fibroblasts and endothelial cells, and the renal epithelial tissue comprises renal tubular epithelial cells.

The present invention also provides a method of making a renal tubule disorder model, the method comprising conditioning a three-dimensional, engineered, bioprinted, biological renal tubule model to produce a phenotype characteristic of a desired renal tubule disorder, wherein the renal tubule model comprises: a layer of renal interstitial tissue, the renal interstitial tissue comprising renal fibroblasts and endothelial cells; and a layer of renal epithelial tissue, the renal epithelial tissue comprising renal tubular epithelial cells, to form the three-dimensional, engineered, biological renal tubule model; provided that the interstitial tissue comprises an interstitial bio-ink, the epithelial tissue comprises an epithelial bio-ink, and form a three-dimensional, engineered, biological renal tubule model.

In some embodiments, the conditioning step is genetically modifying the cells to produce the phenotype characteristic of the desired renal tubule disorder.

In some embodiments, the cells are genetically modified by a polycystic mutation in a transporter, a retovirus, a CRISPR, a viral transduction, a chemical mutagenesis, or any combination thereof.

In some embodiments, the conditioning step includes contacting the three-dimensional, engineered, biological renal tubule model with an agent capable of inducing the phenotype characteristic of the desired renal tubule disorder.

In some embodiments, the agent is a toxicant. In some embodiments, the toxicant includes one or more of the following: anti-infective, antibiotics, antibacterials, antifungals, antivirals, acetaminophen, lithium, acyclovir, amphotericin B, an aminoglycoside, a beta lactam, foscavir, ganciclovir, pentamidine, a quinolone, a sulfonamide, vancomycin, rifampin, adefovir, indinavir, didofovir, tenofovir, methotrexate, lansoprazole, omeprazole, pantoprazole, allopurinol, phenytoin, ifosfamide, gentamicin, zoledronate, or any combination thereof.

In some embodiments, the agent is a glucose.

In some embodiments, the agent is a microorganism.

In some embodiments, the microorganism is a bacteria, a virus, a fungi, a protozoa, or a helminth.

In some embodiments, the agent is an inflammation stimulator.

In some embodiments, the conditioning step is reducing oxygen to the three-dimensional, engineered, biological renal tubule model.

In some embodiments, the conditioning step is applying radiation to the three-dimensional, engineered, biological renal tubule model.

In some embodiments, the conditioning step is caused by a diabetic condition.

In some embodiments, the diabetic condition is type 2 diabetes.

In some embodiments, the conditioning step is applying a high concentration of glucose, high blood pressure, or any combination thereof.

In some embodiments, the conditioning step is causing a renal lesion.

In some embodiments, the conditioning step is applying a carcinogen.

In some embodiments, the conditioning step is causing inflammation.

In some embodiments, the conditioning step is reducing blood supply to the three-dimensional, engineered, biological renal tubule model.

In some embodiments, the conditioning step is applying changes to a mitochondria.

In some embodiments, the conditioning step is changing cell morphology.

In some embodiments, the conditioning step is a hyperproliferation.

In some embodiments, the conditioning step is an epigenetic modification.

In some embodiments, the conditioning step is depositing crystals.

In some embodiments, the crystals is one or more of the following: cholesterol crystals, cholesterol monosodium urate, calcium oxalate, calcium phosphate hydroxyapatite, 2,8-dihydroxyadenine, uromodulin, myoglobin-uromodulin, indinavir, acyclovir, a polymyxin (e.g., polysporin, neosporin, polymyxin B, or polymyxin E), sulfadiazine, cysteine, uric acid, or magnesium ammonium phosphate.

In some embodiments, the conditioning step is an accumulation of proteins, salts, or other precipitous matter.

In some embodiments, the desired renal tubule disorder is an acute renal disorder.

In some embodiments, the desired renal tubule disorder is a chronic renal disorder.

In some embodiments, the desired renal tubule disorder is a renal cancer.

In some embodiments, the acute renal disorder arises from a chronic renal disorder.

BRIEF DESCRIPTION OF THE DRAWINGS

FIG. 1A is a schematic diagram showing a multicellular interstitial layer underlying a basement membrane that supports an epithelial monolayer. FIG. 1B is a macroscopic view of 3D PT tissues positioned on TRANSWELL inserts in a 24-well plate.

FIG. 2A depicts a micrograph of an H&E stain showing fully cellular tissue and organization of interstitial and epithelial layers. FIG. 2B depicts a micrograph of Gomori's trichrome stain showing deposition of collagen throughout the tissue. FIG. 2C depicts a micrograph showing the interstitial layer demonstrating extensive endothelial cell-lined networks (CD31). FIG. 2D depicts a micrograph showing that renal proximal tubule epithelial cells (RPTEC) form a monolayer and express cytokeratin 18. FIG. 2E depicts a micrograph showing that a collagen IV-rich basement membrane underlies the epithelial cells and E-cadherin localizes to tight junctions between the cells. FIG. 2F depicts a micrograph showing that $Na^+K^+$ ATPase localizes to the basolateral membrane of RPTEC.

FIG. 3A is a graph showing the metabolic activity of 3D tissues assessed by reduction of ALAMARBLUE. Data shown represent the relative fluorescence over time. FIG. 3B is a graph showing GGT function in 3D PT tissues or 3D interstitium-only tissues. Data shown represent the standard deviation of the average GGT activity in mIU/ml calculated from a standard curve. Data shown is the mean of duplicate measurements from at least 9 independent tissue samples plus or minus the standard error of the mean.

FIG. 4A is a bar graph showing expression levels of ACE in supernatant and lysates from 3D PT tissues cultured 4 or 14 days. FIG. 4B is a bar graph showing detection of angiotensin II following ACE-mediated conversion of exogenous angiotensin I. Data shown is the mean of duplicate measurements from 3 independent tissue samples plus or minus the standard error of the mean.

FIG. 5A shows 3D PT tissues stained with antibodies against SGLT2 after 14 days in culture. FIG. 5B shows results when tissues were assessed for retention of the non-metabolizable glucose analog 2-DG in a colorimetric assay in the presence or absence of the glucose uptake inducer insulin or the SGLT2 inhibitor canalgliflozin (Cana). Starved tissues are indicated. Data shown is the mean of triplicate measurements across 6 independent tissue samples plus or minus the standard error of the mean. * indicates $p<0.05$ between the groups compared by one-way ANOVA.

FIG. 6A shows 3D PT tissues stained with antibodies against P-gp after 14 days in culture. Tissues were also exposed to 5 µM zosuquidar alone (FIG. 6B), 10 µM rhodamine 123 (FIG. 6C), or rhodamine 123+zosuquidar for 2 h (FIG. 6D). Tissues were snap fixed, cryosectioned, and all tissues were imaged at the same exposure time. FIG. 6E depicts a graph showing fluorescence intensity quantified in FIGS. 6B-6D. Data shown represents the mean of duplicate measurements from at least 6 independent tissue samples plus or minus the standard error of the mean. * indicates $p<0.05$ between the groups as compared by one-way ANOVA.

FIG. 7A is a graph showing overall tissue viability measured by ALAMARBLUE metabolism. Data shown is indicative of duplicate measurements from 3 individual tissues. * indicates $p<0.05$ compared to vehicle control by one-way ANOVA and Dunnett's post-test. FIG. 7B is a graph showing epithelial viability assessed by GGT activity. Data shown is the mean of duplicate measurements from 3 independent tissue samples plus or minus the standard error of the mean. * indicates $p<0.05$ compared to vehicle control by one-way ANOVA and Dunnett's post-test.

FIG. 8A depicts ALAMARBLUE analysis of overall tissue metabolic activity. FIG. 8B depicts GGT activity as a measure of epithelial-specific function. FIG. 8C depicts daily LDH release as a measure of toxicity. For each graph, data shown represents the mean of duplicate measurements from 3 independent tissue samples plus or minus the standard error of the mean. * indicates $p<0.05$ between groups compared as assessed by one-way or two-way ANOVA. In FIG. 8C, black * indicates $p<0.05$ compared to between groups being compared. Colored stars indicate $p<0.05$ for condition compared to vehicle.

FIG. 11A depicts relative expression levels of P-gp, BCRP, megalin, cubilin, SGLT2, OAT1, OAT3, OCT2 and MATE1 for 4 different commercially available sources of primary RPTEC. FIGS. 11B-11E depict representative micrographs of commercially available primary RPTEC.

FIGS. 12A-12D are micrographs showing the histological characterization of EXVIVE kidney tissues. FIG. 12A depicts the cell morphology of untreated tissue at 20× magnification after 28 days. FIG. 12B depicts the cell morphology of tissue treated with 10 g/L glucose after 28 days (14 days cultured and 14 days treated) at 20× magnification. FIG. 12C depicts the cell morphology of untreated tissue at 40× magnification after 28 days. FIG. 12D depicts the cell morphology of tissue treated with 10 g/L glucose after 28 days at 40× magnification. Glycogenated nuclei in the epithelial layer are shown by the arrows in FIGS. 12B and 12D. The insert in FIG. 12D is a magnified view of the cell indicated by the rightmost arrow in the figure.

FIG. 13A depicts the cell morphology of untreated tissue. FIG. 13B depicts the cell morphology of tissue treated with a nephrotoxic agent under lower magnification. FIG. 13C depicts the cell morphology of tissue treated with a nephrotoxic agent under higher magnification. The arrows in FIGS. 13B and 13C indicate calcium oxalate deposits in the tissue.

FIG. 14A depict the viability of the EXVIVE Human Kidney Tissue Treated with TGFβ. FIG. 14B depict the epithelial cell functions in the EXVIVE Human Kidney Tissue Treated with TGFβ.

FIGS. 16A-16E are micrographs that show in the EXVIVE Human Kidney Tissue treated with TGFβ, TGFβ induces tissue thickening and increased extracellular matrix deposition. FIG. 16A is a micrograph of the control vehicle. FIG. 16B is a micrograph of EXVIVE Human Kidney Tissue treated with 0.37 ng/mL TGFβ. FIG. 16C is a micrograph of EXVIVE Human Kidney Tissue treated with 1.1 ng/mL TGFβ. FIG. 16D is a micrograph of EXVIVE Human Kidney Tissue treated with 3.3 ng/mL TGFβ. FIG. 16E is a micrograph of EXVIVE Human Kidney Tissue treated with 10 ng/mL TGFβ.

Figure 18A:
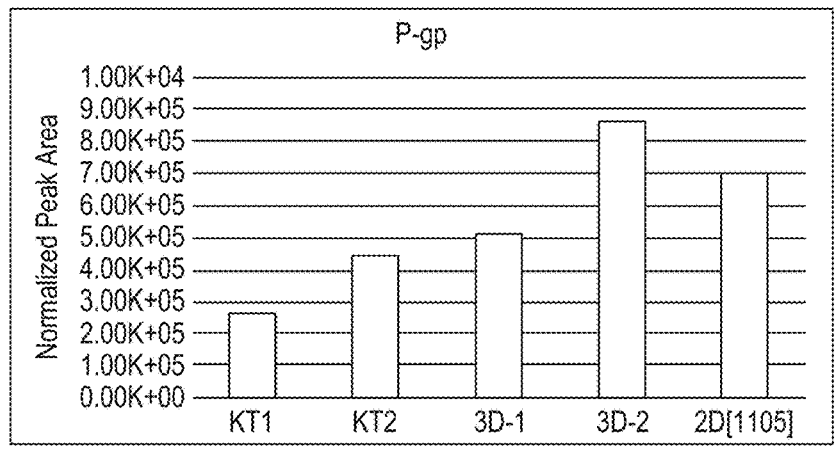
FIG. 18A-I are graphs that show human renal cortex samples (KT1 and KT2), EXVIVE Human Kidney Tissue (3D-1 and 3D-2), and plated 2D RPTEC cells (2D RPTEC lot 1105) analyzed for transporter expression by LC-MS/MS: for P-gp expression (FIG. 18A); for MATE1 expression (FIG. 18B); for OAT2 expression (FIG. 18C); for OAT1 expression (FIG. 18D); for MATE2 expression (FIG. 18E)
Figure 18B:
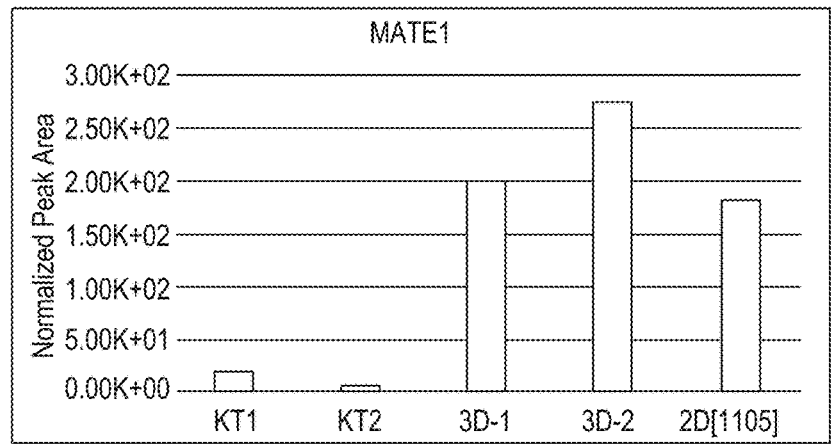
Figure 18C:
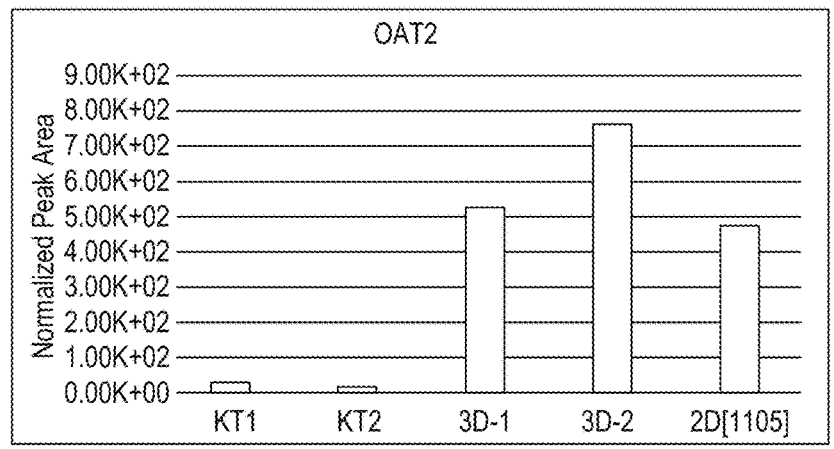
Figure 18D:
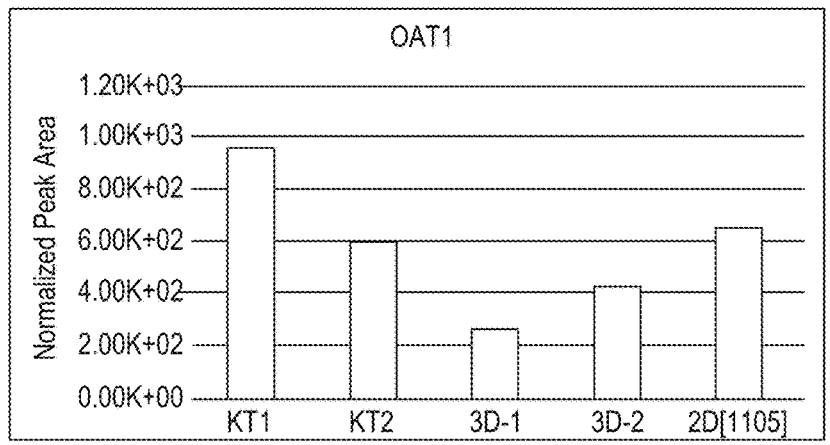
Figure 18E:
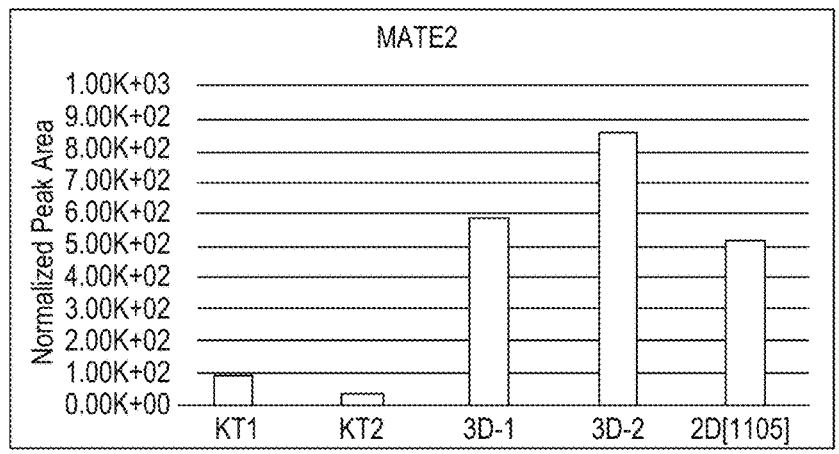
Figure 18F:
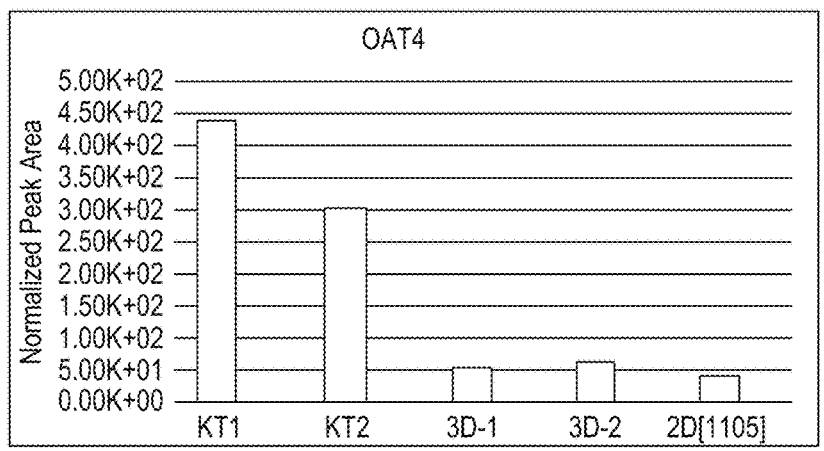
Figure 18G:
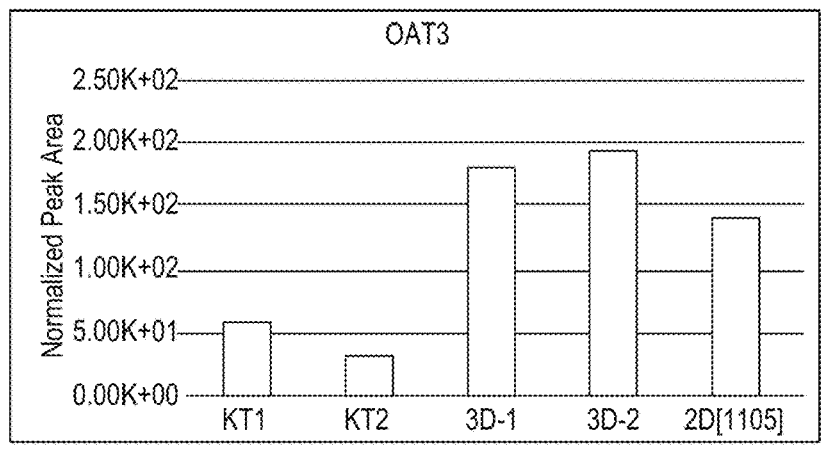
Figure 18H:
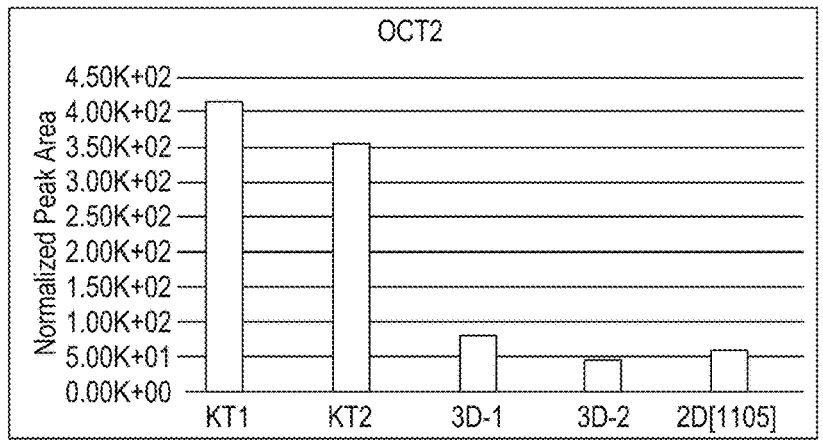
Figure 18I:
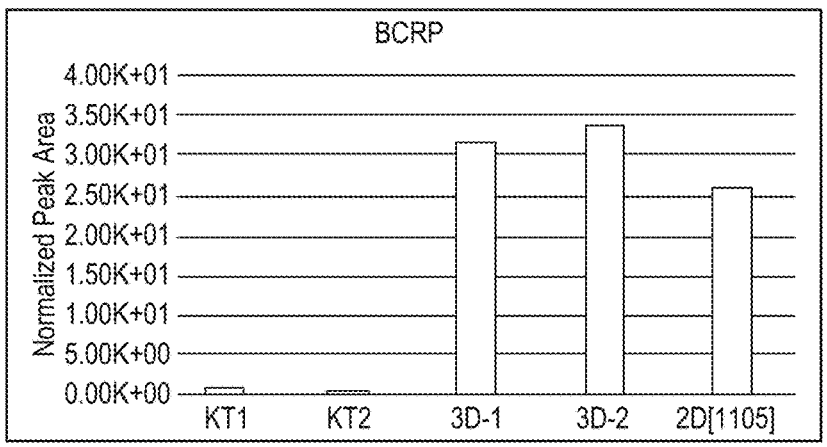

for OAT4 expression (FIG. 18F); for OAT3 expression (FIG. 18G); for OCT2 expression (FIG. 18H); and for BCRP expression (FIG. 18I).

DETAILED DESCRIPTION OF THE INVENTION

Certain Definitions

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

As used herein, "about" means±10% of the recited value. For example, about 10 includes 9-11.

As used herein, "array" means a scientific tool including an association of multiple elements spatially arranged to allow a plurality of tests to be performed on a sample, one or more tests to be performed on a plurality of samples, or both. In some embodiments, a plurality of the renal tubule models are configured to form an array. In some embodiments, the arrays are adapted for, or compatible with, screening methods and devices, including those associated with medium- or high-throughput screening. In further embodiments, an array allows a plurality of tests to be performed simultaneously. In further embodiments, an array allows a plurality of samples to be tested simultaneously. In some embodiments, the arrays are cellular microarrays. In further embodiments, a cellular microarray is a laboratory tool that allows for the multiplex interrogation of living cells on the surface of a solid support. In other embodiments, the arrays are tissue microarrays. In further embodiments, tissue microarrays include a plurality of separate tissues or tissue samples assembled in an array to allow the performance of multiple biochemical, metabolic, molecular, or histological analyses (Murphy et al., 2013). In some embodiments, the array is present in the wells of a microtiter plate.

As used herein, "assay" means a procedure for testing or measuring the presence or activity of a substance (e.g., a chemical, molecule, biochemical, protein, hormone, or drug, etc.) in an organic or biologic sample (e.g., cell aggregate, tissue, organ, organism, etc.).

As used herein, "basement membrane" means an extracellular matrix which may comprise collagen IV, laminin-entactin/nidogen complexes, and proteoglycans (Paulsson, 1992).

As used herein, "biocompatible membrane" means a membrane that is not toxic to tissue.

As used herein, "bio-ink" means a liquid, semi-solid, or solid composition for use in bioprinting. In some embodiments, bio-ink comprises cell solutions, cell aggregates, cell-comprising gels, multicellular bodies, or tissues. In some embodiments, the bio-ink additionally comprises non-cellular materials that provide specific biomechanical properties that enable bioprinting. In some embodiments, the bio-ink comprises an extrusion compound. In some cases, the extrusion compound is engineered to be removed after the bioprinting process. In other embodiments, at least some portion of the extrusion compound remains entrained with the cells post-printing and is not removed. An interstitial bio-ink comprises at least one cell of interstitial origin such as a fibroblast, mesenchymal cell, or pluripotent cells induced to have interstitial characteristics. An epithelial bio-ink comprises at least one epithelial cell type including cells of the proximal tubule.

As used herein, "bioprinting" means utilizing three-dimensional, precise deposition of cells (e.g., cell solutions, cell-containing gels, cell suspensions, cell concentrations, multicellular aggregates, multicellular bodies, etc.) via methodology that is compatible with an automated or semi-automated, computer-aided, three-dimensional prototyping device (e.g., a bioprinter). Suitable bioprinters include the NOVOGEN BIOPRINTER from Organovo, Inc. (San Diego, CA) and those described in U.S. Pat. No. 9,149,952 and U.S. Publ Appl. Nos. 2015/0093932, 2015/0004273, and 2015/0037445.

As used herein, "fibrotic tissue" refers to renal interstitial tissue that has undergone fibrosis (Farris and Colvin, 2012). Fibrosis may include both quantitative and qualitative changes to the renal interstitium and may involve multiple extracellular components as well as various cell types, including, but not limited to, fibroblasts, fibrocytes, lymphocytes, monocytes, macrophages, dendritic cells, mast cells, endothelial cells, and tubular epithelial cells (Zeisberg and Kalluri, 2015; Farris and Colvin, 2012).

As used herein, "layer" means an association of cells in X and Y planes that is one or multiple cells thick. In some embodiments, the renal tubules describe herein include one layer. In other embodiments, the renal tubules describe herein include a plurality of layers. In various embodiments, a layer forms a contiguous, substantially contiguous, or non-contiguous sheet of cells. In some embodiments, each layer of renal tubule described herein comprises multiple cells in the X, Y, and Z axes.

As used herein, "polarized" means spatially asymmetric (Bryant and Mostov, 2008).

As used herein, "scaffold" refers to synthetic scaffolds such as polymer scaffolds and porous hydrogels, non-synthetic scaffolds such as pre-formed extracellular matrix layers, dead cell layers, and decellularized tissues, and any other type of pre-formed scaffold that is integral to the physical structure of the engineered tissue and not able to be removed from the tissue without damage/destruction of said tissue. In further embodiments, decellularized tissue scaffolds include decellularized native tissues or decellularized cellular material generated by cultured cells in any manner; for example, cell layers that are allowed to die or are decellularized, leaving behind the extracellular matrix (ECM) they produced while living. The term "scaffoldless," therefore, is intended to imply that pre-formed scaffold is not an integral part of the engineered tissue at the time of use, either having been removed or remaining as an inert component of the engineered tissue. "Scaffoldless" is used interchangeably with "scaffold-free" and "free of preformed scaffold."

As used herein a "subject" is an organism of any mammalian species including but not limited to humans, primates, apes, monkey, dogs, cats, mice, rats, rabbits, pigs, horses and others. A subject can be any mammalian species alive or dead. Subject includes recently deceased subjects or biopsy samples taken from a living subject.

As used herein "therapeutic substance" means any molecule, biologic, compound or composition that is approved to treat a disease, under investigation to treat a disease, or that elicits a biological response such as changes in DNA, RNA, peptide, polypeptide or protein.

As used herein, "tissue" means an aggregate of cells.

As used herein "viable" means that at least 50% of the cells are alive. In other embodiments, viable cells are at least 60%, 70%, 80%, 90%, 95%, 97% or more of cells in a bio-ink or tissue layer as determined by at least one test of viability. Tests for viability are known in the art, and include the ALAMARBLUE Assay performed according to the manufacturer's protocol (Thermo Fisher, Carlsbad, CA).

Composition of the Renal Tubule Model

In some embodiments, the cells within the tissues are organized spatially to recapitulate the laminar architecture of the tubule-interstitial tissue interface; a polarized tubular epithelium is present on top of a layer of renal interstitial tissue that includes an endothelial cell-based microvascular network. Specialized cells, such as EPO-producing cells, are optionally included within the peritubular spaces. In some embodiments, the epithelium possesses or generates brush borders.

In particular, non-limiting embodiments, the engineered renal tissues described herein comprise two major parts: 1) an interstitial layer composed of adult renal fibroblasts and human umbilical vein endothelial cells (HUVEC); and 2) a polarized epithelial monolayer composed of either normal human renal proximal tubule epithelial cells (RPTEC), Madin-Darby canine kidney cells (MDCK), rat primary RPTEC cells, and/or immortalized RPTEC cells, wherein immortalization is optionally achieved through genetic manipulation of hTERT to form hTERT-immortalized RPTEC cells. The cells are deposited using the Organovo NOVOGEN BIOPRINTER in such a way that the epithelial layer is apical to the interstitial layer (see FIG. 1A). Structures are created by spatially-controlled deposition of cells mixed with a thermo-responsive hydrogel that degrades over time (NOVOGEL 2.0) combined with deposition of aerosolized cellular materials by compressed gas propulsion (inkjet spray). In this embodiment, the two layers together model the wall of a renal distal tubule. This configuration is critical for modeling in vivo tissues and predicting native tissue responses. Response of the epithelial layer is predictive of native tissue response to drugs, chemicals, or biological agents, and may provide information relative to toxicity or efficacy. The interstitial layer is critical for proper functioning of the epithelium and serves as a model for native tissue fibrosis, in particular renal tubulointerstitial fibrosis.

In a particular embodiment, an interstitial layer is bioprinted, using continuous deposition techniques. In this embodiment, an epithelial layer is bioprinted, using ink-jet deposition techniques onto the interstitial layer. A substantially contiguous layer of epithelium is consistent with in vivo tissues and is critical to replicate a physiologically relevant architecture. Ink-jet deposition techniques provide the ability to deposit one or more thin layers of epithelial cells onto the potentially irregular surface of the interstitial layer. In such embodiments, ink-jet deposition of the epithelial layer is optionally performed immediately after bioprinting of the interstitial layer or after the interstitial layer has been allowed to mature.

In some embodiments, the cells are bioprinted. In further embodiments, the bioprinted cells are cohered to form the engineered renal tubule models. In still further embodiments, the engineered renal tubule models are free or substantially free of pre-formed scaffold at the time of fabrication or the time of use. In some cases, bioprinting allows fabrication of tissues that mimic the appropriate cellularity of native tissue.

In some embodiments, the three-dimensional, engineered renal tubule models described herein are distinguished from tissues fabricated by prior technologies by virtue of the fact that they are three-dimensional, free of pre-formed scaffolds, consist essentially of cells, and/or have a high cell density (e.g., greater than 30% cellular, greater than 40% cellular, greater than 50% cellular, greater than 60% cellular, greater than 70% cellular, greater than 80% cellular, greater than 90% cellular, or greater than 95% cellular).

In some embodiments, the three-dimensional, engineered renal tubule models described herein are distinguished from native (e.g., non-engineered) tissues by virtue of the fact that they are non-innervated (e.g., substantially free of nervous tissue), substantially free of mature vasculature, and/or substantially free of blood components. For example, in various embodiments, the three-dimensional, engineered renal tubule models are free of plasma, red blood cells, platelets, and the like and/or endogenously-generated plasma, red blood cells, platelets, and the like. In certain embodiments, the engineered renal tubule model lacks immune cells such as T cell, B cells, macrophages, dendritic cells, basophils, mast cells or eosinophils. In some embodiments, the model is not tubular in shape like a naturally occurring renal proximal tubule, but is planar or sheet-like, this advantageously allows for in vitro assays and analysis. In some embodiments, the fibroblasts are not of renal origin. In some embodiments, the endothelial cells are not of renal origin. In some embodiments, the epithelial cells are not of human origin. In certain embodiments, the engineered renal tubule model lacks undifferentiated cells. In certain embodiments, the engineered renal tubule model lacks undifferentiated renal cells. In some embodiments, the three-dimensional, engineered renal tubule models described herein are distinguished from native renal tubule tissues in that they are flat or substantially planar. In certain embodiments, the three-dimensional, engineered renal tubule models described herein possess functional improvements over native renal tubule tissues; one example is high viability after a sustained amount of time in culture up to at least 7, 10 or 27 days in culture. In some embodiments, the cells used in the renal tubule model are transformed or immortalized. In some embodiments, the cells used in the renal tubule model are transgenic and contain protein fusions with fluorescent proteins, like EGFP, GFP, RFP, YFP, or CFP. In some embodiments, the cells used in the renal tubule model are transgenic and contain reporter constructs with fluorescent proteins; like EGFP, GFP, RFP, YFP, GFP; or luminescent proteins like firefly or renilla luciferase. In certain embodiments, any of the cells contain a deletion or insertion of 1, 2, 3, 4, 5, 6, 7, 8, 9, 10 genes or more. In some embodiments, the 3D renal tubule models are chimeras, wherein at least one cell is form a different mammalian species than any other cell of the 3D renal tubule model. In some embodiments, the 3D renal tubule models are chimeras, wherein at least one cell is form a different human donor than any other cell of the 3D renal tubule model.

Cellular Inputs

In some embodiments, the engineered tissues, arrays, and methods described herein include a plurality of cell types. In some embodiments, the renal tubule models comprise a layer of interstitial tissue comprising mammalian fibroblasts and mammalian endothelial cells. In various embodiments, suitable endothelial cells are derived from human umbilical vein (HUVEC), human primary, human kidney, or from directed differentiation of induced pluripotent stem cells (iPS) or human embryonic stem cells (hES). In some embodiments, the fibroblasts are renal interstitial fibroblasts. In various embodiments, suitable renal interstitial fibroblasts are derived from primary cells isolated from human kidney. In some embodiments, the fibroblasts are dermal or vascular in origin. In some embodiments, one or more of the cellular components are derived from a non-human mammal. In some embodiments, the interstitial tissue comprises tumor cells or cancer cells. In some embodiments, the layer of interstitial tissue is substantially a monolayer. In some embodiments, the layer of interstitial tissue comprises a monolayer over 95% of its surface area. In some embodiments, the layer of interstitial tissue comprises a monolayer over 90% of its surface area. In some embodiments, the layer of interstitial tissue comprises a monolayer over 80% of its surface area. In some embodiments, the layer of interstitial tissue is greater than 1 cell thick. In some embodiments, the layer of interstitial tissue is greater than 2 cells thick. In some embodiments, the layer of interstitial tissue is greater than 3 cells thick. In some embodiments, the layer of interstitial tissue is greater than 4 cells thick. In some embodiments, the layer of interstitial tissue is greater than 5 cells thick. In some embodiments, the layer of interstitial tissue is greater than 10 cells thick. In some embodiments, the layer of interstitial tissue is greater than 20 cells thick. In some embodiments, the layer of interstitial tissue is greater than 50 cells thick. In some embodiments, the layer of interstitial tissue is greater than 100 cells thick. In some embodiments, the layer of interstitial tissue is 2-100 cells thick. In some embodiments, the layer of interstitial tissue is greater than 20 µm thick. In some embodiments, the layer of interstitial tissue is greater than 30 um thick. In some embodiments, the layer of interstitial tissue is greater than 40 µm thick. In some embodiments, the layer of interstitial tissue is greater than 50 µm thick. In some embodiments, the layer of interstitial tissue is greater than 100 µm thick. In some embodiments, the layer of interstitial tissue is greater than 200 µm thick. In some embodiments, the layer of interstitial tissue is greater than 500 µm thick. In some embodiments, the layer of interstitial tissue is greater than 600 µm thick. In some embodiments, the layer of interstitial tissue is greater than 1000 µm thick. In some embodiments, the layer of interstitial tissue is 20 µm-1000 µm thick. In some embodiments, the layer of interstitial tissue is less than 20 µm thick. In some embodiments, the layer of interstitial tissue is less than 30 µm thick. In some embodiments, the layer of interstitial tissue is less than 40 m thick. In some embodiments, the layer of interstitial tissue is less than 50 µm thick. In some embodiments, the layer of interstitial tissue is less than 100 µm thick. In some embodiments, the layer of interstitial tissue is less than 200 µm thick. In some embodiments, the layer of interstitial tissue is less than 500 µm thick. In some embodiments, the layer of interstitial tissue is less than 600 µm thick. In some embodiments, the layer of interstitial tissue is less than 1000 µm thick.

In some embodiments, the renal tubule models comprise a layer of epithelial tissue comprising mammalian epithelial cells. In further embodiments, the epithelial cells are renal tubular epithelial cells (e.g., proximal tubule epithelial cells). In still further embodiments, suitable renal tubular epithelial cells are primary isolates or cells derived from the directed differentiation of stem cells (induced pluripotent stem cell (iPS)-derived and/or human embryonic stem cell (hES)-derived). In some embodiments, the renal tubular epithelial cells are Madin-Darby canine kidney (MDCK) cells. In some embodiments, the renal tubular epithelial cells are immortalized human cells. In other embodiments, the renal tubular epithelial cells are immortalized cells such as hTERT-RPTEC cells, HK-2 cells, LLC-PK1 cells, or OK cells. In some embodiments, the epithelial cells are derived from a non-human mammal such as, for example, rat, mouse, pig, or primate. In some embodiments, the layer of epithelial tissue consists essentially of renal tubule epithelial cells. In some embodiments, the layer of epithelial tissue consists essentially of primary renal tubule epithelial cells. In some embodiments, the layer of epithelial tissue consists essentially of renal proximal tubule epithelial cells. In some embodiments, the layer of epithelial tissue consists essentially of primary renal proximal tubule epithelial cells. In some embodiments, the layer of renal epithelial tissue is substantially a monolayer. In some embodiments, renal tubular epithelial cells are the only cells present in the layer of renal epithelial tissue. In some embodiments, the layer of epithelial tissue comprises tumor cells. In some embodiments, the layer of epithelial tissue comprises renal cell carcinoma cells. In some embodiments, the layer of epithelial tissue comprises a monolayer over 95% of its surface area. In some embodiments, the layer of epithelial tissue comprises a monolayer over 90% of its surface area. In some embodiments, the layer of epithelial tissue comprises a monolayer over 80% of its surface area. In some embodiments, the layer of epithelial tissue is greater than 1 cell thick. In some embodiments, the layer of epithelial tissue is greater than 2 cells thick. In some embodiments, the layer of epithelial tissue is greater than 3 cells thick. In some embodiments, the layer of epithelial tissue is greater than 4 cells thick. In some embodiments, the layer of epithelial tissue is greater than 5 cells thick. In some embodiments, the layer of epithelial tissue is greater than 10 cells thick. In some embodiments, the layer of epithelial tissue is greater than 20 cells thick. In some embodiments, the layer of epithelial tissue is greater than 50 cells thick. In some embodiments, the layer of epithelial tissue is greater than 100 cells thick. In some embodiments, the layer of epithelial tissue is 2-100 cells thick. In some embodiments, the layer of epithelial tissue is greater than 20 µm thick. In some embodiments, the layer of epithelial tissue is greater than 30 µm thick. In some embodiments, the layer of epithelial tissue is greater than 40 µm thick. In some embodiments, the layer of epithelial tissue is greater than 50 µm thick. In some embodiments, the layer of epithelial tissue is greater than 100 µm thick. In some embodiments, the layer of epithelial tissue is greater than 200 µm thick. In some embodiments, the layer of epithelial tissue is greater than 500 µm thick. In some embodiments, the layer of interstitial tissue is greater than 600 µm thick. In some embodiments, the layer of epithelial tissue is greater than 1000 µm thick. In some embodiments, the layer of epithelial tissue is 20-1000 µm thick. In some embodiments, the layer of epithelial tissue is less than 1000 µm thick. In some embodiments, the layer of interstitial tissue is less than 600 µm thick. In some embodiments, the layer of epithelial tissue is less than 500 µm thick. In some embodiments, the layer of epithelial tissue is less than 200 µm thick. In some embodiments, the layer of epithelial tissue is less than 100 µm thick. In some embodiments, the layer of epithelial tissue is less than 50 µm thick. In some embodiments, the layer of epithelial tissue is less than 40 µm thick. In some embodiments, the layer of epithelial tissue is less than 30 µm thick. In some embodiments, the layer of epithelial tissue is less than 20 µm thick.

Optionally, the renal tubule models comprise other cell types (e.g., EPO-producing cells, immune cells, etc.). In some embodiments, the immune cells are T cells. In some embodiments, the immune cells are B cells. In some embodiments, the immune cells are NK cells. In some embodiments, the immune cells are dendritic cells. In some embodiments, the immune cells are macrophage cells.

A wide range of cell ratios are suitable. In some embodiments, the epithelial layer comprises, consists of, or consists essentially of proximal tubule epithelial cells. In some embodiments, the fibroblasts and endothelial cells are the only cells present in the layer of renal interstitial tissue. In some embodiments, the layer of renal interstitial tissue further comprises fibrotic tissue. In some embodiments, the interstitial layer comprises, consists of, or consists essentially of fibroblasts and endothelial cells in specific ratios. Suitable proportions of fibroblasts include, by way of non-limiting examples, about 5, 10, 15, 20, 25, 30, 35, 40, 45, 50, 55, 60, 65, 70, 75, 80, 85, 90, and 95% fibroblasts, including increments therein. Suitable proportions of endothelial cells include, by way of non-limiting examples, about 5, 10, 15, 20, 25, 30, 35, 40, 45, 50, 55, 60, 65, 70, 75, 80, 85, 90, and 95% endothelial cells, including increments therein. In certain embodiments, the interstitial layer comprises, consists essentially of, or consists of a specified ratio of fibroblast to endothelial cells. In certain embodiments, the ratio of fibroblast to endothelial cells is at least 5:95, 10:90, 15:85, 20:80, 25:75, 30:70, 35:65, 40:60, 45:65, 50:50, 55:45, 60:40, 65:35, 70:30, 75:25, 80:20, 85:15, 90:10 or 95:5, including increments therein. In certain embodiments, the ratio of fibroblast to endothelial cells is 5:95 to 95:5. In certain embodiments, the ratio of fibroblast to endothelial cells is no more than 5:95, 10:90, 15:85, 20:80, 25:75, 30:70, 35:65, 40:60, 45:65, 50:50, 55:45, 60:40, 65:35, 70:30, 75:25, 80:20, 85:15, 90:10 or 95:5, including increments therein. In certain embodiments, the ratio of fibroblast to endothelial cells is about 50:50. In certain embodiments, the ratio of fibroblast to endothelial cells is from about 60:40 to about 40:60.

A wide range of cell concentrations are suitable for bio-inks. Bio-inks are suitably prepared for continuous deposition bioprinting techniques with concentrations of cells including, by way of non-limiting examples, about 1, 2, 3, 4, 5, 6, 7, 8, 9, 10, 20, 30, 40, 50, 60, 70, 80, 90, 100, 110, 120, 130, 140, 150, 160, 170, 180, 190, 200, 225, 250, 275, 300, or more, million cells per milliliter of bio-ink. In a particular embodiment, bio-ink prepared for continuous deposition bioprinting comprises about 100-200 million cells/mL. Bio-inks are suitably prepared for ink-jet deposition bioprinting techniques with concentrations of cells including, by way of non-limiting examples, about 0.25, 0.5, 1, 2, 3, 5, 10, 15 or more, million cells per milliliter of bio-ink. In a particular embodiment, bio-ink prepared for ink-jet deposition bioprinting comprises about 1-5 million cells/mL. In a particular embodiment, bio-ink prepared for ink-jet deposition bioprinting comprises about 1-4 million cells/mL. In a particular embodiment, bio-ink prepared for ink-jet deposition bioprinting comprises about 1-3 million cells/mL. In a particular embodiment, bio-ink prepared for ink-jet deposition bioprinting comprises about 1-2 million cells/mL.

In certain embodiments, the renal interstitial bio-ink comprises between 50 million and 1 billion cells per milliliter. In certain embodiments, the renal interstitial bio-ink comprises between 50 million and 900 million cells per milliliter. In certain embodiments, the renal interstitial bio-ink comprises between 50 million and 800 million cells per milliliter. In certain embodiments, the renal interstitial bio-ink comprises between 50 million and 700 million cells per milliliter. In certain embodiments, the renal interstitial bio-ink comprises between 50 million and 600 million cells per milliliter. In certain embodiments, the renal interstitial bio-ink comprises between 50 million and 500 million cells per milliliter. In certain embodiments, the renal interstitial bio-ink comprises between 50 million and 400 million cells per milliliter. In certain embodiments, the renal interstitial bio-ink comprises between 50 million and 300 million cells per milliliter. In certain embodiments, the renal interstitial bio-ink comprises between 50 million and 200 million cells per milliliter. In certain embodiments, the renal interstitial bio-ink comprises between 75 million and 600 million cells per milliliter. In certain embodiments, the renal interstitial bio-ink comprises between 100 million and 600 million cells per milliliter. In certain embodiments, the renal interstitial bio-ink comprises between 100 million and 500 million cells per milliliter. In certain embodiments, the renal interstitial bio-ink comprises between 100 million and 400 million cells per milliliter. In certain embodiments, the renal interstitial bio-ink comprises between 100 million and 300 million cells per milliliter. In certain embodiments, the renal interstitial bio-ink comprises between 100 million and 200 million cells per milliliter. In certain embodiments, the renal interstitial bio-ink comprises between 100 million and 150 million cells per milliliter.

In certain embodiments, the renal epithelial bio-ink comprises between 0.25 million and 5 million cells per milliliter. In certain embodiments, the renal epithelial bio-ink comprises between 0.25 million and 4 million cells per milliliter. In certain embodiments, the renal epithelial bio-ink comprises between 0.25 million and 3 million cells per milliliter. In certain embodiments, the renal epithelial bio-ink comprises between 0.25 million and 2 million cells per milliliter. In certain embodiments, the renal epithelial bio-ink comprises between 0.25 million and 1 million cells per milliliter. In certain embodiments, the renal epithelial bio-ink comprises between 0.5 million and 5 million cells per milliliter. In certain embodiments, the renal epithelial bio-ink comprises between 0.5 million and 4 million cells per milliliter. In certain embodiments, the renal epithelial bio-ink comprises between 0.5 million and 3 million cells per milliliter. In certain embodiments, the renal epithelial bio-ink comprises between 0.5 million and 2 million cells per milliliter. In certain embodiments, the renal epithelial bio-ink comprises between 0.5 million and 1 million cells per milliliter. In certain embodiments, the renal epithelial bio-ink comprises between 1 million and 5 million cells per milliliter. In certain embodiments, the renal epithelial bio-ink comprises between 1 million and 4 million cells per milliliter. In certain embodiments, the renal epithelial bio-ink comprises between 1 million and 3 million cells per milliliter. In certain embodiments, the renal epithelial bio-ink comprises between 1 million and 2 million cells per milliliter.

In certain embodiments, the density of the epithelial bio-ink is less than the density of the interstitial bio-ink. In certain embodiments, the ratio of the density of the interstitial bio-ink to the density of the epithelial bio-ink is about 300:1; about 275:1; about 250:1; about 225:1; about 200:1; about 175:1; about 150:1, about 125:1; about 100:1, about 75:1 or about 50:1. In certain embodiments, the ratio of the density of the interstitial bio-ink to the density of the epithelial bio-ink ranges from about 300:1 to about 50:1. In certain embodiments, the ratio of the density of the interstitial bio-ink to the density of the epithelial bio-ink ranges from about 250:1 to about 75:1. In certain embodiments, the ratio of the density of the interstitial bio-ink to the density of the epithelial bio-ink ranges from about 200:1 to about 75:1. In certain embodiments, the ratio of the density of the interstitial bio-ink to the density of the epithelial bio-ink ranges from about 150:1 to about 75:1. In certain embodiments, the ratio of the density of the interstitial bio-ink to the density of the epithelial bio-ink ranges from about 125:1 to about 75:1.

In certain embodiments, the bio-ink is a viscous liquid. In certain embodiments, the bio-ink is a semi-solid. In certain embodiments, the bio-ink is a solid. In certain embodiments, the viscosity of the bio-ink is greater than 100 centipoise. In certain embodiments, the viscosity of the bio-ink is greater than 200 centipoise. In certain embodiments, the viscosity of the bio-ink is greater than 500 centipoise. In certain embodiments, the viscosity of the bio-ink is greater than 1,000 centipoise. In certain embodiments, the viscosity of the bio-ink is greater than 2,000 centipoise. In certain embodiments, the viscosity of the bio-ink is greater than 5,000 centipoise. In certain embodiments, the viscosity of the bio-ink is greater than 10,000 centipoise. In certain embodiments, the viscosity of the bio-ink is greater than 20,000 centipoise. In certain embodiments, the viscosity of the bio-ink is greater than 50,000 centipoise. In certain embodiments, the viscosity of the bio-ink is greater than 100,000 centipoise. In certain embodiments, the viscosity of the bio-ink is less than 100 centipoise. In certain embodiments, the viscosity of the bio-ink is less than 200 centipoise. In certain embodiments, the viscosity of the bio-ink is less than 500 centipoise. In certain embodiments, the viscosity of the bio-ink is less than 1,000 centipoise. In certain embodiments, the viscosity of the bio-ink is less than 2,000 centipoise. In certain embodiments, the viscosity of the bio-ink is less than 5,000 centipoise. In certain embodiments, the viscosity of the bio-ink is less than 10,000 centipoise. In certain embodiments, the viscosity of the bio-ink is less than 20,000 centipoise. In certain embodiments, the viscosity of the bio-ink is less than 50,000 centipoise. In certain embodiments, the viscosity of the bio-ink is less than 100,000 centipoise. In certain embodiments, the viscosity of the bio-ink is 100-100,000 centipoise.

Architectural Features of the Renal Tubule Model

The renal tubule models of the present disclosure can be architecturally arranged in many configurations. In certain embodiments, the epithelial tissue and interstitial tissue layers are separate architecturally distinct layers that are in direct contact or separated by 1, 2, 3, 4, 5, 6, 7, 8, 9, 10, 15, 20 μm or more, including increments therein. In certain embodiments, the separation is due to the secretion and deposition of extracellular matrix between the two layers, which for the purposes of this disclosure is considered contact. In normal physiological tissue cells and cell layers are polarized to have an apical (lumen facing) surface and a basolateral surface, which faces other cells or tissue matrix. For the purposes of the renal tubule models disclosed herein the basolateral surface refers to a surface that faces another cell, an extracellular matrix or the surface of a biocompatible membrane or culture vessel. For the purposes of the renal tubule models disclosed herein the apical surface refers to a surface that faces away from the surface of a biocompatible membrane or culture vessel. In some embodiments, the renal tubular epithelial cells are polarized. In some embodiments, the layer of renal interstitial tissue possesses an apical and basolateral surface.

In some embodiments, the renal tubule model further comprises a biocompatible membrane. In certain embodiments, the basolateral surface of the interstitial tissue layer is the surface attached to a biocompatible membrane or culture vessel; and the apical surface of the interstitial tissue layer is the surface not attached to a biocompatible membrane or culture vessel. In certain embodiments, the epithelial tissue layer is deposited onto and forms a layer on the apical surface of the interstitial tissue layer, thus forming two architecturally distinct layers. In certain embodiments, the epithelial tissue and interstitial tissue layers are in continuous contact. In certain embodiments, between 99%-100% of the epithelial tissue layer is in continuous contact with the interstitial tissue layer. In certain embodiments, between 95%-100% of the epithelial tissue layer is in continuous contact with the interstitial tissue layer. In certain embodiments, between 90%-100% of the epithelial tissue layer is in continuous contact with the interstitial tissue layer. In certain embodiments, 50-99% of the epithelial tissue layer is in continuous contact with the interstitial tissue layer. In certain embodiments, between 80%-100% of the epithelial tissue layer is in continuous contact with the interstitial tissue layer. In certain embodiments, between 70%-100% of the epithelial tissue layer is in continuous contact with the interstitial tissue layer. In certain embodiments, between 60%-100% of the epithelial tissue layer is in continuous contact with the interstitial tissue layer. In certain embodiments, between 50%-100% of the epithelial tissue layer is in continuous contact with the interstitial tissue layer. In certain embodiments, less than 99% of the epithelial tissue layer is in continuous contact with the interstitial tissue layer. In certain embodiments, less than 98% of the epithelial tissue layer is in continuous contact with the interstitial tissue layer. In certain embodiments, less than 97% of the epithelial tissue layer is in continuous contact with the interstitial tissue layer. In certain embodiments, less than 95% of the epithelial tissue layer is in continuous contact with the interstitial tissue layer. In certain embodiments, less than 90% of the epithelial tissue layer is in continuous contact with the interstitial tissue layer. In certain embodiments, less than 80% of the epithelial tissue layer is in continuous contact with the interstitial tissue layer. In certain embodiments, the epithelial tissue layer completely covers the apical surface of the interstitial tissue layer. In certain embodiments, the epithelial tissue layer covers between 99%-100% of the apical surface of the interstitial tissue layer. In certain embodiments, the epithelial tissue layer covers between 95%-100% of the apical surface of the interstitial tissue layer. In certain embodiments, the epithelial tissue layer covers between 90%-100% of the apical surface of the interstitial tissue layer. In certain embodiments, the epithelial tissue layer covers between 80%-100% of the apical surface of the interstitial tissue layer. In certain embodiments, the epithelial tissue layer covers between 70%-100% of the apical surface of the interstitial tissue layer. In certain embodiments, the epithelial tissue layer covers between 60%-100% of the apical surface of the interstitial tissue layer. In certain embodiments, the epithelial tissue layer covers between 50%-100% of the apical surface of the interstitial tissue layer. In certain embodiments, the epithelial tissue layer covers less than 99% of the apical surface of the interstitial tissue layer. In certain embodiments, the epithelial tissue layer covers less than 98% of the apical surface of the interstitial tissue layer. In certain embodiments, the epithelial tissue layer covers less than 97% of the apical surface of the interstitial tissue layer. In certain embodiments, the epithelial tissue layer covers less than 95% of the apical surface of the interstitial tissue layer. In certain embodiments, the epithelial tissue layer covers less than 90% of the apical surface of the interstitial tissue layer. In certain embodiments, the epithelial tissue layer covers less than 80% of the apical surface of the interstitial tissue layer. In certain embodiments, the epithelial tissue layer covers less than 70% of the apical surface of the interstitial tissue layer. In certain embodiments, the epithelial tissue layer covers 50-99% of the apical surface of the interstitial tissue layer.

Architecture of the Epithelial Tissue Layer

Normally an epithelial tissue cell forms tight junctions with neighboring cells. The tight junctions are marked by the transmembrane protein family the cadherins. One of these, E-cadherin, is especially prominent at tight junctions in renal tissue, and marks their formation. In certain embodiments, the epithelial tissue layer consists of cells that form tight junctions. In certain embodiments, substantially all cells in the epithelial tissue layer form a tight junction with at least one neighboring cell. In certain embodiments, between 99%-100% of cells in the epithelial tissue layer form a tight junction with at least one other cell. In certain embodiments, between 95%-100% of cells in the epithelial tissue layer form a tight junction with at least one other cell. In certain embodiments, between 90%-100% of cells in the epithelial tissue layer form a tight junction with at least one other cell. In certain embodiments, between 80%-100% of cells in the epithelial tissue layer form a tight junction with at least one other cell. In certain embodiments, between 70%-100% of cells in the epithelial tissue layer form a tight junction with at least one other cell. In certain embodiments, between 60%-100% of cells in the epithelial tissue layer form a tight junction with at least one other cell. In certain embodiments, between 50%-100% of cells in the epithelial tissue layer form a tight junction with at least one other cell. In certain embodiments, 50-99% of cells in the epithelial tissue layer form a tight junction with at least one other cell.

Viability and Density of the Cell Layers

An advantage of bioprinting by the methods of this disclosure is that cells can be printed at high density and high viability. In certain embodiments, the density of the interstitial cell layer is greater than $1\times10^6$ cells per mL. In certain embodiments, the density of the interstitial cell layer is at least $5\times10^6$ cells per mL. In certain embodiments, the density of the interstitial cell layer is at least $10\times10^6$ cells per mL. In certain embodiments, the density of the interstitial cell layer is at least $20\times10^6$ cells per mL. In certain embodiments, the density of the interstitial cell layer is at least $50\times10^6$ cells per mL. In certain embodiments, the density of the interstitial cell layer is at least $100\times10^6$ cells per mL. In certain embodiments, the density of the interstitial cell layer is at least $200\times10^6$ cells per mL. In certain embodiments, the density of the interstitial cell layer is at least $500\times10^6$ cells per mL. In certain embodiments, the density of the interstitial cell layer is between about $100\times10^6$ cells per mL and about $900\times10^6$ cells per mL. In certain embodiments, the density of the interstitial cell layer is between about $100\times10^6$ cells per mL and about $700\times10^6$ cells per mL. In certain embodiments, the density of the interstitial cell layer is between about $100\times10^6$ cells per mL and about $600\times10^6$ cells per mL. In certain embodiments, the density of the interstitial cell layer is between about $100\times10^6$ cells per mL and about $500\times10^6$ cells per mL. In certain embodiments, the density of the interstitial cell layer is between about $100\times10^6$ cells per mL and about $300\times10^6$ cells per mL. In certain embodiments, the density of the interstitial cell layer is between about $100\times10^6$ cells per mL and about $200\times10^6$ cells per mL. In certain embodiments, the layer of renal interstitial tissue or layer of renal epithelial tissue is between 70%-100% living cells by volume. In certain embodiments, the viability of the interstitial tissue layer is greater than 99% living cells by volume. In certain embodiments, the viability of the interstitial tissue layer is greater than 95% living cells by volume. In certain embodiments, the viability of the interstitial tissue layer is greater than 90% living cells by volume. In certain embodiments, the viability of the interstitial tissue layer is greater than 80% living cells by volume. In certain embodiments, the viability of the interstitial tissue layer is greater than 70% living cells by volume. In certain embodiments, the viability of the interstitial tissue layer is greater than 60% living cells by volume. In certain embodiments, the viability of the interstitial tissue layer is greater than 50% living cells by volume. In certain embodiments, the viability of the interstitial tissue layer is 50-99% living cells by volume. In certain embodiments, this viability is maintained for at least 8, 12, 24, 48, 72, 96, or more hours post printing. In certain embodiments, this viability is maintained for at least 1, 2, 3, 4, 5, 6, 7, 8, 9, 10, 11, 12, 13, 14, 21, or more days post printing. In certain embodiments, the density of the epithelial cell layer is at least $1\times10^5$ cells per mL. In certain embodiments, the density of the epithelial cell layer is at least $2\times10^5$ cells per mL. In certain embodiments, the density of the epithelial cell layer is at least $5\times10^5$ cells per mL. In certain embodiments, the density of the epithelial cell layer is at least $1\times10^6$ cells per mL. In certain embodiments, the density of the epithelial cell layer is at least $5\times10^6$ cells per mL. In certain embodiments, the density of the epithelial cell layer is at least $10\times10^6$ cells per mL. In certain embodiments, the density of the epithelial cell layer is at least $20\times10^6$ cells per mL. In certain embodiments, the density of the epithelial cell layer is at least $50\times10^6$ cells per mL. In certain embodiments, the density of the epithelial cell layer is at least $100\times10^6$ cells per mL. In certain embodiments, the density of the epithelial cell layer is at least $200\times10^6$ cells per mL. In certain embodiments, the density of the epithelial cell layer is at least $500\times10^6$ cells per mL. In certain embodiments, the density of the epithelial cell layer is less than $1\times10^5$ cells per mL. In certain embodiments, the density of the epithelial cell layer is less than $2\times10^5$ cells per mL. In certain embodiments, the density of the epithelial cell layer is less than $5\times10^5$ cells per mL. In certain embodiments, the density of the epithelial cell layer is less than $1\times10^66$ cells per mL. In certain embodiments, the density of the epithelial cell layer is less than $5\times10^6$ cells per mL. In certain embodiments, the density of the epithelial cell layer is less than $10\times10^6$ cells per mL. In certain embodiments, the density of the epithelial cell layer is $10\times10^6$ cells per mL. In certain embodiments, the viability of the epithelial tissue layer is greater than 99% living cells by volume. In certain embodiments, the viability of the epithelial tissue layer is greater than 95% living cells by volume. In certain embodiments, the viability of the epithelial tissue layer is greater than 90% living cells by volume. In certain embodiments, the viability of the epithelial tissue layer is greater than 80% living cells by volume. In certain embodiments, the viability of the epithelial tissue layer is greater than 70% living cells by volume. In certain embodiments, the viability of the epithelial tissue layer is greater than 60% living cells by volume. In certain embodiments, the viability of the epithelial tissue layer is greater than 50% living cells by volume. In certain embodiments, the viability of the epithelial tissue layer is 50-99% living cells by volume. In certain embodiments, this viability is maintained for at least 8, 12, 24, 48, 72, or 96 hours post-printing. In certain embodiments, this viability is maintained for at least 1, 2, 3, 4, 5, 6, 7, 8, 9, 10, 11, 12, 13, or 14 days post-printing.

Uniformity of Tissue Architecture

One advantage of bioprinting using the methods of this disclosure is the high degree of uniformity achieved by the process that is reflected in the corresponding tissue. In certain embodiments, the thickness of the renal tubule model is substantially uniform. In certain embodiments, between 99%-100% of the renal tubule model is within 10% plus or minus of the overall mean thickness of the renal tubule model. In certain embodiments, between 95%-100% of the renal tubule model is within 10% plus or minus of the overall mean thickness of the renal tubule model. In certain embodiments, between 90%-100% of the renal tubule model is within 10% plus or minus of the overall mean thickness of the renal tubule model. In certain embodiments, between 80%-100% of the renal tubule model is within 10% plus or minus of the overall mean thickness of the renal tubule model. In certain embodiments, between 70%-100% of the renal tubule model is within 10% plus or minus of the overall mean thickness of the renal tubule model. In certain embodiments, between 99%-100% of the renal tubule model is within 20% plus or minus of the overall mean thickness of the renal tubule model. In certain embodiments, between 95%-100% of the renal tubule model is within 20% plus or minus of the overall mean thickness of the renal tubule model. In certain embodiments, between 90%-100% of the renal tubule model is within 20% plus or minus of the overall mean thickness of the renal tubule model. In certain embodiments, between 80%-100% of the renal tubule model is within 20% plus or minus of the overall mean thickness of the renal tubule model. In certain embodiments, between 70%-100% of the renal tubule model is within 20% plus or minus of the overall mean thickness of the renal tubule model. After treatment with a potential toxic agent, the renal tubule model may become less uniform.

Non-Cellular Components of Bio-Inks and Cell Layers

Often cells or bio-inks that are bioprinted contain excipients or extrusion compounds that improve their suitability for bioprinting. Examples of extrusion compounds include, but are not limited to gels, hydrogels, peptide hydrogels, amino acid-based gels, surfactant polyols (e.g., PLURONIC F-127 or PF-127), thermo-responsive polymers, hyaluronates, alginates, extracellular matrix components (and derivatives thereof), collagens, gelatin, other biocompatible natural or synthetic polymers, nanofibers, and self-assembling nanofibers. In some embodiments, the extrusion compound contains a synthetic polymer. In some embodiments, the extrusion compound contains a non-synthetic polymer that is not normally associated with mammalian tissues. In some embodiments, extrusion compounds are removed after bioprinting by physical, chemical, or enzymatic means. In some embodiments, the bio-inks of the present disclosure contain 1% or more extrusion compound by weight. In some embodiments, the renal tubule models of the present disclosure contain more than 1% extrusion compound by weight. In some embodiments, the bio-inks of the present disclosure contain less than 5% extrusion compound by weight. In some embodiments, the bio-inks of the present disclosure contain between 0%-2% extrusion compound by weight. In some embodiments, the bio-inks of the present disclosure contain less than 1% extrusion compound by weight. In some embodiments, the renal tubule models of the present disclosure contain between 0%-5% extrusion compound by weight. In some embodiments, the renal tubule models of the present disclosure contain less than 2% extrusion compound by weight.

In some embodiments, the renal tubule models of the present disclosure contain less than 1% extrusion compound by weight. In some embodiments, the epithelial bio-ink is free from hydrogel. In some embodiments, the epithelial bio-ink is free from extrusion compound. In some embodiments, the epithelial bio-ink is free from synthetic polymers that are used as excipient or extrusion compounds. In some embodiments, the renal tubule model is free from synthetic polymers that are used as excipient or extrusion compounds. In some embodiments, the epithelial cell layer is free from synthetic polymers that are used as excipient or extrusion compounds. In some embodiments, the interstitial cell layer is free from synthetic polymers that are used as excipient or extrusion compounds.

Print Surfaces

Provided herein are renal tubule models that are attached to a biocompatible surface. In certain embodiments, the interstitial tissue layer is printed onto a biocompatible surface. In certain embodiments, the biocompatible surface is a membrane with a pore size of 0.4 μm to 10 μm. In certain embodiments, the biocompatible surface has a pore size of about 1 μm. In certain embodiments, the biocompatible surface is coated with a composition to improve cell adherence or viability. In certain embodiments, the renal tubule modules are printed into 6-well, 12-well, 24-well, 48-well, 96-well, or 384-well plates. In certain embodiments, the renal tubule modules are printed into tissue culture plates with diameters of 60, 100 or 150 mm or more. In certain embodiments, the renal tubule modules are printed into tissue culture flasks or onto microfluidic chips. In certain embodiments, the renal tubule models are printed into/onto TRANSWELL inserts.

Process for Production of Renal Tubule Models

This disclosure supports methods and processes for fabricating renal tubule models. In certain embodiments, the product of a three-dimensional, engineered, biological renal tubule model is produced by the process of bioprinting. In certain embodiments, at least one constituent of the product of a three-dimensional, engineered, biological renal tubule model is produced by the process of bioprinting. In certain embodiments, the process of fabricating a three-dimensional, engineered, biological renal tubule model, comprises: preparing a renal interstitial bio-ink, the interstitial bio-ink comprising a plurality of interstitial cell types, the interstitial cell types comprising renal fibroblasts and endothelial cells; preparing a renal epithelial bio-ink, the epithelial bio-ink comprising renal tubular epithelial cells; depositing the renal interstitial bio-ink and the renal epithelial bio-ink such that the renal epithelial bio-ink forms a layer on at least one surface of the layer of renal interstitial bio-ink; and maturing the deposited bio-ink in a cell culture media to allow the cells to cohere to form the three-dimensional, engineered, biological renal tubule model. In certain embodiments, the renal interstitial tissue bio-ink forms a renal interstitial tissue layer with an apical and basolateral surface. In certain embodiments, the renal epithelial bio-ink is deposited in contact with the apical surface of the renal interstitial tissue layer. In certain embodiments, the renal epithelial bio-ink consists essentially of renal tubular epithelial cells. In certain embodiments, the renal epithelial bio-ink consists essentially of primary renal tubular epithelial cells. In certain embodiments, the primary renal tubular epithelial cells are isolated from a subject with a disease that affects kidney function. In certain embodiments, the primary renal tubular epithelial cells are isolated from a subject with polycystic kidney disease. In certain embodiments, the primary renal tubular epithelial cells are isolated from a subject with diabetes mellitus type II. In certain embodiments, the renal epithelial bio-ink comprises renal cell carcinoma cells. In certain embodiments, the renal epithelial bio-ink is deposited in a monolayer. In certain embodiments, the renal interstitial tissue bio-ink is deposited in a monolayer. In certain embodiments, the layer of renal epithelial tissue is deposited in continuous contact with the layer of renal interstitial tissue. In certain embodiments, the renal epithelial bio-ink forms a layer that covers between 50%-100% of the apical surface of the layer of renal interstitial tissue. In certain embodiments, the renal epithelial bio-ink forms a layer that covers between 70%-100% of the apical surface of the layer of renal interstitial tissue. In certain embodiments, the renal epithelial bio-ink forms a layer that covers between 90%-100% of the apical surface of the layer of renal interstitial tissue. In certain embodiments, the renal epithelial bio-ink forms a layer that covers 50-90% the apical surface of the layer of renal interstitial tissue. In certain embodiments, at least 50% of renal epithelial cells of the renal epithelial layer form tight junctions with other renal epithelial cells. In certain embodiments, at least 70% of renal epithelial cells of the renal epithelial layer form tight junctions with other renal epithelial cells. In certain embodiments, at least 90% of renal epithelial cells of the renal epithelial layer form tight junctions with other renal epithelial cells. In certain embodiments, 50-90% of renal epithelial cells of the renal epithelial layer form tight junctions with other renal epithelial cells. In certain embodiments, the renal tubule model is between 50 and 500 µm thick. In certain embodiments, the renal tubule model is about 100 µm thick. In certain embodiments, the renal epithelial bio-ink further comprises an extrusion compound. In certain embodiments, the fibroblasts and endothelial cells are present in the renal interstitial bio-ink at a ratio of about 95:5 to about 5:95 fibroblasts to endothelial cells. In certain embodiments, the fibroblasts and endothelial cells are present in the renal interstitial bio-ink at a ratio of about 75:25 to about 25:75 fibroblasts to endothelial cells. In certain embodiments, the fibroblasts and endothelial cells are present in the renal interstitial bio-ink at a ratio of about 60:40 to about 40:60 fibroblasts to endothelial cells. In certain embodiments, the fibroblasts and endothelial cells are present in the renal interstitial bio-ink at a ratio of about 50:50 fibroblasts to endothelial cells. In certain embodiments, the renal interstitial bio-ink further comprises secretory cells. In certain embodiments, the renal interstitial bio-ink further comprises immune cells. In certain embodiments, the renal interstitial bio-ink further comprises an extrusion compound. In certain embodiments, the renal interstitial bio-ink comprises glomerular cells. In certain embodiments, the model is fabricated substantially free of pre-formed scaffold. In certain embodiments, the renal fibroblasts, endothelial cells, and renal tubular epithelial cells are mammalian cells. In certain embodiments, either of the renal interstitial bio-ink or renal epithelial bio-ink forms a planar layer after deposition. In certain embodiments, the renal tubule model is of a uniform thickness. In certain embodiments, the renal interstitial bio-ink is deposited onto a biocompatible membrane. In certain embodiments, the renal interstitial bio-ink is deposited onto a biocompatible membrane with a pore size greater than 0.4 µm. In certain embodiments, the renal interstitial bio-ink is deposited onto a biocompatible membrane with a pore size of about 1 um. In certain embodiments, the three-dimensional, engineered, biological renal tubule models are deposited to form an array. In certain embodiments, the three-dimensional, engineered, biological renal tubule models are deposited to form an array configured to allow between about 20 µm and about 100 µm of space between each renal tubule model. In certain embodiments, the renal interstitial bio-ink is between 30%-100% living cells by volume. In certain embodiments, the renal interstitial bio-ink is between 70%-100% living cells by volume. In certain embodiments, the renal interstitial bio-ink is between 90%-100% living cells by volume. In certain embodiments, the renal interstitial bio-ink is deposited by extrusion bioprinting. In certain embodiments, the renal epithelial bio-ink is deposited by ink-jet bioprinting. In certain embodiments, the renal interstitial bio-ink is not deposited by ink-jet bioprinting. In certain embodiments, any layer of the renal tubule model is viable in in vitro culture in culture after 3 days. In certain embodiments, any layer of the renal tubule model is viable in in vitro culture after 10 days.

In certain embodiments, the 3D renal tubule models disclosed herein are produced by an additive manufacturing process. The additive manufacturing process for 3D tubule models herein allows customized fabrication of 3D renal tubule models for in vitro purposes. This is significant in that the tissues are fabricated due to a user specified design. In certain embodiments, the 3D renal tubule models contain only the cells that the user specifies. In certain embodiments, the 3D renal tubule models contain only the cell types that the user specifies. In certain embodiments, the 3D renal tubule models contain only the number of cells or concentration of cells that the user specifies. In certain embodiments, the 3D renal tubule models contain cells that have been treated with a small molecule, therapeutic molecule, or therapeutic substance before or during fabrication. A therapeutic molecule or substance being any molecule intended to treat a disease or elicit a biological response. In certain embodiments, the 3D renal tubule models contain biocompatible or tissue culture plastics, biocompatible synthetic polymers, cross linkable gels, reversibly cross-linked gels and other non-cellular constituents.

Maturation of Renal Tubule Models

In certain embodiments, the renal tubule models of the present disclosure are matured for a certain amount of time after bioprinting. In certain embodiments, the models are matured for 1-24 hours before use, for example, at least 1, 2, 3, 4, 5, 6, 7, 8, 9, 10, 11, 12, 16, 18, 24 hours or more before use. In certain embodiments, the models are matured for 1-30 days before use, for example, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 days or more before use. In some embodiments, shipment or transfer of the tissues is a use. In certain embodiments, the interstitial layer of the renal tubule model of the present disclosure is matured for a certain amount of time after bioprinting before addition of the epithelial layer. In certain embodiments, the interstitial layer is matured for 1-24 hours before use, for example, at least 1, 2, 3, 4, 5, 6, 7, 8, 9, 10, 11, 12, 16, 18, 24 hours or more before use. In certain embodiments, the interstitial layer is matured for 1-30 days before use, for example, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 days or more before use. In some embodiments, shipment or transfer of the tissues is a use. In some embodiments, the epithelial layer is bioprinted onto the interstitial layer within 1-24 hours after bioprinting of the interstitial layer, for example, 1, 2, 3, 4, 5, 6, 7, 8, 9, 10, 11, 12, 16, 18, 24 hours after bioprinting of the interstitial layer. In some embodiments, shipment or transfer of the tissues is a use. In some embodiments, the epithelial layer is bioprinted onto the interstitial layer within 1-30 days after bioprinting of the interstitial layer, for example 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 days after bioprinting of the interstitial layer.

Uses of the Renal Tubule Models

The renal tubule models described herein can be utilized for multiple applications. In one embodiment, the tissue barrier can be utilized for toxicology and ADME applications. In one embodiment, functional features of the renal tubule models include establishment of a barrier and demonstrating permeability/absorption (as evidenced by TEER and Lucifer yellow permeability). These features allow for permeability kinetics (Papp) and influx/efflux (ab, ba) studies. In another embodiment, the investigation of active transport and metabolism via key transporters and metabolic enzymes respectively can be performed via well-based assays or through detection of substrates and their metabolites by mass spectrometry. These same techniques can be used to assess the mechanism of active transport and metabolism of various drugs and applied compounds. Transport kinetic, efflux rate and the permeability coefficient of a test substance could therefore be utilized for correlation to FDA-recommended reference drugs. Through barrier function and permeability kinetics, the renal tubules may be used to predict whether there is active transport of compounds via renal transporters similar to native tissue, predict the ability of compounds to disrupt the renal barrier and/or induce renal inflammation, and/or predict the efficacy of compounds to modulate inflammation.

In some embodiments, the renal tubule models disclosed herein comprising immune cells are used in the modeling of inflammation and inflammatory diseases, as well as the impact of immune modulation on cancer. In one embodiment, the immune cells are myeloid or lymphoid cells. In another embodiment, the disease models are compared side by side to normal tissue models, e.g., renal tubule models lacking immune cells, comprising immune cells but not stimulated to activate the immune cells (quiescent), or lacking immune cells and stimulated with cytokines to mimic an immune response. In this embodiment, the renal tubule models are useful for evaluation of inflammation and immune responses. Tissue constructs comprising immune cells may also be used to study acute responses. Renal tubule models comprising immune cells may also be used to model injury and recovery including acute, subchronic, or chronic dosing of candidate pharmaceutical compounds or therapies. In another embodiment, the renal tubule models comprising immune cells are used to evaluate wound healing and fibrosis. Furthermore, the tissue constructs comprising immune cells may be used to model microbial/microbiome interactions. The 3D nature of the renal tubule models allow for enhanced observation of pathogen invasiveness and translocation. In one embodiment, the renal tubule models are treated subsequently with candidate pharmaceutical agents or treatments to reverse or control the inflammatory effects. Inflammatory signals that may be detected include the release of cytokines (e.g. IL-8, TNF-α, IL-4, IL-19, IL-13, IL-17, and/or IFN-gamma), antimicrobial peptides (e.g. beta defensin, lysozymes, and/or sIgA), endocrine products such as somatostatin, activation of inflammatory pathways (e.g. JAK/STAT, and/or NFkB), evaluation of a barrier disruption in response to inflammation (histology, TEER, Lucifer yellow, Ussing chamber, and/or other well-based assays), measuring proliferation, cytotoxicity, tissue damage, or apoptosis (Caspase 8 or Tunel) or autophagy or re-epithelialization of wounded area, and expression of key markers and receptors upregulated in response to stimulation. For any of the phenotypes described, the renal tubule models may be used to demonstrate the kinetics and magnitude of onset as well as recovery from perturbation. For example, one can dose the renal tubule models with a therapeutic agent and measure the kinetics of absorption in parallel with the kinetics of onset of tissue damage, and then remove the test agent and measure the kinetics of clearance of the molecule in the renal tubule and of recovery from damage. Analysis of these parameters may enable the prediction of appropriate dosing levels and dosing schedule for compounds entering the clinic.

In some embodiments, the renal tubule models are used in a model of a renal disorder.

In some embodiments, the renal tubule models are used in a model of a renal disorder, wherein the renal tubule models comprise:
  (a) a layer of renal interstitial tissue, the renal interstitial tissue comprising renal fibroblasts and endothelial cells; and
  (b) a layer of renal epithelial tissue, the renal epithelial tissue comprising renal tubular epithelial cells, to form the three-dimensional, engineered, biological renal tubule model; provided that the interstitial tissue comprises an interstitial bio-ink, the epithelial tissue comprises an epithelial bio-ink, and form a three-dimensional, engineered, biological renal tubule model, wherein the model manifests a phenotype characteristic of a disorder associated with the renal tubule.

In some embodiments, the renal tubule models may be used in a method of assessing the ability of a therapeutic agent to reverse, reduce, induce, or prevent a renal disorder.

Also provided is a method of assessing the ability of a candidate therapeutic agent to reverse, reduce, induce, or prevent a renal disorder, the method comprising:
  (a) contacting the renal tubule model with the candidate therapeutic agent;
  (b) determining the viability or functionality of the renal tissue cells; and
  (c) assessing the ability of the candidate therapeutic to reverse, reduce, induce, or prevent a renal disease based on the determined viability or functionality of the renal tissue cells compared to a control renal tubule model that has not been contacted with the candidate therapeutic agent.

In some embodiments, the renal tubules and arrays disclosed herein are for use in in vitro assays. In some embodiments, an "assay" is a procedure for testing or measuring the presence or activity of a substance (e.g., a chemical, molecule, biochemical, drug, etc.) in an organic or biologic sample (e.g., cell aggregate, tissue, organ, organism, etc.). In further embodiments, assays include qualitative assays and quantitative assays. In still further embodiments, a quantitative assay measures the amount of a substance such as a chemical or biomolecule in a sample.

In various embodiments, the renal tubules and arrays are for use in, by way of non-limiting example, image-based assays, measurement of secreted proteins, expression of markers, and production of proteins or mRNAs. In various further embodiments, the renal tubules and arrays are for use in assays to detect or measure one or more of: molecular binding (including radioligand binding), molecular uptake, activity (e.g., enzymatic activity and receptor activity, etc.), gene expression, protein expression, protein modifications (non-limiting examples include: phosphorylation, ubiquitination, acetylation, glycosylation, lipidation, etc.), receptor agonism, receptor antagonism, cell signaling, apoptosis, chemosensitivity, transfection, cell migration, chemotaxis, cell viability, cell proliferation, safety, efficacy, metabolism, toxicity, infectivity, and abuse liability. In various embodiments, the renal tubules are for toxicology, pharmaceutical or toxicity testing.

In some embodiments, the renal tubules and arrays are for use in immunoassays. Immunoassays include, for example, flow cytometry, high throughput or low throughput image analysis, immunoprecipitation, radio-immunoassay (RIA), enzyme-linked immunosorbent assays (ELISA), western blot, homogenous assays, such as ALPHALISA and related technologies that rely on time resolved fluorescence or fluorescence resonance energy transfer (FRET). In further embodiments, immunoassays are competitive immunoassays or noncompetitive immunoassays. In a competitive immunoassay, for example, the antigen in a sample competes with labeled antigen to bind with antibodies and the amount of labeled antigen bound to the antibody site is then measured. In a noncompetitive immunoassay (also referred to as a "sandwich assay"), for example, antigen in a sample is bound to an antibody site; subsequently, labeled antibody is bound to the antigen and the amount of labeled antibody on the site is then measured.

In some embodiments, the renal tubules and arrays are for use in ELISA. In further embodiments, an ELISA is a biochemical technique used to detect the presence of an antibody or an antigen in a sample. In ELISA, for example, at least one antibody with specificity for a particular antigen is utilized. By way of further example, a sample with an unknown amount of antigen is immobilized on a solid support (e.g., a polystyrene microtiter plate) either non-specifically (via adsorption to the surface) or specifically (via capture by another antibody specific to the same antigen, in a "sandwich" ELISA). By way of still further example, after the antigen is immobilized, the detection antibody is added, forming a complex with the antigen. The detection antibody is, for example, covalently linked to an enzyme, or is itself detected by a secondary antibody that is linked to an enzyme through bioconjugation.

For example, in some embodiments, an array, microarray, or chip of cells, multicellular aggregates, or tissues is used for drug screening or drug discovery. In further embodiments, an array, microarray, or chip of tissues is used as part of a kit for drug screening or drug discovery. In some embodiments, each renal tubule exists within a well of a biocompatible multi-well container, wherein the container is compatible with one or more automated drug screening procedures and/or devices. In further embodiments, automated drug screening procedures and/or devices include any suitable procedure or device that is computer or robot-assisted.

In further embodiments, arrays for drug screening assays or drug discovery assays are used to research or develop drugs potentially useful in any therapeutic area. In still further embodiments, suitable therapeutic areas include, by way of non-limiting examples, infectious disease, hematology, oncology, pediatrics, cardiology, central nervous system disease, neurology, gastroenterology, hepatology, urology, infertility, ophthalmology, nephrology, orthopedics, pain control, psychiatry, pulmonology, vaccines, wound healing, physiology, pharmacology, dermatology, gene therapy, toxicology, toxicity, and immunology.

In some embodiments, the renal tubules and arrays are for use in cell-based screening. In further embodiments, the cell-based screening is for one or more infectious diseases such as viral, fungal, bacterial or parasitic infection. In further embodiments, the cell-based screening is for kidney cancer, including renal cell carcinoma, juxtaglomerular cell tumor (reninoma), angiomyolipoma, renal oncocytoma, Bellini duct carcinoma, clear-cell sarcoma of the kidney, mesoblastic nephroma, Wilms' tumor, mixed epithelial stromal tumor, and transitional cell carcinoma of the renal pelvis. In further embodiments, the cell-based screening is for nephritis, including, glomerulonephritis, interstitial nephritis or tubulo-interstitial nephritis, pyelonephritis, lupus nephritis and athletic nephritis. In further embodiments, the cell-based screening is for hypertension. In further embodiments, the cell-based screening is for diabetes mellitus, type I, type II and MODY. In further embodiments, the cell-based screening is for a nephropathy, including IgA nephropathy, analgesic nephropathy, or onconephropathy. In some embodiments, the cell-based screening is for polycystic kidney disease or Xanthine oxidase deficiency. In other embodiments, the renal tubules and arrays are for use in the study of cancer initiation, progression, or metastasis. In still further embodiments, the renal tubules and arrays are for use in the study of the interaction of other cell types, such as cancer cells, pathogen-bearing cells, pathogenic cells, immune cells, blood-derived cells, or stem/progenitor cells.

In some embodiments, the constructs or arrays thereof are for use in assessing the performance of biologics, including antibodies, mammalian cells, bacteria, biologically-active proteins, hormones, etc. In other embodiments, the renal tubules or arrays thereof are useful in the study of cell-cell and cell-tissue interactions between the mammalian renal tubules comprising the construct and one or more additional cell types, including but not limited to pathogen-bearing cells, living pathogenic cells, cancer cells, immune cells, blood cells, stem/progenitor cells, or genetically-manipulated cells.

In some embodiments, the array comprises renal tubules and additional tissue constructs. In further embodiments, the renal tubule construct is in direct contact with an additional tissue construct on one or more surfaces. In still further embodiments, the renal tubule is connected to one or more additional tissues constructs or cells via a fluid path or common fluid reservoir. In still further embodiments, the liquid media that contacts the engineered renal tubule construct contains living mammalian cells such as immune cells, blood-derived cells, or tumor-derived cells. In other embodiments, the liquid media that contacts the renal tubule contains bacteria, fungi, viruses, parasites, or other pathogens.

Provided are methods of assessing the ability of a candidate therapeutic agent to reverse, reduce or prevent renal injury by a potential toxic agent comprising: contacting the potential toxic agent with a three-dimensional, engineered, bioprinted, biological renal tubule model; contacting the renal tubule model with the candidate therapeutic agent; determining the viability or functionality of the renal tubular epithelial cells; and assessing the ability of the candidate therapeutic agent to reverse, reduce or prevent renal injury by the potential toxic agent based on the determined viability or functionality of the renal tubular epithelial cells compared to a control renal tubule model that has not been contacted with the candidate therapeutic agent. In certain embodiments, the three-dimensional, engineered, bioprinted, biological renal tubule model comprises a layer of renal interstitial tissue and a layer of renal epithelial tissue. In other embodiments, the renal interstitial tissue comprises renal fibroblasts and endothelial cells, and the renal epithelial tissue comprises renal tubular epithelial cells to form the three-dimensional, engineered, biological renal tubule model; provided that the interstitial tissue comprises an interstitial bio-ink, the epithelial tissue comprises an epithelial bio-ink, and form a three-dimensional, engineered, biological renal tubule model.

In one embodiment, the fibroblasts and endothelial cells are present in a ratio of fibroblasts to endothelial cells at which the renal tubule model is planar six days post-printing. In some embodiments, the fibroblasts and endothelial cells are present in the layer of renal interstitial tissue at a ratio of about 50:50 fibroblasts to endothelial cells.

In some embodiments, the model further comprises a layer of basement membrane between the renal interstitial tissue layer and the renal epithelial tissue layer. In some embodiments, the layer of renal epithelial tissue is in continuous contact with the layer of basement membrane, and the layer of basement membrane is in continuous contact with the layer of renal interstitial tissue.

In some embodiments, the renal tubular model is at least 3 cell layers thick. In some embodiments, the renal tubular model is 2 or more cell layers thick. In some embodiments, the mean thickness of the renal tubule model is at least 50 µm. In some embodiments, the mean thickness of the renal tubule model is at least 100 µm. In some embodiments, the mean thickness of the renal tubule model is at least 200 µm. In some embodiments, the mean thickness of the renal tubule model is at least 300 µm. In some embodiments, the mean thickness of the renal tubule model is at least 400 µm. In some embodiments, the mean thickness of the renal tubule model is at least 500 µm. In some embodiments, the mean thickness of the renal tubule model is at least 600 µm. In some embodiments, the mean thickness of the renal tubule model is at least 700 µm. In some embodiments, the mean thickness of the renal tubule model is at least 800 µm. In some embodiments, the mean thickness of the renal tubule model is at least 900 µm. In some embodiments, the mean thickness of the renal tubule model is at least 1000 µm. In some embodiments, the mean thickness of the renal tubule model is between 50 µm and 1000 µm. In some embodiments, the mean thickness of the renal tubule model is between 75 µm and 1000 µm. In some embodiments, the mean thickness of the renal tubule model is between 100 µm and 1000 µm. In some embodiments, the mean thickness of the renal tubule model is between 200 µm and 1000 µm. In some embodiments, the mean thickness of the renal tubule model is between 500 µm and 1000 µm. In some embodiments, the mean thickness of the renal tubule model is between 50 µm and 500 µm. In some embodiments, the mean thickness of the renal tubule model is between 50 µm and 300 µm. In some embodiments, the mean thickness of the renal tubule model is between 50 µm and 200 µm. In some embodiments, the mean thickness of the renal tubule model is between 50 µm and 150 µm. In some embodiments, the mean thickness of the renal tubule model is between 50 µm and 125 µm. In some embodiments, the mean thickness of the renal tubule model is between 75 µm and 100 µm.

In some embodiments, the surface area of the renal tubule model is between 0.01 $cm^2$ and 0.1 $cm^2$. In some embodiments, the surface area of the renal tubule model is at least 0.01 $cm^2$. In some embodiments, the surface area of the renal tubule model is at least 0.02 $cm^2$. In some embodiments, the surface area of the renal tubule model is at least 0.03 $cm^2$. In some embodiments, the surface area of the renal tubule model is at least 0.04 $cm^2$. In some embodiments, the surface area of the renal tubule model is at least 0.05 $cm^2$. In some embodiments, the surface area of the renal tubule model is at least 0.06 $cm^2$. In some embodiments, the surface area of the renal tubule model is at least 0.07 $cm^2$. In some embodiments, the surface area of the renal tubule model is at least 0.08 $cm^2$. In some embodiments, the surface area of the renal tubule model is at least 0.09 $cm^2$. In some embodiments, the surface area of the renal tubule model is at least 0.10 $cm^2$. In some embodiments, the surface area of the renal tubule model is at least 0.11 $cm^2$. In some embodiments, the surface area of the renal tubule model is at least 0.12 $cm^2$. In some embodiments, the surface area of the renal tubule model is less than 0.5 $cm^2$. In some embodiments, the surface area of the renal tubule model is less than 0.4 $cm^2$. In some embodiments, the surface area of the renal tubule model is less than 0.3 $cm^2$. In some embodiments, the surface area of the renal tubule model is less than 0.2 $cm^2$. In some embodiments, the surface area of the renal tubule model is less than 0.1 $cm^2$.

The potential toxic agent is anything that may have an affect on the structure or function of renal tissue. In some embodiments, the potential toxic agent is a toxin, a therapeutic agent, an antimicrobial agent, a metal, or an environmental agent. In other embodiments, the potential toxic agent is an antiviral, an analgesic agent, an antidepressant agent, a diuretic agent, or a proton pump inhibitor.

In other embodiments, the potential toxic agent is a cytokine, a chemokine, a small molecule drug, a large molecule drug, a protein or a peptide.

In other embodiments, the potential toxic agent is a chemotherapeutic agent which is an aromatase inhibitor; an anti-estrogen; an anti-androgen; a gonadorelin agonist; a topoisomerase I inhibitor; a topoisomerase II inhibitor; a microtubule active agent; an alkylating agent; a retinoid, a carontenoid, or a tocopherol; a cyclooxygenase inhibitor; an MMP inhibitor; an mTOR inhibitor; an antimetabolite; a platin compound; a methionine aminopeptidase inhibitor; a bisphosphonate; an antiproliferative antibody; a heparanase inhibitor; an inhibitor of Ras oncogenic isoforms; a telomerase inhibitor; a proteasome inhibitor; a compound used in the treatment of hematologic malignancies; a Flt-3 inhibitor; an Hsp90 inhibitor; a kinesin spindle protein inhibitor; a MEK inhibitor; an antitumor antibiotic; a nitrosourea; a compound targeting/decreasing protein or lipid kinase activity, a compound targeting/decreasing protein or lipid phosphatase activity, or an anti-angiogenic compound. In other embodiments, the potential toxic agent is a chemotherapeutic agent which is daunorubicin, adriamycin, Ara-C, VP-16, teniposide, mitoxantrone, idarubicin, cisplatin, carboplatinum, PKC412, 6-mercaptopurine (6-MP), fludarabine phosphate, octreotide, SOM230, FTY720, 6-thioguanine, cladribine, 6-mercaptopurine, pentostatin, hydroxyurea, 2-hydroxy-1H-isoindole-1,3-dione derivatives, 1-(4-chloroanilino)-4-(4-pyridylmethyl)phthalazine, 1-(4-chloroanilino)-4-(4-pyridylmethyl)phthalazine succinate, angiostatin, endostatin, anthranilic acid amides, ZD4190, ZD6474, SU5416, SU6668, bevacizumab, rhuMAb, rhuFab, macugon, FLT-4 inhibitors, FLT-3 inhibitors, VEGFR-2 IgGI antibody, RPI 4610, bevacizumab, porfimer sodium, anecortave, triamcinolone, hydrocortisone, 11-α-epihydrocotisone, cortex olone, 17a-hydroxyprogesterone, corticosterone, desoxycorticosterone, testosterone, estrone, dexamethasone, fluocinolone, a plant alkaloid, a hormonal compound and/or antagonist, a biological response modifier, such as a lymphokine or interferon, an antisense oligonucleotide or oligonucleotide derivative, shRNA, siRNA, or a pharmaceutically acceptable salt thereof.

In other embodiments, the potential toxic agent is acetaminophen, lithium, acyclovir, amphotericin B, and aminoglycoside, a beta lactams, foscavir, ganciclovir, pentamidine, a quinolone, a sulfonamide, vancomycin, rifampin, adefovir, indinavir, didofovir, tenofovir, methotrexate, lansoprazole, omeprazole, pantopraxole, allopurinol, phenytoin, ifosfamide, gentamycin, or zoledronate.

In some embodiments, the potential toxic agent is radiation. In some embodiments, radiation may include X-rays, gamma rays, UV, and others. In some embodiments, radiation is used alone or in combination with another toxic agent or agents. In some embodiments, the radiation may include photon radiotherapy, particle beam radiation therapy, other types of radiotherapies, and combinations thereof.

In some embodiments, the toxic agent is dissolved in a biocompatible solvent. When the potential toxic agent is water insoluble, the potential toxic agent may be dissolved with a polar, aprotic organic solvent such as dimethyl sulfoxide (DMSO) or dimethyl formamide (DMF) and then diluted with a aqueous solution such as 9 g/L sodium chloride (saline), in distilled water, aqueous Tween, culture media, or another biocompatible solvent.

In some embodiments, the viability or functionality of the renal tubular epithelial cells is determined by measuring an indicator of metabolic activity. In some embodiments, metabolic activity may be measured by ALAMARBLUE Assay (Thermo Fisher, Carslbad, CA), lactate dehydrogenase (LDH) activity assay, or another assay. In some embodiments, the indicator of metabolic activity is resazurin reduction or tetrazolium salt reduction in the renal tubule mode compared to a control. In some embodiments, resazurin reduction is measured using the ALAMARBLUE assay (Rampersad, 2012). In some embodiments, the tetrazolium salts include 3-(4,5-dimethyl)thiazol-2-yl)-2, 5-diphenyltetrazolium bromide (MTT); sodium 3'-[1-phenylamino)-carbonyl]-3,4-tetrazolium]-bis (4-methoxy-6-nitrobenzene) sulfonic acid hydrate (XTT); 4-[3-(4-iodophenyl)-2-(4-nitrophenyl)-2H-5-tetrazolio]-1,3-benzene disulfonate, water-soluble tetrazolium salt (WST-1); and others (Rampersad, 2012).

In some embodiments, the viability or functionality of the renal tubular epithelial cells is determined by measuring lactate dehydrogenase (LDH) activity (see Example 2), gamma glutamyl-transferase (GGT) activity (see Example 2), protease activity, ATP utilization, glucose uptake activity (see Example 7), sodium-glucose co-transporter-2 (SGLT2) activity (see Example 12), or RNA expression (see Example 6) compared to a control. In some embodiments, protease activity is measured by measuring caspase activity using synthetic peptide substrates (Kumar, 2004). In some embodiments, intracellular ATP is measured using an ATP assay kit (Weng, 2015).

In other embodiments, the viability or functionality of the renal tubular epithelial cells is determined by measuring a renal transport molecule activity in the model compared to a control. In other embodiments, the transport molecule activity is excretion and/or uptake of at least one macromolecule. In other embodiments, the macromolecule is albumin. In some embodiments, albumin uptake is measured using fluorescence microscopy and cell lysate fluorescence (Ferrell, 2012).

In other embodiments, the viability or functionality of the renal tubular epithelial cells is determined by identifying regeneration of the renal tubular epithelial cells compared to a control. In one embodiment, regeneration is identified by visually inspecting the renal tubular epithelial cells and identifying an increase in the number of viable cells.

In other embodiments, the viability or functionality of the renal tubular epithelial cells is determined by measuring the trans-epithelial electrical resistance (see Example 2) or the passive permeability (see Example 2) of the renal tubule model compared to a control.

In other embodiments, the viability or functionality of the renal tubular epithelial cells is determined by measuring changes in vitamin D production, changes in angiotensin conversion (see Example 3), alterations to ion exchange, alterations to pH, alterations to acid/base balance, alterations to renal tubule barrier function (see Example 10), or alterations to the intrarenal renin/angiotensin system (RAS) (see Example 11), alterations in physiology, alterations in pathology (see Example 5), alterations to transport of molecules (see Example 12), alterations to sodium-glucose cotransporter-2 (SGLT2) activity (see Example 12), amounts of interstitial fibrotic tissue, or regeneration of the renal tubule model compared to a control.

In other embodiments, the viability or functionality of the renal tubular epithelial cells is determined by measuring amounts of interstitial fibrotic tissue compared to a control. In some embodiments, interstitial fibrotic tissue is measured using trichrome-PAS fibrosis measurement, collagen III immunohistochemistry, Sirius Red staining, or another type of assay (Farris et al., 2011). In some embodiments, the viability or functionality of the renal tubular epithelial cells is measured over time.

In some embodiments, the renal tubule model is contacted first with the potential toxic agent and then with the candidate therapeutic agent. In other embodiments, the renal tubule model is contacted first with the candidate therapeutic agent and then with the potential toxic agent. In some embodiments, the renal tubule model has been cultured in a cell culture medium prior to being contacted with the candidate therapeutic agent and the potential toxic agent. In some embodiments, the renal tubule model has been cultured for at least 3 days in the cell culture medium.

Also provided are methods of assessing the effect of an agent on renal function, the method comprising contacting the agent with a three-dimensional, engineered, bioprinted, biological renal tubule model and measuring the effect of the agent on renal function for the viability or functionality of the renal tubular epithelial cells. In some embodiments, the three-dimensional, engineered, bioprinted, biological renal tubule model comprises a layer of renal interstitial tissue, the renal interstitial tissue comprising renal fibroblasts and endothelial cells; and a layer of renal epithelial tissue, the renal epithelial tissue comprising renal tubular epithelial cells; provided that the interstitial tissue comprises an interstitial bio-ink, the epithelial tissue comprises an epithelial bio-ink, and form a three-dimensional, engineered, biological renal tubule model. In one embodiment, the fibroblasts and endothelial cells are present in a ratio of fibroblasts to endothelial cells at which the renal tubule model is planar six days post-printing.

Models of Renal Disorders

Provided are models of a renal disorder, comprising a three-dimensional, engineered, bioprinted, biological renal tubule model. In some embodiments, the three-dimensional, engineered, bioprinted, biological renal tubule models comprise a layer of renal interstitial tissue, the renal interstitial tissue comprising renal fibroblasts and/or endothelial cells; and a layer of renal epithelial tissue, the renal epithelial tissue comprising renal tubular epithelial cells; provided that the interstitial tissue comprises an interstitial bio-ink, the epithelial tissue comprises an epithelial bio-ink, and form a three-dimensional, engineered, biological renal tubule model.

In some embodiments, the renal disorder is associated with retention of lipids within the renal model. Lipid accumulation can be induced in the model by incorporation of adipocytes. In some embodiments, the renal disorder is associated with congenital abnormality, diabetes, an immune complex disease, vascular sclerosis, renal fibrosis, hypertension, arterionephrosclerosis, lupus nephritis, vascular disease, inflammation, hemolytic-uremic syndrome, obstructive nephropathy, dyslipoproteinemia, recurrent dehydration, reflux nephropathy, radiation nephropathy, atheroembolic renal disease, scleroderma, sickle cell anemia, retention of lipids, toxicant exposure, infection, ischemia, ischemia/reperfusion, a transport deficiency, a cystic disease, a crystallopathy, or a combination thereof. In some embodiments, the renal disorder may arise following an environmental exposure. In other embodiments, the renal disorder may arise as a result of a genetic or epigenetic modification. In some embodiments, the renal disorder may arise following a defect in cellular localization or activity of a transporter, enzyme, or other protein.

Acute Renal Disorders

In some embodiments, the renal disorder is an acute renal disorder.

In some embodiments, the acute renal disorder is acute tubular necrosis. Acute tubular necrosis involves the death of tubular epithelial cells that form the renal tubules of the kidneys. Acute tubular necrosis is a form of acute kidney injury that may be life-threatening.

In some embodiments, the acute renal disorder is acute interstitial nephritis. Acute interstitial nephritis is a renal lesion that causes a decline in renal function and is characterized by the infiltration and localization of inflammatory cells in the kidney interstitium. Acute interstitial nephritis is a form of acute kidney injury.

In some embodiments, the acute renal disorder is an acute kidney injury. Acute kidney injury is also called acute renal failure or acute kidney failure. Acute kidney injury is an abrupt or rapid decline in renal filtration. Acute kidney injury occurs when the kidneys suddenly become unable to filter waste products from the blood and can result in the accumulation of dangerous levels of waste.

In some embodiments, the acute kidney injury is caused by toxicant exposure, diabetes, infection, inflammation, ischemia, or ischemia/reperfusion.

In some embodiments, the acute kidney injury is caused by toxicant exposure. In some embodiments, the toxicant is an anti-infective. Anti-infectives include antibiotics, antibacterials, antifungals, and antivirals. In some embodiments, the toxicant is an antibiotic, an antibacterial, an antifungal, or an antiviral. In some embodiments, the toxicant is acetaminophen, lithium, acyclovir, amphotericin B, an aminoglycoside, a beta lactam, foscavir, ganciclovir, pentamidine, a quinolone, a sulfonamide, vancomycin, rifampin, adefovir, indinavir, didofovir, tenofovir, methotrexate, lansoprazole, omeprazole, pantopraxole, allopurinol, phenytoin, ifosfamide, gentamicin, or zoledronate.

In some embodiments, the acute kidney injury is caused by diabetes. In some embodiments, the diabetes is type 2 diabetes. In some embodiments, the diabetes is type 1 diabetes. In some embodiments, the diabetes is caused by exposure to high blood glucose and/or high blood pressure. In some embodiments, the proximal tubule injury resulting from diabetes is secondary to a decline in glomerular integrity and function, which leads to elevated glucose, proteins such as albumin, or other blood components in the filtrate. In some embodiments, the kidney injury resulting from diabetes is caused in part by exposure of the tubule to elevated levels of glucose, protein, and other blood components in the filtrate. In some embodiments, the acute kidney injury is caused by diabetic ketoacidosis. Diabetic ketoacidosis (DKA) is a life-threatening complication of diabetes (usually type 1 diabetes) characterized by hyperglycemia, hyperketonemia, and metabolic acidosis. DKA is usually triggered by insulin deficiency and hyperglycemia combined with significant physiologic stress, such as acute infection, myocardial infarction, stroke, pancreatitis, or trauma. It can also be triggered by corticosteroids, thiazide diuretics, and sympathomimetics. In some embodiments, tubular injury is further compromised by loss or compromise of microvasculature and resulting hypoxia.

In some embodiments, the acute kidney injury is caused by infection. In some embodiments, the infection is caused by a microorganism or microbe. In some embodiments, the microorganism that causes infection is a bacteria, a virus, a fungi, a protozoa, or a helminth.

In some embodiments, the acute kidney injury is caused by inflammation. In some embodiments, the inflammation is caused by a pattern recognition receptor. Pattern recognition receptors include toll-like receptors (TLRs), retinoic acid-inducible gene (RIG)-I-like receptors, NOD-like receptors, and C-type lectin receptors. In some embodiments, the inflammation is caused by a TLR, a RIG-I-like receptor, a NOD-like receptor, or a C-type lectin receptor.

In some embodiments, the acute kidney injury is caused by ischemia. Ischemia is an inadequate blood supply to an organ or part of the body. In some embodiments, the acute kidney injury is caused by reperfusion. Reperfusion is injury to the kidney caused when blood supply returns to the kidney after a period of ischemia.

In some embodiments, the acute kidney injury is a secondary condition to another disorder. In some embodiments, the acute kidney injury is caused by acute interstitial nephritis, a cystic disease, a nephropathy, a crystallopathy/nephrolithiasis, an infectious disease, exposure to a toxicant, renal cancer, or a potential toxic agent. In some embodiments, the acute kidney injury is caused by nephritis which arises from lupus, pyelonephritis, or onconephritis. In some embodiments, the acute kidney injury is caused by a genetic disorder such as polycystic disease. In some embodiments, the acute kidney injury is caused by a nephropathy such as diabetic nephropathy. In some embodiments, the acute kidney injury is caused by an infectious disease. In some embodiments, the acute kidney injury is caused by exposure to a toxicant. In some embodiments, the acute kidney injury is caused by renal cancer. In some embodiments, the acute kidney injury is caused by a potential toxic agent.

In some embodiments, the result of acute kidney injury is necrosis, apoptosis, nephritis, tubular regeneration, compensatory proliferation, epithelial-mesenchymal transition (EMT), inflammation, ischemia, reactive oxygen species, changes in the mitochondria, changes to cell morphology, changes to nuclear morphology, hyperproliferation, alterations in gene expression, secretion of biomarkers, or epigenetic modifications.

In some embodiments, the result of acute kidney injury is necrosis. In some embodiments, acute kidney injury caused by exposure to toxicants results in necrosis.

In some embodiments, the result of acute kidney injury is apoptosis. Apoptosis is the death of cells that occurs as a normal and controlled part of an organism's growth or development. In some embodiments, acute kidney injury is caused by exposure to toxicants resulting in apoptosis.

In some embodiments, the result of acute kidney injury is tubular regeneration. During tubular regeneration, renal epithelial cells undergo morphological changes, migrate, and proliferate to replace lost cells, finally resulting in physiological and functional recovery of the renal epithelium. Molecules such as vimentin, Pax-2, and neural cell adhesion molecule can be re-expressed in renal epithelial cells during recovery from acute kidney injury (Tang et al., 2015).

In some embodiment, the result of acute kidney injury is compensatory proliferation of existing tubular cells, which proliferate to repopulate the tubule when cells are lost due to damage and cell death.

In some embodiments, the result of acute kidney injury is EMT. EMT is a process by which epithelial cells lose their cell polarity and cell-cell adhesion, and gain migratory and invasive properties to become mesenchymal stem cells, which can either remain mesenchymal or differentiate back to epithelial cells. EMT can occur in wound healing, in tissue fibrosis, and in the initiation of metastasis for cancer progression.

In some embodiments, the result of acute kidney injury is inflammation. In some embodiments, acute kidney injury can be caused by inflammation. In some embodiments, the inflammation that causes or results from acute kidney injury is caused by the activation of pattern recognition receptors. In some embodiments, the inflammation that causes or results from acute kidney injury is caused by cytokines. In some embodiments, the inflammation that causes or results from acute kidney injury is caused by chemokines.

In some embodiments, the result of acute kidney injury is ischemia. In some embodiments, activation of hypoxia-inducible transcription factor (HIF) protects against ischemia. HIF has been identified as an important mechanism of cellular adaptation to low oxygen (hypoxia).

In some embodiments, the result of acute kidney injury is a change in the mitochondria. Changes in the mitochondria caused by acute kidney injury include changes in mitochondrial glutathione levels, changes in reactive oxygen species, and changes in mitochondrial morphology. In some embodiments, the result of acute kidney injury is mitochondrial impairment. Mitochondrial impairment includes loss of mitochondrial membrane potential, reduction in mitochondrial biogenesis, and a drop in ATP production (Granata et al., 2015).

In some embodiments, the result of acute kidney injury is a change to cell morphology. Changes in cell morphology caused by acute kidney injury include changes in the amount of cytoplasm and changes in the shape of the cell.

In some embodiments, such as with hyperglycemia, the result of proximal tubule cell injury is evidenced by a change in nuclear morphology. In some embodiments, the cellular injury presents as the accumulation of glycogen. In some embodiments, glycogen accumulates in the nucleus, such that the nuclei appear clear and vacuolated in standard histological stains such as H&E and Periodic Acid Shiff. In other embodiments, cellular injury is evidenced by accumulation of glycogen in the cytoplasm.

In some embodiments, the result of acute kidney injury is hyperproliferation. Hyperproliferation is an abnormally high rate of proliferation by cells by rapid division.

In some embodiments, the result of acute kidney injury is an alteration in gene expression. In some embodiments, the alteration of gene expression may lead to downstream changes in protein expression and/or function.

In some embodiments, the result of acute kidney injury is a secretion of biomarkers. Biomarkers of acute kidney injury can be components of serum or urine or can be imaging studies. In some embodiments, the biomarkers of acute kidney injury include N-acetyl-β-glucosamide, $\beta_2$-microglobulin, $\alpha_1$-microglobulin, retinol binding protein, cystatin-C, microalbumin, kidney injury molecule-1, clusterin, neutrophil gelatinase-associated lipocalin, interleukin-18, cysteine-rich protein, osteopontin, fatty acid-binding protein, sodium/hydrogen exchanger isoform, or fetuin-A (Vaidya et al., 2008).

In some embodiments, the result of acute kidney injury is an epigenetic modification. Epigenetics refers to the modulation of gene expression via post-translational modification of protein complexes which are associated with DNA but do not change the DNA sequence such as acetylation, methylation, phosphorylation, ubiquitinylation, sumoylation, carbonylation, glycosylation, and expression of microRNA (Tang et al., 2015). In some embodiments, the epigenetic modification may lead to downstream changes in protein expression and/or function.

Chronic Renal Disorder

In some embodiments, the renal disorder is a chronic renal disorder. Chronic renal disorder is also called chronic kidney disease or chronic kidney failure. In some embodiments, the chronic renal disorder is chronic kidney injury. Chronic kidney injury is the progressive deterioration of renal function.

In some embodiments, tubular flow is required to develop a relevant phenotype characteristic of a chronic renal disorder.

In some embodiments, chronic renal disorder is caused by the same mechanisms as acute renal disorder but with exposure over a longer period of time. In some embodiments, the chronic kidney injury is caused by toxicant exposure, diabetes, infection, inflammation, ischemia, crystal deposition, a genetic disorder, a cystic disease, a chronic system disorder, or a transport deficiency.

In some embodiments, the chronic kidney injury is caused by toxicant exposure. In some embodiments, the toxicant is an anti-infective. Anti-infectives include antibiotics, antibacterials, antifungals, and antiviral. In some embodiments, the toxicant is an antibiotic, an antibacterial, an antifungal, or an antiviral. In some embodiments, the toxicant is acetaminophen, lithium, acyclovir, amphotericin B, an aminoglycoside, a beta lactam, foscavir, ganciclovir, pentamidine, a quinolone, a sulfonamide, vancomycin, rifampin, adefovir, indinavir, didofovir, tenofovir, methotrexate, lansoprazole, omeprazole, pantopraxole, allopurinol, phenytoin, ifosfamide, gentamicin, or zoledronate.

In some embodiments, the chronic kidney injury is secondary to diabetes. In some embodiments, the diabetes is type 2 diabetes. In some embodiments, the diabetes is type 1 diabetes. In some embodiments, the chronic kidney disease is secondary to hypertension and vascular/glomerular injury. In some embodiments, the proximal tubule injury is secondary to a decline in glomerular integrity and function, which leads to elevated glucose, proteins such as albumin, or other blood components in the filtrate. In some embodiments, the kidney injury resulting from diabetes is caused in part by exposure of the tubule to elevated levels of glucose, protein, and other blood components in the filtrate. In some embodiments, the acute kidney injury is caused by DKA. In some embodiments, tubular injury is further compromised by loss or compromise of microvasculature and resulting hypoxia.

In some embodiments, the chronic kidney injury is caused by infection. In some embodiments, the infection is caused by a microorganism or microbe. In some embodiments, the microorganism that causes infection is a bacteria, a virus, a fungi, a protozoa, or a helminth.

In some embodiments, the chronic kidney injury is caused by inflammation. In some embodiments, the inflammation is caused by a pattern recognition receptor. Pattern recognition receptors include toll-like receptors (TLRs), retinoic acid-inducible gene (RIG)-I-like receptors, NOD-like receptors, and C-type lectin receptors. In some embodiments, the inflammation is caused by a TLR, a RIG-I-like receptor, a NOD-like receptor, or a C-type lectin receptor. In some embodiments, the inflammation that causes chronic kidney injury is caused by cytokines. In some embodiments, the inflammation that causes chronic kidney injury is caused by chemokines.

In some embodiments, the chronic kidney injury is caused by persistent ischemia.

In some embodiments, the chronic kidney injury is caused by crystal deposition. Crystal deposition in the kidney can result from different mechanisms including: (1) Crystal embolism, mostly caused by cholesterol crystals originating from atherosclerotic lesions of the aorta. These crystals can obstruct smaller arteries and arterioles and lead to ishemic kidney injury. (2) Intratubular cast formation leading to obstruction of distal tubules. (3) Diffuse crystallization with intratubular plugs and intratubular and intrastitial crystals like in oxalate nephropathy or cystinosis. (4) Pelvic stone formation at the papilla, which consist of calcium phosphate precipitates in the interstitium at the thin loop of Henle. The resulting lesion (Randall's plaque) becomes an attachment site for the precipitation of other urinary crystals that can grow to stones. (Mulay et al., 2014). In some embodiments, the crystal or particle is cholesterol monosodium urate, calcium oxalate, calcium phosphate hydroxyapatite, 2,8-dihydroxyadenine, uromodulin, myoglobin-uromodulin, indinavir, acyclovir, a polymyxin (e.g., polysporin, neosporin, polymyxin B, or polymyxin E), sulfadiazine, cysteine, uric acid, or magnesium ammonium phosphate.

In some embodiments, the chronic kidney injury is caused by a genetic disorder. In some embodiments, the genetic disorder is a cystic kidney disease, Alport's syndrome, Bartter's syndrome, cystinosis, cystinuria, hyperoxaluria, congenital nephrotic syndrome, nail-patella syndrome, primary immune glomerulonephritis, reflux nephropathy, or haemolytic uraemic syndrome. In some embodiments, the genetic disorder is a cystic kidney disease such as autosomal dominant polycystic kidney disease, autosomal recessive polycystic kidney disease, juvenile nephronophthiasis, adult nephronophthisis, medullary sponge kidney, a cystic kidney disease associated with a multiple malformation syndrome (e.g., tuberous sclerosis, Lowe's syndrome, or Von Hippel-Lindau disease).

In some embodiments, the chronic kidney injury is caused by a chronic system disorder such as diabetes, an autoimmune disease (e.g., systemic lupus erythematosus or Goodpasture's syndrome), or gout.

In some embodiments, the chronic kidney injury is caused by a transport deficiency. In some embodiments, the chronic kidney injury is caused by a glucose transport deficiency.

In some embodiments, the chronic kidney injury is caused by an accumulation of proteins, salts, or other precipitous matter.

In some embodiments, the result of chronic kidney injury is necrosis, apoptosis, nephritis, tubular regeneration, EMT, inflammation, ischemia, changes in the mitochondria, changes to cell morphology, changes to nuclear morphology, hyperproliferation, alternations in gene expression, secretion of biomarkers, epigenetic modifications, or crystal deposition.

In some embodiments, the result of chronic kidney injury is necrosis. In some embodiments, chronic kidney injury caused by exposure to toxicants results in necrosis.

In some embodiments, the result of chronic kidney injury is apoptosis. In some embodiments, chronic kidney injury caused by exposure to toxicants results in apoptosis.

In some embodiments, the result of chronic kidney injury is tubular regeneration.

In some embodiment, the result of chronic kidney injury is compensatory proliferation.

In some embodiments, the result of chronic kidney injury is EMT.

In some embodiments, the result of chronic kidney injury is inflammation. In some embodiments, chronic kidney injury can be caused by inflammation. In some embodiments, the inflammation that results from chronic kidney injury is caused by the activation of pattern recognition receptors. In some embodiments, the inflammation that results from chronic kidney injury is caused by cytokines. In some embodiments, the inflammation that results from chronic kidney injury is caused by chemokines.

In some embodiments, the result of chronic kidney injury is ischemia. In some embodiments, activation of hypoxia-inducible transcription factor (HIF) protects against ischemia.

In some embodiments, the result of chronic kidney injury is a change in the mitochondria. Changes in the mitochondria caused by chronic kidney injury include changes in mitochondrial glutathione levels, changes in reactive oxygen species, and changes in mitochondrial morphology. In some embodiments, the result of chronic kidney injury is mitochondrial impairment. Mitochondrial impairment includes loss of mitochondrial membrane potential, reduction in mitochondrial biogenesis, and a drop of ATP production (Granata et al., 2015).

In some embodiments, the result of chronic kidney injury is a change to cell morphology. Changes in cell morphology caused by chronic kidney injury include changes in the amount of cytoplasm, changes in the shape of the cell and cyst formation.

In some embodiments, the result of proximal tubule cell injury is evidenced by a change in nuclear morphology. In some embodiments, the cellular injury presents as the accumulation of glycogen. In some embodiments, glycogen accumulates in the nucleus, such that the nuclei appear clear and vacuolated in standard histological stains such as H&E and Periodic Acid Shiff. In other embodiments, cellular injury is evidenced by accumulation of glycogen in the cytoplasm.

In some embodiments, the result of chronic kidney injury is hyperproliferation.

In some embodiments, the result of chronic kidney injury is an alteration in gene expression. In some embodiments, the alteration of gene expression may lead to downstream changes in protein expression and/or function.

In some embodiments, the result of chronic kidney injury is a secretion of biomarkers. Biomarkers of chronic kidney injury can be components of serum or urine or can be imaging studies. In some embodiments, the biomarkers of chronic kidney injury include N-acetyl-β-glucosamide, $β_2$-microglubulin, $α_1$-microglobulin, retinol binding protein, cystatin-C, microalbumin, kidney injury molecule-1, clusterin, neutrophil gelatinase-associated lipocalin, interleukin-18, cysteine-rich protein, osteopontin, fatty acid-binding protein, sodium/hydrogen exchanger isoform, or fetuin-A (Vaidya et al., 2008).

In some embodiments, the result of chronic kidney injury is an epigenetic modification. Epigenetic modification include modifications to the nucleotides or DNA backbone by acetylation, methylation, phosphorylation, ubiquitinylation, sumoylation, carbonylation, glycosylation, or expression of microRNA. In some embodiments, the epigenetic modification may lead to downstream changes in protein expression and/or function.

In some embodiments, the result of chronic kidney injury is the presence of a crystal or a particle. In some embodiments, the crystal or particle is cholesterol monosodium urate, calcium oxalate, calcium phosphate hydroxyapatite, 2,8-dihydroxyadenine, uromodulin, myoglobin-uromodulin, indinavir, acyclovir, a polymyxin (e.g., polysporin, neosporin, polymyxin B, or polymyxin E), sulfadiazine, cysteine, uric acid, or magnesium ammonium phosphate.

Renal Cancer

In some embodiments, the renal disorder is a renal cancer.

In some embodiments, the renal cancer is renal cell carcinoma, transitional cell carcinoma, Wilms' tumor, or renal sarcoma. In some embodiments, the renal cancer is a renal cell carcinoma such as clear cell renal cell carcinoma, papillary renal cell carcinoma, chromophobe renal cell carcinoma, collecting duct renal cell carcinoma, multilocular cystic renal cell carcinoma, medullary carcinoma, mucinous tubular and spindle cell carcinoma, or neuroblastoma-associated renal cell carcinoma.

In some embodiments, the renal cancer is caused by protein modifications, gene mutations, gene translocations, chemical exposure, genetic dysfunction, or an epigenetic modification.

In some embodiments, the renal cancer is caused by protein modifications. In some embodiments, the protein modification is phosphorylation of a protein or truncation of a protein.

In some embodiments, the renal cancer is caused by gene mutations. In some embodiments, the gene mutation turns on an oncogene or turns off a tumor suppressor gene. In some embodiments, the gene mutation is an inherited gene mutation such as a mutation in the VHL gene, a mutation in the FH gene, a mutation in the FLCN gene, a mutation in the SDHB gene, a mutation in the SDHD gene, or a mutation in the MET oncogene. In some embodiments, the gene mutation is an acquired gene mutation such as a mutation in the tumor suppressor gene and/or oncogene caused by cancer-causing chemicals. In some embodiments, the gene mutation is an acquired gene mutation caused by a mutation to the VHL gene. In some embodiments, the alteration of gene expression may lead to downstream changes in protein expression and/or function.

In some embodiments, the renal cancer is caused by gene translocations. Gene translocation can lead to fusion between two different genes that results in a protein with altered function (i.e., BCR-ABL gene fusion).

In some embodiments, the renal cancer is caused by exposure to a chemical that leads to renal cancer.

In some embodiments, the renal cancer is caused by a genetic dysfunction. In some embodiments, the genetic dysfunction causes a mutation in the nucleotide. In some embodiments, the mutation may lead to downstream changes in protein expression and/or function.

In some embodiments, the renal cancer is caused by an epigenetic modification. Epigenetic modification includes modifications to the nucleotides or DNA backbone by acetylation, methylation, phosphorylation, ubiquitinylation, sumoylation, carbonylation, glycosylation, or expression of microRNA. In some embodiments, the epigenetic modification may lead to downstream changes in protein expression and/or function.

In some embodiments, the result of renal cancer is hyperproliferation, angiogenesis, hypoxia, or death of surrounding tissue.

In some embodiments, the result of renal cancer is hyperproliferation.

In some embodiments, the result of renal cancer is angiogenesis.

In some embodiments, the result of renal cancer is hypoxia. Tumor hypoxia is the situation where tumor cells have been deprived of oxygen. As a tumor grows, it rapidly outgrows its blood supply, leaving portions of the tumor with regions where the oxygen concentration is significantly lower than in healthy tissues.

In some embodiments, the result of renal cancer is the death of surrounding tissue.

Methods of Producing a Renal Disorder in the Renal Tubule Model

In some embodiments, a renal disorder as described herein is produced in a renal tubule model as described herein by contacting the model with a molecule such as a toxicant, or a high level of glucose to produce a renal tubule phenotype that is characteristic of the renal disorder.

In some embodiments, a renal disorder is produced in the renal tubule model by genetically modified cells in the model. In some embodiments, the genetically modified cells are modified before the model is formed. In some embodiments, the genetically modified cells are modified after the model is formed. In some embodiments, the genetic modification is a polycystic mutation in a transporter. In some embodiments, the genetic modification is made by using a retrovirus, CRISPR, viral transduction, or chemical mutagenesis. In some embodiments, the genetic modification is made in a stem cell, which is then used to fabricate the renal tubule disorder model. In some embodiments, the bio-ink includes a stem cell having the genetic modification, with the bio-ink being used to fabricate the renal tubule disorder model.

In some embodiments, the renal disorder is produced in the renal tubule model by using cells from diseased donors and using them as cell inputs. In some embodiments, cells can be isolated from donors with a specific disease and used to fabricate the renal tubule disorder model. In some embodiments, the bio-ink includes cells isolatd from donors with a specific disease, with the bio-ink being used to fabricate the renal tubule disorder model. In other embodiments, induced pluripotent stem cells can be taken from adults with a genetic dysfunction and used to fabricate the renal tubule disorder model. In some embodiments, the bio-ink includes induced pluripotent stem cells taken from adults with a genetic dysfunction, with the bio-ink being used to fabric the renal tubule disorder model.

In some embodiments, the fibroblasts, endothelial cells, and/or epithelial cells can be genetically modified prior to incorporation into the tissue or after tissue formation to induce the disease phenotype. In some embodiments, the bio-ink includes genetically modified fibroblasts, endothelial cells, epithelial cells, or other kidney cells, with the bio-ink being used to fabricate the renal tubule disorder model.

Testing the Viability or Functionality of the Renal Tubule Model

In some embodiments, the viability or functionality of the renal tubule model is determined by measuring the induction of an apoptotic pathway. In some embodiments, the viability or functionality of the renal tubule model is determined by caspase activation. In some embodiments, caspase activity is measured using synthetic peptide substrates (Kumar, 2004). In other embodiments, the viability or functionality of the renal tubule model is determined by measuring the hallmarks of apoptosis such as chromatin condensation, nuclear fragmentation, or mitochondrial release or cytochrome c.

In some embodiments, the viability or functionality of the renal tubule model is determined by measuring changes in cellular or nuclear morphology. Methods of measuring changes in cellular or nuclear morphology include examination by histology or microscopy.

In some embodiments, the viability or functionality of the renal tubule model is determined by measuring changes in the number or morphology of mitochondria. The number and morphology of mitochondria can be measured using histology or microscopy. In some embodiments, the viability or functionality of the renal tubule model is determined by measuring the downstream function of mitochondria. The downstream function of mitochondria can be measured using a commercially available kit to measure mitochondria respiration.

In some embodiments, the viability or functionality of the renal tubule model is determined by measuring the secretion of a cytokine or a chemokine. In some embodiments, the secretion of cytokines and chemokines can be measured by histology, ELISA, mass spectroscopy, a clinical chemical analyzer, or an immunoassay analyzer.

In some embodiments, the viability or functionality of the renal tubule model is determined by measuring the amount and/or pattern of deposition of the extracellular matrix. In some embodiments, the amount and/or pattern of deposition of the extracellular matrix can be measured by histology or an immunoassay.

In some embodiments, the viability or functionality of the renal tubule model is determined by measuring the deposition of a protein crystal or a salt crystals within the tissue. In some embodiments, the deposition of a protein crystal or a salt crystal within the tissue can be measured using histology or microscopy.

In some embodiments, the viability or functionality of the renal tubule model is determined by measuring tubular regeneration or compensatory proliferation. In some embodiments, tubular regeneration or compensatory proliferation can be measured using histology. In some embodiments, the histological stain is for proliferating cell nuclear antigen (PCNA) or Ki-67.

In some embodiments, the viability or functionality of the renal tubule model is determined by measuring epithelial-mesenchymal transition (EMT). In some embodiments, EMT can be measured using histology or microscopy.

In some embodiments, the viability or functionality of the renal tubule model is determined by measuring inflammation. In some embodiments, inflammation can be measured using histology, ELISA, mass spectroscopy, a clinical chemical analyzer, an immunoassay analyzer, or by gene expression using a molecular diagnostic analyzer.

In some embodiments, the viability or functionality of the renal tubule model is determined by measuring ischemia. In some embodiments, ischemia can be measured by looking for the evidence of hypoxia inductable factors. Evicence of hypoxia inductable factors can be measured using histology or by gene expression using a molecular diagnostic analyzer.

In some embodiments, the viability or functionality of the renal tubule model is determined by measuring hyperproliferation. In some embodiments, hyperproliferation can be measured using histology or microscopy.

In some embodiments, the viability or functionality of the renal tubule model is determined by measuring alterations in gene expression. In some embodiments, alterations in gene expression can be measured using a molecular diagnostic analyzer (e.g., a microarray, RNA sequencing, or a aPCR).

In some embodiments, the viability or functionality of the renal tubule model is determined by alterations in protein expression and/or post-translational modification. In some embodiments, levels of protein expression and post-translational modification of proteins can be measured using histology, microscopy, flow cytometry, Western blot, ELISA, an immunoassay, or a molecular diagnostic analyzer.

In some embodiments, the viability or functionality of the renal tubule model is determined by measuring secretion of biomarkers. In some embodiments, secretion of biomarkers can be measured using ELISA, a protein activity assay, an immunoassay, or a molecular diagnostic analyzer. In other embodiments, secretion of nuclear biomarkers such as micro-RNAS can be measured using a molecular diagnostic analyzer (e.g., a microarray, RNA sequencing, or a qPCR). In other embodiments, secretion of other chemical biomarkers can be measured using mass spectroscopy or a clinical chemical analyzer.

In some embodiments, the viability or functionality of the renal tubule model is determined by measuring epigenetic changes. In some embodiments, epigenetic changes can be measured using a molecular diagnostic analyzer (e.g., a DNA methylation kit).

In some embodiments, the viability or functionality of the renal tissue cells is determined by measuring changes in expression and/or concentration of cytoplasmic proline-rich tyrosine kinase-2 (Pyk2) expression, thiazide-sensitive cotransporter (TSC) expression, epidermal growth factor (EGF) expression, transforming growth factor-alpha (TGF-α) expression, stem cell factor (SCF) expression, transforming growth factor-beta (TGF-β) expression, connective growth tissue factor (CTGF) expression, complement factor B expression, toll-like receptor 2 (TLR2) expression, toll-like receptor 4 (TLR4) expression, interleukin-6 (IL-6) expression, Class II major histocompatibility complex (MHC) expression, intercellular adhesion moleculare-1 (ICAM-1) expression, monocyte chemoattractant protein-1 (MCP-1) expression, or plasminogen activator inhibitor-1 (PAI-1) expression compared to a control. Changes in expression and/or concentration of these factors may be measured according to methods that are well known in the art including antibody based assays.

Cytoplasmic proline-rich tyrosine kinase-2 (Pyk2) has been found to be abundantly expressed in tubular epithelial cells were it is activated by several stimuli including agonists for G protein-coupled receptors, intracellular calcium concentration, inflammatory cytokines, stress signals, and integrin-mediated cell adhesion (Sonomura et al., 2012). It is believed that Pyk2 may be an important initiating factor in renal fibrosis.

Thiazide-sensitive cotransporter (TSC) has been shown to be localized to the distal convoluted tubule in the kidney by in situ hybridization studies, in reverse transcription, and in polymerase chain reaction with microdissected nephron segments (Taniyama et al., 2001). Mutations that may lead to loss of function in the human TSC gene have been shown to cause Gitelman's syndrome, which is characterized by dehydration, hypokalemic metabolic alkalosis, hypomagnesemia, and hypocalciuria.

ErbB signaling has been found to be involved in renal electrolyte homeostatis and maintenance of kidney integrity (Melenhorst et al., 2008). The ErbB receptor family belongs to subclass I of the receptor tyrosine kinase superfamily and incorporates epidermal growth factor (EGF) receptors (EGFR, HER1, and ErbB1), HER2/neu (ErbB2), HER3 (ErbB3), and HER4 (ErbB4). EGFR expression has been detected in the tubules in most normal human kidneys. Furthermore, an increase in EGF was associated with a decrease in renal function and decreased tubulointerstitial EGF expression correlated with the severity of apoptosis.

Transforming growth factor-alpha (TGF-α) has been detected in primitive tubules in human kidney dysplasia (Melenhorst et al., 2008).

The cytokine stem cell factor (SCF) has been shown to protect the tubular epithelium against apoptosis (Stokman, G., 2010). Survival of the tubular epithelium is important to successfully regenerate renal tissue following renal ischemia.

Transforming growth factor-beta 1 (TGF-β1) has been found to promote tissue regeneration following acute injury via an autocrine or paracrine mechanism (Basile et al., 1996). Elevated expression of TGF-β1 was found to be localized predominantly to cells in the regenerating tubules in the outer medulla. TGF-β1 expression was also found to be inhibited by peroxisome proliferator-activated receptor-γ (PPAR-γ) (Wang et al., 2009). PPAR-γ has been found to have anti-inflammatory effects in kidney disease.

Connective tissue growth factor (CTGF) has been found to act as a downstream mediator for the profibrotic effects of TGF-β1 in the remnant kidney and may be a target for antifibrotic drugs designed to treat TGF-β1 dependent interstitial fibrosis (Okada et al., 2005). It has also been found that after treatment with the glucocorticoid dexamethasone, renal tubular epithelial cells from patients with minimal change nephritic syndrome produced CTGF (Okada et al., 2006).

The expression of complement factor B has been shown to increase in human proximal tubular cells and mouse tubular epithelial cells after stimulation with toll-like receptor 4 (lipopolysaccharide) or toll-like receptor 3 (polyinosinic-olycytidylic acid) (Li et al., 2016).

Exposure of renal tubular epithelial cells to tumor necrotic factor alpha (TNF-α) and triptolide followed by examination of expression of B7-H1 and B7-DC by flow cytometric analysis, showed that B7-H1 but not B7-DC constitutively expresses on renal tubular epithelial cells (Chen et al., 2006). And, B7-H1 was shown to be profoundly upregulated by the stimulation of TNF-α and downregulated by triptolide. A distinct expression pattern of toll-like receptors (TLRs) was found in mouse primary renal tubular epithelial cells and it was found that the epithelial cells secreted C—C chemokines in response to direct stimulation (Tsuboi et al., 2002). In particular, it was shown that TLR2 and TLR4 expressed in mouse primary renal tubular epithelial cells mediated direct responses to bacterial components.

Interleukin-6 (IL-6) expression in renal tubular epithelial cells has been found to be inhibited by administration of the immunosuppressant drug mycophenolic acid (Baer et al., 2004). IL-6 has been implicated in the development of tubular injury in various forms of immune-mediated renal diseases.

Class II major histocompatibility complex (MHC) and B7-1 expression in renal tubular epithelial cells were found to be mediated by interferon-gamma (IFN-γ) and liposaccharide (Banu et al., 1999).

Intercellular adhesion molecular-1 (ICAM-1) expression was found to be upregulated in renal tubular epithelial cells by the cytokines interferon-γ, TNF-α, and IL-1 (Ishikura et al., 1991).

Monocyte chemoattractant protein-1 (MCP-1), a chemokine with potent chemotactic activity for monocytes/macrophages and T lymphocytes, has been found to be upregulated in proximal renal tubular cells challenged with protein overload (Zoja, et al., 2003). And, the chemokine fractalkine was also found to be overexpressed upon albumin stimulation of proximal renal tubular cells.

Angiotensin II and Angiotensin IV were shown to induce an increase in plasminogen activator inhibitor-1 (PAI-1) expression in a proximal tubular epithelial cell line from a normal adult human kidney (Gesualdo et al., 1999). PAI-1 has been found to prevent the transformation of metalloproteinases, which are potent ECM degradation enzymes, which contribute to tubulointerstitial fibrosis.

Models of Renal Fibrosis

Provided are models of renal fibrosis, comprising a three-dimensional, engineered, bioprinted, biological renal tubule model. In some embodiments, the three-dimensional, engineered, bioprinted, biological renal tubule models comprise a layer of renal interstitial tissue, the renal interstitial tissue comprising renal fibroblasts, endothelial cells and/or fibrotic tissue; and a layer of renal epithelial tissue, the renal epithelial tissue comprising renal tubular epithelial cells; provided that the interstitial tissue comprises an interstitial bio-ink, the epithelial tissue comprises an epithelial bio-ink, and form a three-dimensional, engineered, biological renal tubule model. In one embodiment, the model of renal fibrosis displays contraction, curling, expansion of the tissue, or another fibrosis phenotype when fibrosis is present in the model.

In some embodiments, the model further comprises a layer of basement membrane between the renal interstitial tissue layer and the renal epithelial tissue layer. In some embodiments, the layer of renal epithelial tissue is in continuous contact with the layer of basement membrane, and the layer of basement membrane is in continuous contact with the layer of renal interstitial tissue.

In some embodiments, the fibroblasts and endothelial cells are present in the layer of renal interstitial tissue at a ratio of about 50:50 fibroblasts to endothelial cells.

In some embodiments, the renal tubular model displays deformation of the planar tissue structure and excess extracellular matrix deposition.

In some embodiments, the fibroblasts and endothelial cells are present in a ratio at which the renal tubule model is planar six days post-printing.

Also provided are methods of making the model of renal fibrosis comprising contacting a three-dimensional, engineered, bioprinted, biological renal tubule model with an agent that is capable of inducing interstitial fibrotic tissue formation, wherein the renal tubule model comprises: a layer of renal interstitial tissue, the renal interstitial tissue comprising renal fibroblasts and endothelial cells; and a layer of renal epithelial tissue, the renal epithelial tissue comprising renal tubular epithelial cells, to form the three-dimensional, engineered, biological renal tubule model; provided that the interstitial tissue comprises an interstitial bio-ink, the epithelial tissue comprises an epithelial bio-ink, and form a three-dimensional, engineered, biological renal tubule model.

In some embodiments, the agent that is capable of inducing interstitial fibrotic tissue deposition is cyclosporine A, aristolochoic acid, tacrolimus, TGF-β, cisplatin, acyclovir, allopurinol, beta lactam antibiotics, indinavir, lansoprazole, omeprazole, pantoprazole, phenytoin, ranitidine, or vancomycin.

The disclosure herein includes business methods. In some embodiments, the speed and scalability of the techniques and methods disclosed herein are utilized to design, build, and operate industrial and/or commercial facilities for production of renal tubule models for use in cell-based tools for research and development, such as in vitro assays. In further embodiments, the renal tubule models and arrays thereof are produced, stored, distributed, marketed, advertised, and sold as, for example, cellular arrays (e.g., microarrays or chips), tissue arrays (e.g., microarrays or chips), and kits for biological assays and high-throughput drug screening. In other embodiments, the engineered renal tubule models and arrays thereof are produced and utilized to conduct biological assays and/or drug screening as a service.

Validation

The ideal engineered renal tissues are fully human and multicellular, comprising renal tubular epithelial cells, renal interstitial fibroblasts, and endothelial cells. Moreover, ideal engineered renal tissues demonstrate specific functions including, but not limited to, CYP1A2, CYP2C9, and CYP3A4 activity, albumin transport, and vitamin D hydroxylation, γ-glutamyl-transferase activity. Also, the ideal engineered renal tissues are characterized by tight junctions, cadherin, polarity of transporters, and CD31 expression and are validated by specific assays including albumin transport, CYP450 activity, histology, and viability. In some embodiments, the renal tubule models of the present disclosure display increased specific functions compared to 2D co-culture or tissue explants that have been maintained in culture longer than 1, 2, 3, 4, 5, 6, 7, 8, 9, 10, or more days. In some embodiments, the renal tubule models of the present disclosure display 2-fold increased specific functions compared to 2D co-culture or tissue explants that have been maintained in culture longer than 1, 2, 3, 4, 5, 6, 7, 8, 9, 10, or more days. In some embodiments, the renal tubule models of the present disclosure display 5-fold or more increased specific functions compared to 2D co-culture or tissue explants that have been maintained in culture longer than 1, 2, 3, 4, 5, 6, 7, 8, 9, 10, or more days. In some embodiments, the renal tubule models of the present disclosure display 2-fold or more increased specific functions compared to 2D co-culture or tissue explants that have been maintained in culture longer than 21 or more days. In some embodiments, the renal tubule models of the present disclosure display 5-fold or more increased specific functions compared to 2D co-culture or tissue explants that have been maintained in culture longer than 27 or more days. In some embodiments, the renal tubule models of the present disclosure display 2-fold or more increased specific functions compared to 2D co-culture or tissue explants that have been maintained in culture longer than 27 or more days. In some embodiments, the renal tubule models of the present disclosure display 5-fold or more increased specific functions compared to 2D co-culture or tissue explants that have been maintained in culture longer than 21 or more days. In certain embodiments, the specific function is γ-glutamyl-transferase activity. In certain embodiments, the specific function is vitamin D hydroxylation.

In some embodiments, the engineered tissues described herein possess key architectural and functional attributes associated with in vivo human renal tissue, including histologic features and renal tubule-specific functions, including but not limited to:

Polarization of renal tubular epithelial cells w/formation of intracellular tight junctions (E-Cad, ZO-1, and Claudins) and correct intracellular localization of transporters (apical: OAT4, URAT1) and integrins (basolateral).

Development of a basal lamina between the tubular cell layer and the underlying interstitium.

Establishment of extensive microvascular networks within the interstitium, including the development of tissue-like tubular cells: microvascular spatial relationships.

Expression of compartment-specific markers, including tubular epithelial transporters (cubilin, megalin, aquaporins), OATs, URAT), vascular markers (CD31, vWF), demonstration of EPO protein production (if applicable).

Vitamin D synthesis via 25-(OH) 1-hydroxylase (1-OHase).

Production of Angiotensin II.

Active transport of albumin from tubular lumen via cubilin.

Cimetidine transport/accumulation from basolateral surface.

CYP450 and UGT expression involved in metabolism (e.g., CYP2B6, 3A5, 4A11 and UGT 1A9, 2B7, respectively).

EXAMPLES

The following illustrative examples are representative of embodiments, of the software applications, systems, and methods described herein and are not meant to be limiting in any way.

Example 1—a Bioprinted Three-Dimensional Renal Tubule Cell Model

Human umbilical vein endothelial cells (HUVEC) were purchased from BD Biosciences (Franklin Lakes, NJ) and cultured in EGM-2 media with EBM-2 supplements without gentamycin or amphotericin B (Lonza, Basel, Switzerland). Adult renal fibroblasts were purchased from DV Biologics (Yorba Linda, CA) and grown in Fibroblast Cellutions Medium with Fibroblast Cellutions supplement (DV Biologics, Yorba Linda, CA). Primary human RPTEC were purchased from four different commercial vendors (Lonza, Sciencell (Carlsbad, CA), Zen-Bio (Research Triangle Park, NC), Lifeline Cell Technology (Frederick, MD) and cultured according to the manufacturer's instructions.

All kidneys were ethically sourced through the National Disease Research Interchange (Philadelphia, PA). RPTEC cells were isolated as previously described (Vesey et al., 2009). In brief, upon receipt, kidneys were aseptically unpacked and cleaned to remove any remaining fat pads, ureters, blood vessels or other tissue. Sections of cortical tissue were minced, digested with collagenase, and the collected cells were enriched for epithelium by centrifugation across an iodixanol gradient (Sigma-Aldrich, St. Louis, MO). RPTECs were cultured in GBG Epithelial Media (Samsara Sciences, San Diego, CA).

Example 2—a Bioprinted Three-Dimensional Renal Tubule Cell Model

3D PT NOVOVIEW Tissues were fabricated as described (Nguyen et al., 2016). Briefly, cultured renal fibroblasts and HUVEC were combined in a 50:50 ratio and resuspended in NOVOGEL Bio-Ink, and then bioprinted onto 0.4 µm TRANSWELL clear polyester membrane inserts in a 24-well plate (Corning Costar, Corning, NY) using a NOVOGEN BIOPRINTER instrument (Organovo Inc., San Diego, CA) with previously established protocols (Forgacs et al., 2012; Murphy et al., 2015; Nguyen et al., 2016). Following bioprinting, NOVOVIEW Tissues were cultured in NOVOVIEW Kidney Media (Organovo, San Diego, CA). On culture day 3, primary RPTEC cells were added to the tissues in a suspension of $1.25 \times 10^6$ cells/ml in RPTEC media. Tissues were then maintained for up to 30 days in NOVOVIEW Kidney Media (Organovo, San Diego, CA), with media exchanges every other day. For toxicity studies, tissues were dosed daily to the apical and basolateral compartments beginning at day 14 of culture. For cisplatin dosing studies, culture media was supplemented with a final concentration of 2.5% FBS v/v to the apical and basolateral compartments of the TRANSWELL inserts.

Example 3—Metabolic and Viability Assays on Bioprinted Tissues

Assessment of metabolic activity as a surrogate for tissue viability and health was performed by ALAMARBLUE Assay according to the manufacturer's protocol (Thermo Fisher, Carlsbad, CA). Briefly, tissues were washed twice with Dulbecco's phosphate buffered saline (DPBS), and RPTEC media supplemented with 10% v/v ALAMARBLUE reagent was added to each tissue. All tissues were incubated for 2 hours at 37° C. with 95% relative humidity and 5% CO2. After incubation, the ALAMARBLUE solution was removed and fluorescence was measured on a BMG Labtech POLARSTAR Omega plate reader (Cary, NC) with an excitation filter of 560 nm and an emission filter of 590 nm. Graphed data represent the percent relative fluorescence units (RFU) compared to blank for metabolic activity over time, or the percent RFU compared to vehicle control for toxicity studies.

Lactate dehydrogenase (LDH) activity assay was performed according to the manufacturer's protocol (Abcam, Cambridge, MA). Conditioned media was collected from 3D PT tissues and further diluted in fresh media to ensure that the LDH activity of the sample was within the linear range of the assay. Samples were measured on a microplate reader (BMG Labtech, Cary, NC). LDH activity was determined by standard curve integration of absorbance normalized for volume and duration using GRAPHPAD PRISM software (GraphPad, San Diego, CA). Data shown represent the fold change in LDH activity relative to vehicle control for each day of sampling.

GGT activity was measured according to the manufacturer's protocol (Sigma Aldrich, St. Louis, MO). Tissues were washed twice with DPBS and lysed in GGT assay buffer in a PRECELLYS lysis tube (Precellys, Rockville, MD). Lysate was assessed for GGT activity by comparison to a standard curve integration of absorbance normalized for volume and duration of incubation period at 37° C. using GRAPHPAD PRISM software (GraphPad, San Diego, CA). Data shown represent the average GGT activity in mIU/ml for analysis of GGT function over time, or percent relative to vehicle for toxicity studies.

To measure TEER, individual 3D PT tissues cultured for 21 d were removed from the TRANSWELL insert and loaded into an Ussing chamber (Physiologic Instruments, San Diego, CA). Studies were run essentially as previously described (Clarke, 2009). Tissues were bathed in Krebs bicarbonate ringer solution with glucose (115 mM NaCl, 2.4 mM $K_2HIPO_4$, 0.4 mM $KH_2PO_4$, 1.2 mM $CaCl_2$) dihydrate, 1.2 mM $MgCl_2$ hexahydrate, 25 mM $NaHCO_3^-$, 10 mM glucose; all reagents from Sigma-Aldrich, St. Louis, MO) and buffer was continuously bubbled with carbogen gas (95% $O_2$/5% $CO_2$). After correcting the electrode offset potential and liquid resistance, resistance across the tissues was measured continuously for 1 h.

For passive permeability ($P_{app}$) measurements, tissues were washed with DPBS three times and equilibrated to assay buffer (DPBS with 10 mM HEPES pH 7.4) for 10 min at 37° C. Tissues were then dosed with 250 µM Lucifer yellow (Thermo Fisher, Carlsbad, CA) to the apical compartment and fresh assay buffer in the basolateral (receiver) compartment. Following incubation for 1 h at 37° C., samples were taken from both the apical and basolateral compartments. Fluorescence in each sample was measured on a BMG plate reader with an excitation filter of 490 nm and an emission filter of 540 nm (BMG Labtech, Cary, NC) and normalized to a standard curve for quantification. Papp was calculated with equation 1, where V represents the volume of Lucifer yellow solution, T is the duration of the incubation, $D_0$ is the concentration of Lucifer yellow applied to the cells, and A is the growth area of the TRANSWELL insert.

$$P_{app} = \left(\frac{V}{A} x D_0\right) * (\Delta D / \Delta T) \qquad \text{Equation 1}$$

Example 4—ELISA Assay for Angiotensin-Converting Enzyme (ACE) and Angiotensin II ACE protein levels in both tissue lysates and conditioned media were detected by ELISA using the manufacturer's instructions (Abcam, Cambridge, MA). Plates were read at 450 nM (BMG Labtech, Cary, NC) within 30 minutes of addition of the stop solution. Concentrations of the test samples were determined by comparison to the standard curve using GRAPHPAD PRISM software (GraphPad, San Diego, CA).

To evaluate ACE enzyme function, 3D PT tissues were treated for 24 h with 5 ng/ml human angiotensin I (Abcam, Cambridge, MA) and angiotensin II was then detected using a competitive ELISA kit from Sigma per the manufacturer's instructions (Sigma-Aldrich, St. Louis, MO). Plates were read at 450 nM within 30 minutes of addition of the stop solution (BMG Labtech, Cary, NC). The concentration of angiotensin II in the test samples was determined by comparison to the standard curve using GRAPHPAD PRISM software (GraphPad, San Diego, CA).

Example 5—a Three-Dimensional Renal Tubule Model Bioprinted with Different Ratios of Renal Fibroblasts to Endothelial Cells Experiments were undertaken to determine the effect of fibroblast to endothelial cell ratio on tissue morphology. Renal tubule models were bioprinted using bio-inks comprising renal fibroblasts and HUVEC cells at ratios of 90:10; 75:25; and 50:50 (fibroblast to endothelial cells).

Example 6—Histology

3D PT were fixed overnight in 2% paraformaldehyde (Electron Microscopy Sciences, Hatfield, PA). Tissues were oriented for transverse sectioning by pre-embedding in HISTOGEL (Thermo Fisher, Carlsbad, CA) and were then dehydrated and infiltrated with paraffin by automated processing on a TISSUE-TEK VIP tissue processing system (Sakura Finetek USA, Torrance, CA). Tissues were sectioned at 5 µM on a LEICA REICHERT-JUNG HISTOCUT microtome (Leica Biosystems, Buffalo Grove, IL). Hematoxylin and eosin (H&E) or Gomori's trichrome (TCM) stains were generated using a LEICA AUTOSTAINER XL (Leica Biosystems, Buffalo Grove, IL) according to manufacturer's instructions. Immunohistochemistry was performed as previously described (King et al., 2013) using the primary antibodies in Table 1. Following overnight incubation with primary antibodies at 4° C., sections were stained with ALEXAFLUOR-conjugated secondary antibodies (Thermo Fisher, Carlsbad, CA) at 1:200 dilution. For P-gp and SGLT2 detection, tyramide signal amplification was performed according to the manufacturer's instructions (Thermo Fisher, Carlsbad, CA). Slides were counterstained and mounted with FluoroGel II with DAPI (Electron Microscopy Sciences, Hatfield, PA). H&E and TCM images were acquired on a Zeiss Axioskop with Zeiss Zen software (Zeiss Microscopy, Thornwood, NY). Immunofluorescent images were acquired on a Zeiss Axiolmager A2 with Zeiss Zen software.

TABLE 1

| | Dilution | Vendor |
|---|---|---|
| Rabbit α-CD31 | 1:100 | Abcam (Cambridge, MA) |
| Rabbit α-TE7 | 1:500 | EMD Millipore (Temecula, CA) |
| Mouse α-collagen IV | 1:100 | Abcam |
| Rabbit α-E cadherin | 1:50 | Abcam |
| Rabbit α-Pgp | 1:500 | Abcam |
| Rabbit α-SGLT2 | 1:250 | Abcam |
| Rabbit α-Na$^+$K$^+$ATPase | 1:100 | Abcam |
| Mouse α-cytokeratin 18 | 1:500 | Abcam |
| Rabbit α-PCNA | 1:1000 | Cell Signaling (Danvers, MA) |

Example 7—RNA Isolation and Quantitative RT-PCR

RNA extraction from 3D PT tissues was performed using the Zymo DIRECTZOL RNA kit according to the manufacturer's instructions (Zymo Research, Irvine, CA). RNA was quantified by spectrophotometry using a NANODROP 2000 (Thermo Fisher, Carlsbad, CA) and converted to cDNA using SUPERSCRIPT III First-Strand Synthesis SuperMix according to the manufacturer's instructions (Thermo Fisher, Carlsbad, CA). Amplification reactions were performed with 200 ng of cDNA using TAQMAN Gene Expression Array Cards (Thermo Fisher, Carlsbad, CA) with GAPDH amplification as an endogenous housekeeping control gene. TAQMAN probe/primer sets are described in Table 2. Amplification was detected on a VIIA7 real-time PCR system (Thermo Fisher, Carlsbad, CA). Duplicate samples from individual tissues were assessed. Relative quantitation (RQ) values for the gene of interest compared to GAPDH were calculated using the formula $RQ=(2-\Delta^{Ct})*10000$. RQ values for each sample were normalized for KRT18 by dividing the RQ for the gene of interest compared to GAPDH by the RQ for KRT18 compared to GAPDH. The fold change was then calculated by dividing the KRT18-normalized RQ at the experimental day by the KRT18-normalized RQ for day 3 (or day 12 for SGLT2).

TABLE 2

| Gene | Gene Symbol | Assay ID |
|---|---|---|
| ACE | ACE | Hs00174179_ml |
| AGT | AGT | Hs01586213_ml |
| Renin | REN | Hs00982555_ml |
| MDR1 (P-gp) | ABCB1 | Hs00184500_ml |
| BCRP | ABCG2 | Hs01053790_ml |
| AQP1 | AQP1 | Hs01028916_ml |
| Cubilin | CUBN | Hs00153607_ml |
| Megalin | LRP2 | Hs00189742_ml |
| OCT2 | SLC22A2 | Hs01010723_ml |
| OAT1 | SLC22A6 | Hs00537914_ml |
| OAT3 | SLC22A8 | Hs00188599_ml |
| MATE1 | SLC47A1 | Hs00217320_ml |
| MATE2K | SLC47A2 | Hs00945650_ml |
| SGLT2 | SLC5A2 | Hs00894642_ml |

Example 8—Glucose Uptake Colorimetric Assay

Glucose uptake in 3D PT tissues was detected and quantified according to the manufacturer's protocol (Abcam, Cambridge, MA). Insulin-Transferrin-Selenium (Gibco, Carlsbad, CA) was used to stimulate glucose uptake and canagliflozin (Santa Cruz Biotech, Dallas, TX) was used to inhibit SGLT2 function. Tissues were starved overnight in DPBS/HEPES, pH 7.4 prior to assay. Tissues were then pretreated with 1× insulin or 500 μM canagliflozin for 20 minutes, followed by addition of 1 mM 2-deoxyglucose. Tissues were washed extensively with PBS and lysed in extraction buffer in PRECELLYS lysis tubes (Precellys, Rockville, MD). 2-deoxyglucose uptake was measured at OD412 nm on a microplate reader (BMG Labtech, Cary, NC) and results were graphed as fold change relative to control using GRAPHPAD PRISM Software (GraphPad, San Diego).

Example 9—Vectorial Transport of Rhodamine 123

3D PT tissues were washed with DPBS three times and equilibrated to assay buffer (DPBS supplemented with 10 mM HEPES, pH 7.4) for 10 min at 37° C. Both apical and basolateral sides of tissues were then pre-incubated for 20 min at 37° C. in assay buffer in the presence or absence of 5 μM zosuquidar (Sigma Aldrich, St. Louis, MO). Following pre-treatment, tissues were dosed on the basolateral side with 1 μM rhodamine 123 (Molecular Probes, Eugene, OR) with or without 5 μM zosuquidar for 2 h at 37° C. After incubation, the tissues were washed with cold assay buffer, fixed with 2% PFA, and cryosectioned. Images were captured at the same exposure time across all conditions. Fluorescence intensity, corrected for background and relative area, was calculated in Image J (National Institutes of Health, Bethesda, MD) and graphed as fold change relative to control using GRAPHPAD PRISM Software (GraphPad, San Diego).

Statistics were calculated using GRAPHPAD PRISM software (La Jolla, CA). Data shown is the mean±SEM. Statistical significance (P<0.05) was calculated by t-test with Dunnet's post-test, one-way ANOVA, or two-way ANOVA as appropriate.

Figure 1A:
FIGS. 1A-1B illustrate a 3D model of the PT tubulointerstitial interface printed with the NOVOGEN BIOPRINTER instrument.
Figure 1B:

Example 10—Results-Development and Characterization of a 3D Model of the Tubulointerstitial Interface of the Human PT Cultured primary human RPTECs have a finite lifespan in culture before undergoing epithelial-to-mesenchymal transition or senescence, with accompanying loss of morphology and function (Wieser et al., 2008). Abundant evidence supports the notion that an appropriate microenvironment, including 3D architecture and supporting cell types, can help maintain and support the continued health and function of polarized epithelia (Kunz-Schughart et al., 2006; Bryant and Mostov, 2008; Nagle et al., 2011; Li et al., 2014). To develop a 3D human system for studying nephrotoxicity, the Organovo NOVOGEN BIOPRINTER system was used to create a model of the PT tubulointerstitial interface (NOVOVIEW tissues). As shown in the schematic of FIG. 1A, tissues were designed with a basal multicellular interstitial layer composed of primary human renal fibroblasts and HUVEC, and an apical monolayer of polarized primary human RPTEC supported by a basement membrane. Use of the bioprinter allowed reproducible generation of spatially-defined tissues created on standard multi-well TRANSWELL inserts (FIG. 1B).

Figure 2A:
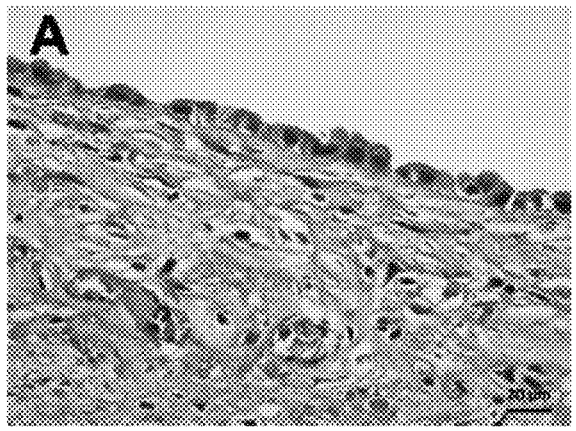
FIGS. 2A-2F are micrographs showing the histological characterization of 3D PT tissues. Representative images of tissues cultured for 14 days are shown.
Figure 2B:
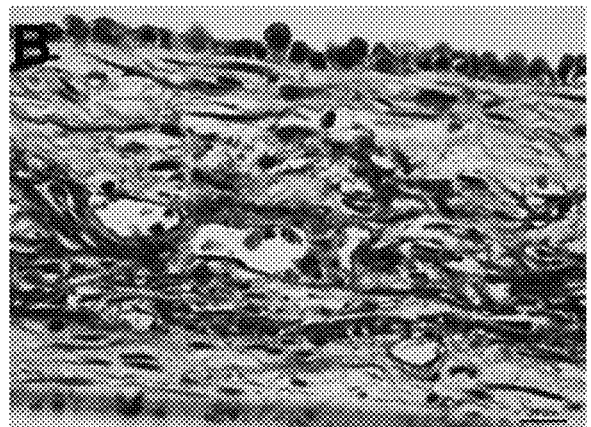
Figure 2C:
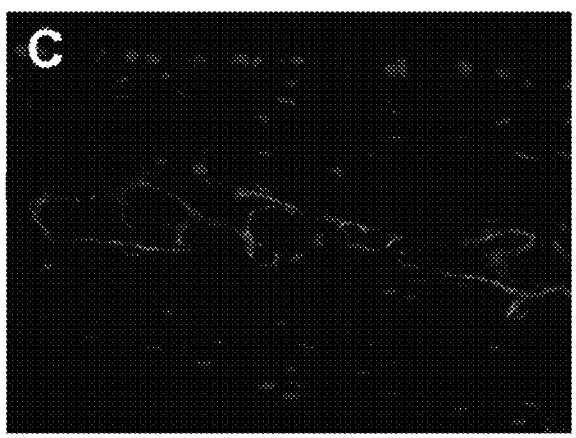
Figure 2D:
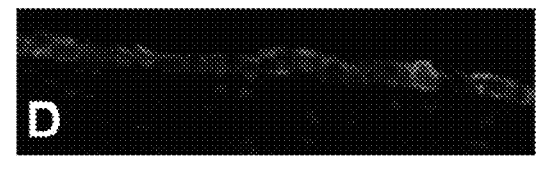
Figure 2E:
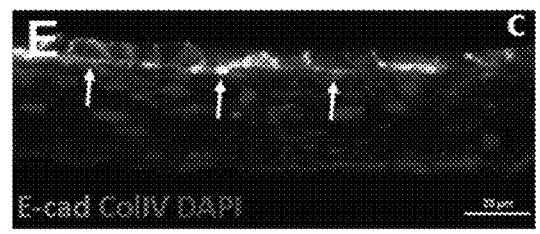
Figure 2F:

Following culture for 14 days, the PT tissues were analyzed for tissue organization, cell morphology, and retention of endothelial and epithelial markers. A hematoxylin and eosin (H&E) stain of the 3D tissues showed an interstitial layer with low cell density composed of spindle-shaped fibroblasts and areas of HUVEC undergoing remodeling to form endothelial cell-lined networks (FIG. 2A). A monolayer of RPTEC cells was observed immediately above the interstitium, with columnar morphology and basally oriented nuclei. The interstitial cells themselves secreted abundant ECM as shown by Gomori's trichrome stain, with fibrillar structures visible surrounding the endothelial cell networks (red) in the middle of the tissue as well as underlying the epithelial layer (FIG. 2B). The putative endothelial cell networks observed by H&E and trichrome expressed CD31 and demonstrated that the HUVEC had organized to form open spaces lined by endothelial cells (FIG. 2C). Separating the interstitium from the epithelium was a collagen IV-rich basement membrane immediately adjacent to the basal side of the epithelial cells (FIG. 2D). The RPTEC cells in the 3D PT model expressed cytokeratin 18 uniformly across the monolayer (FIG. 2E) with E-cadherin localized laterally between adjacent cells (FIG. 2E). Polarized distribution of Na+/K+ ATPase to the basolateral membrane of RPTEC was also observed (FIG. 2F).

Figure 3A:
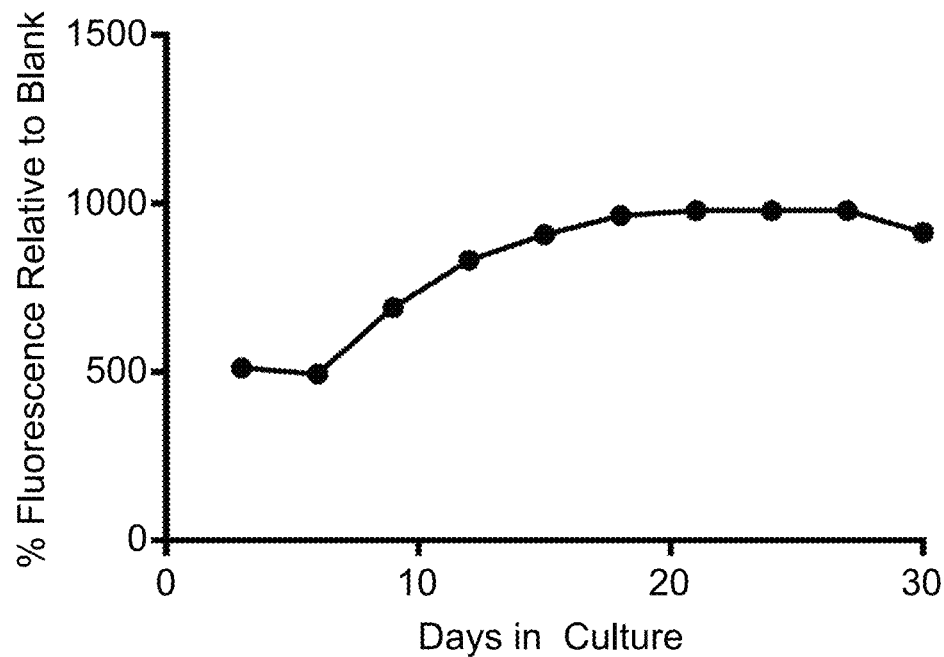
FIGS. 3A-3B are graphs showing the viability and metabolic activity of 3D PT tissues over time.
Figure 3B:
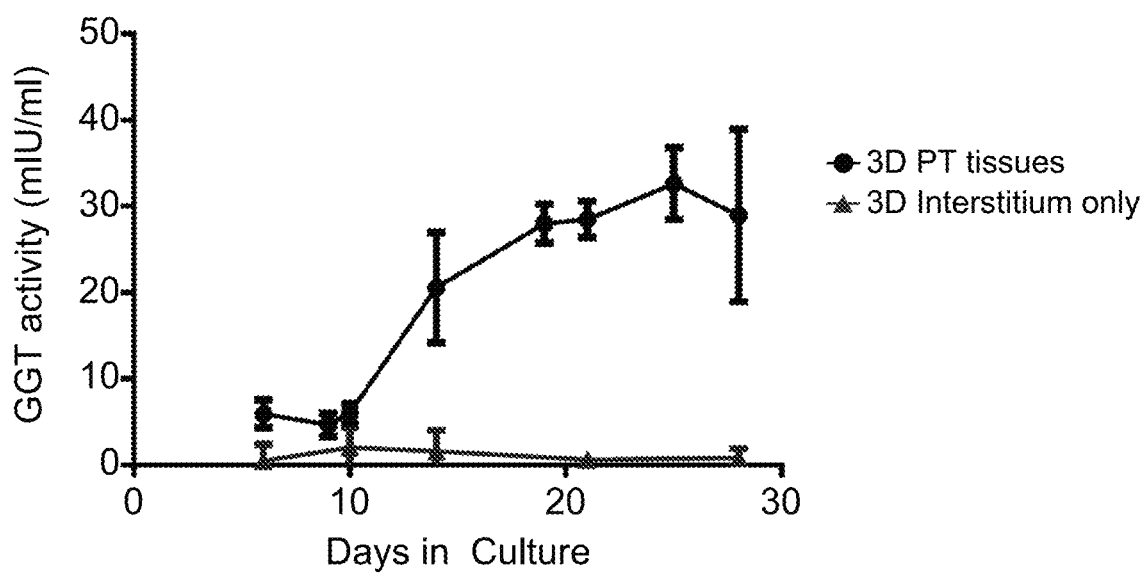

To assess global tissue metabolic activity and longevity, tissues were assessed for the ability to reduce resazurin over 4 weeks in culture in an ALAMARBLUE assay (FIG. 3A). Following an initial decrease in metabolic activity from day 3 to day 7, the metabolic activity of the 3D PT tissues continued to increase between day 10 and day 30. To more specifically assess RPTEC functional longevity, 3D PT tissues or tissues lacking epithelium (interstitium only) were assessed for GGT activity as a function of time in culture. The 3D PT tissues exhibited an increase in GGT activity from 5 mIU/ml at day 7 to 30 mIU/ml at day 30 (FIG. 3B). As expected, the interstitium-only tissues lacking RPTEC exhibited negligible GGT activity throughout the culture period of 30 days (FIG. 3B). Together, these findings demonstrate the formation of a robust 3D model of the renal tubulointerstitial interface capable of supporting RPTEC morphology, viability and function for at least 4 weeks.

Example 11—Characterization of Barrier Function

To measure the barrier function of the 3D PT tissues, trans-epithelial electrical resistance (TEER) measurements were performed using an Ussing chamber after 21 days in culture. Table 3 shows the average area-corrected resistance values for 3D PT tissues, which averaged 18.1 $\Omega*cm^2$. Passive permeability (Papp) was also measured in 3D PT tissues by addition of Lucifer yellow to the apical or basolateral compartment of the TRANSWELL and detection of the fluorophore in the opposite compartment as a function of time. 3D PT tissues exhibited an average Papp value of $2.97 \times 10^{-6}$ cm/s indicating that the 3D PT tissues exhibited a more permeable barrier than observed for epithelial monolayers with Lucifer yellow (Tran et al., 2004). Taken together, these values demonstrate that the barrier formed by the RPTEC cells in the 3D PT tissues is leakier than isolated epithelial monolayers but characteristic of the barrier observed for the PT in vivo (Boulpaep and Seely, 1971; Liang et al., 1999)

TABLE 3

| Tissue | R (Avg) $\Omega*cm^2$ | Papp × $10^{-6}$ cm/s |
|---|---|---|
| 1 | 18.1 | 2.63 |
| 2 | 16.3 | 2.73 |
| 3 | 13.9 | 2.66 |
| 4 | 17.4 | 3.74 |
| 5 | 19.2 | 3.11 |
| 6 | 23.4 | 2.93 |
| Avg | 18.1 ± 1.3 | 2.97 ± 0.17 |

Example 12—Assessment of the Intrarenal Renin-Angiotensin System (RAS)

Figure 4A:
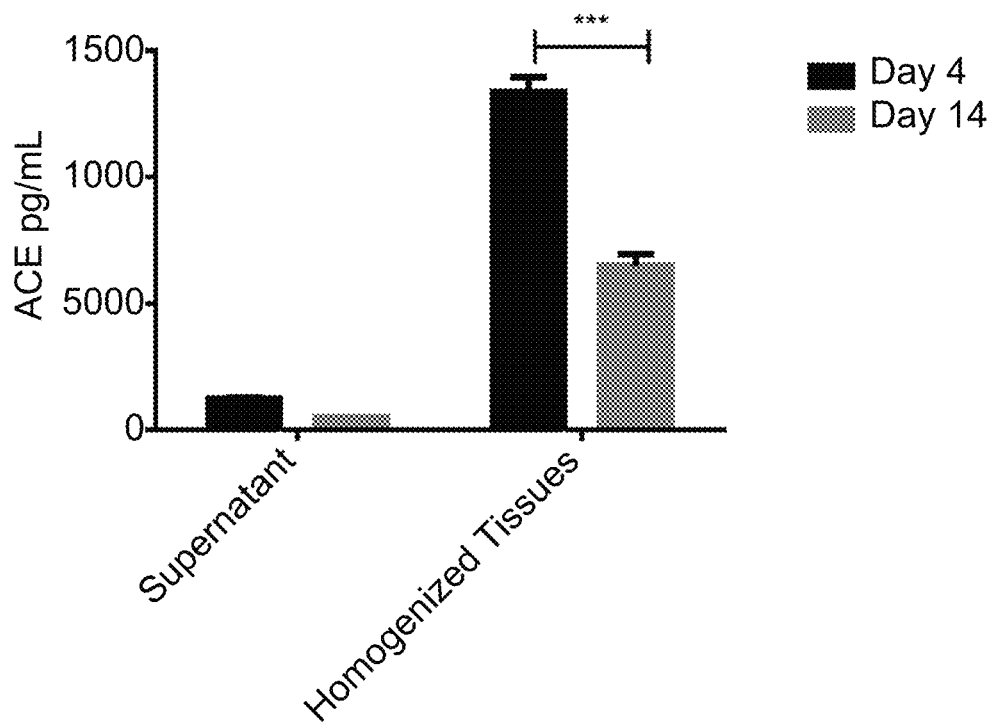
FIGS. 4A-4B are bar graphs showing the RAS pathway component activity in 3D PT tissues.
Figure 4B:
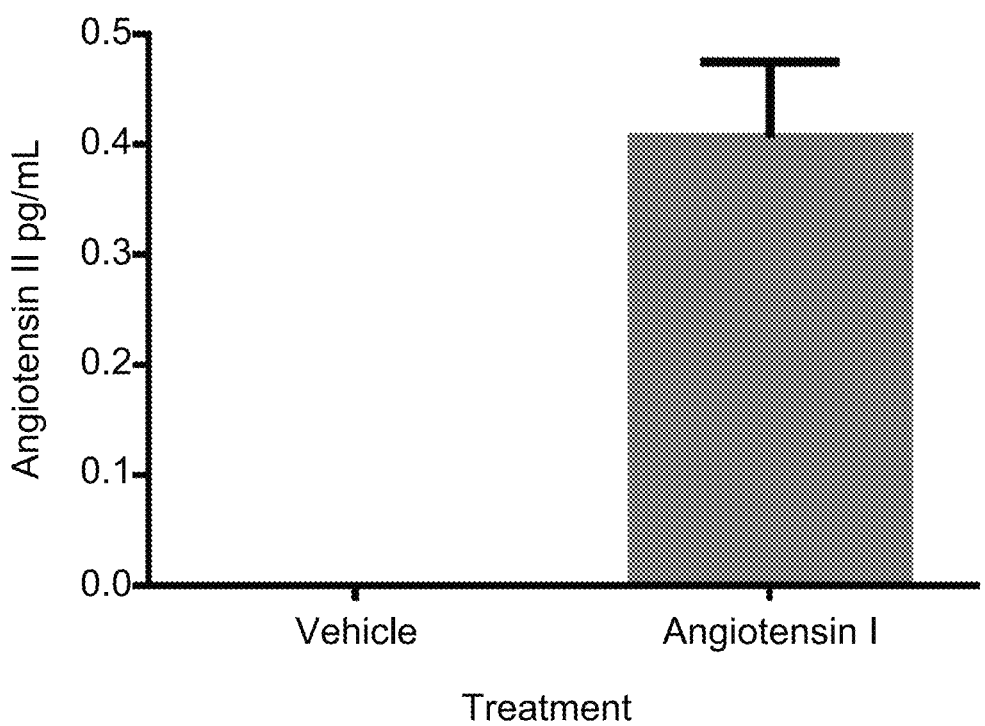

To determine whether the 3D PT tissues retained a viable RAS, gene expression of several members of the pathway were first measured. Gene expression analysis of the tissues over 30 days in culture showed detectable levels of ACE, angiotensinogen (AGT), angiotensin receptor I (AGTR1), and renin (Tables 1 and 4). Consistent with the gene expression data, ACE protein was detected in both conditioned media and tissue lysates, with higher detection in the tissue lysates (FIG. 4A). This may correlate with the observed expression of ACE in the brush border of the PT (Kobori et al., 2007). To evaluate the function of ACE, 3D PT tissues were dosed with 5 ng/ml human angiotensin I for 24 h and assessed for the ability to convert angiotensin I to angiotensin II. Following stimulation, angiotensin II was detected in 3D PT tissues at 0.4 pg/ml (FIG. 4B). Thus the 3D PT tissues exhibited physiologically relevant features of the in vivo PT, including development of barrier functions and conversion of angiotensin I to angiotensin

TABLE 4

| | Day 3 | Day 12 | | Day 18 | | Day 24 | | Day 30 | |
|---|---|---|---|---|---|---|---|---|---|
| Target Name | KRT18-normalized RQ | KRT18-normalized RQ | Fold change relative to day 3 | KRT18-normalized RQ | Fold change relative to day 3 | KRT18-normalized RQ | Fold change relative to day 3 | KRT18-normalized RQ | Fold change relative to day 3 |
| ACE | 10.81 | 3.84 | 0.36 | 6.96 | 0.64 | 6.65 | 0.61 | 5.75 | 0.53 |
| AGT | 5.69 | 15.83 | 2.78 | 25.03 | 4.4 | 25.60 | 4.5 | 37.96 | 6.68 |
| REN | 1.18 | 0.6 | 0.51 | 1.84 | 1.56 | 2.37 | 2.02 | 1.6 | 1.36 |

Example 13—Analysis of Renal Transporters in 3D PT Tissues

A key feature of the PT that relates to its susceptibility to nephrotoxicity is the expression and function of renal transporters, which take up or efflux compounds from the capillaries surrounding the PT or the glomerular filtrate in the lumen of the tubule. Primary human RPTEC dedifferentiate rapidly when cultured in 2D, exhibiting varying levels of renal transporters and a range of cellular morphologies depending on the time and method of culture (FIGS. 11A-11E and Wieser et al., 2008; Vesey et al., 2009). We hypothesized that culturing low-passage primary human RPTEC on a relevant renal interstitium would preserve transporter expression and function. To validate the use of the 3D PT model for transporter-dependent toxicity studies, tissues were first analyzed for relative expression levels of key renal transporter genes by qPCR (Tables 1 and 5). For the individual donor cells incorporated into 3D PT tissues in this study, nearly all renal transporters evaluated exhibited stable, detectable gene expression for greater than 4 weeks in culture (Table 5). The xenobiotic transporter OCT2 was detected at relatively high levels throughout 28 days in culture, with a 1.8-fold increase in expression at day 30 compared to day 3 (Tables 1 and 5). Luminal reabsorption transporters for endogenous substrates, including cubilin, megalin, AQP1, and SGLT2 exhibited detectable expression over 30 days in culture. Megalin expression decreased slightly after 18 days in culture, but SGLT2 expression increased over time (Tables 1 and 5). Of the efflux transporters analyzed, P-gp exhibited the highest expression level, with peak expression between days 18 and 30 in culture (Tables 1 and 5).

Figure 5A:
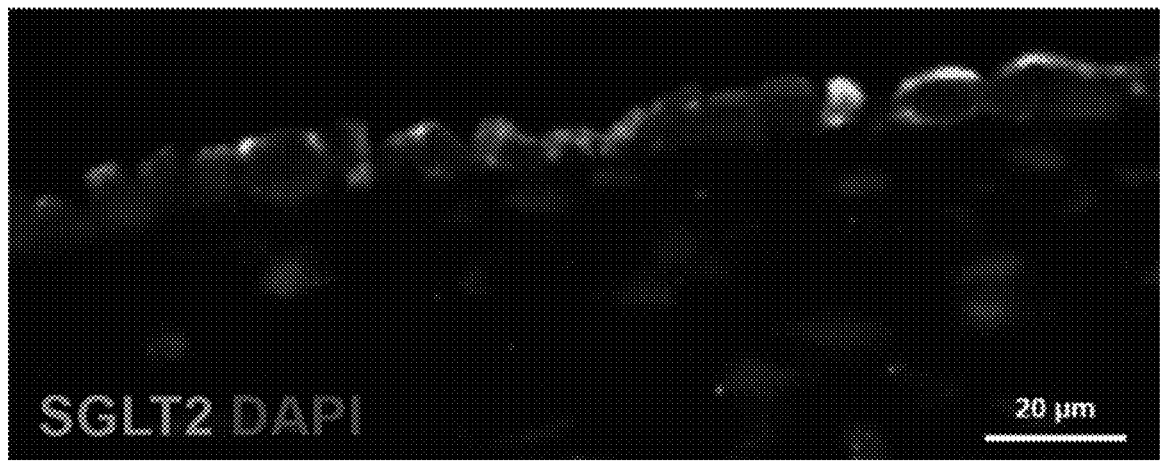
FIGS. 5A-5B are a micrograph and a bar graph, respectively, showing SGLT2 transporter localization and function.
Figure 5B:
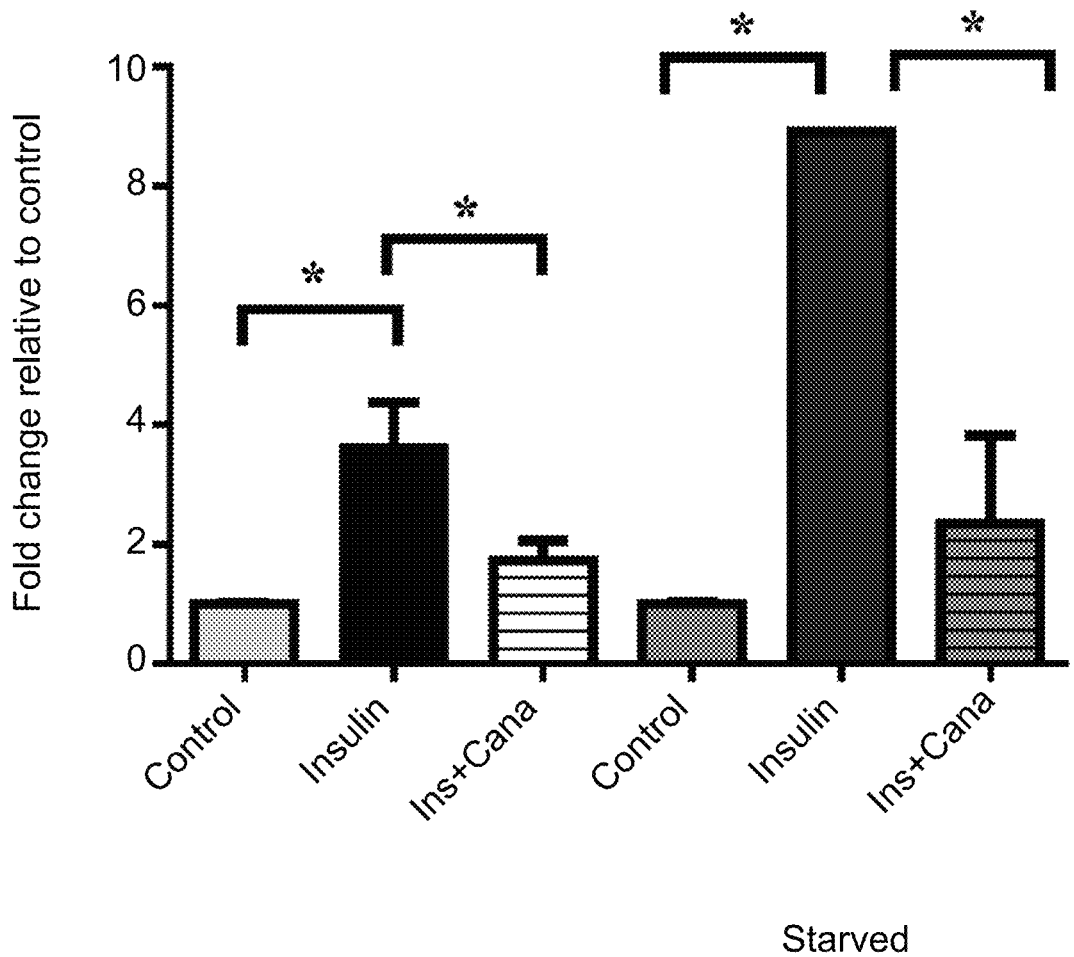

To further assess both uptake and efflux transporter function in the 3D PT model, the glucose uptake transporter SGLT2 and the xenobiotic efflux transporter P-gp were selected for functional analysis. As shown in FIG. 5A, SGLT2 protein expression was detected primarily at the apical surface of RPTEC on 3D PT tissues (3D) tissues were stained with antibodies against SGLT2). This pattern matches what is seen in vivo in the human PT (Brenner, 2008). To evaluate SGLT2 transporter function, tissues were kept in either normal tissue maintenance media or starved of glucose for 24 h, followed by stimulation of glucose uptake by insulin in the presence or absence of the SGLT2 transport inhibitor canagliflozin (FIG. 5B). In tissues maintained in normal tissue media, treatment with insulin induced a 4-fold increase in intracellular 2-DG, which decreased by 50% upon co-administration of the SGLT2 inhibitor canagliflozin (FIG. 5B, black and grey bars). This suggests that there is functional SGLT2 transport in the tissues, and that other transport mechanisms are also contributing to global glucose uptake. When tissues were starved overnight, insulin induced an 8-fold increase in glucose uptake, which was significantly reduced by canagliflozin to levels indistinguishable from the control tissues (FIG. 5B). As expected, starvation increased glucose uptake by 3D PT tissues beyond that observed for tissues cultured in normal media as the tissues sought to re-establish glucose homeostasis lost during culture in the absence of glucose, and SGLT2 appears to play a role in this process.

To assess P-gp mediated efflux capabilities in 3D PT tissues, we first wanted to determine the localization of the transporter protein. As expected for native proximal tubule, P-gp protein expression was detected at the apical surface of the RPTEC cells in the 3D PT model. After 14 days in

TABLE 5

| Target Name | Day 3 KRT18-normalized RQ | Day 12 | | Day 18 | | Day 24 | | Day 30 | |
| --- | --- | --- | --- | --- | --- | --- | --- | --- | --- |
| | | KRT18-normalized RQ | Fold change relative to day 3 | KRT18-normalized RQ | Fold change relative to day 3 | KRT18-normalized RQ | Fold change relative to day 3 | KRT18-normalized RQ | Fold change relative to day 3 |
| ABCB1 (MDR1, P-gp) | 2.77 | 18.91 | 6.82 | 63.79 | 23.02 | 42.18 | 15.22 | 77.6 | 28 |
| ABCG2 (BCRP) | 9.82 | 1.58 | 0.16 | 15.94 | 1.62 | 2.77 | 0.28 | 0.84 | 0.09 |
| AQP1 | 5.42 | 4.89 | 0.9 | 5.44 | 1 | 4.72 | 0.87 | 8.21 | 1.52 |
| CUBN | 0.63 | 10.74 | 17 | 15.03 | 23.79 | 11.29 | 17.88 | 21.13 | 33.46 |
| LRP2 (megalin) | 0.83 | 0.69 | 0.83 | 2.07 | 2.5 | 0.92 | 1.12 | 0.54 | 0.66 |
| SLC22A2 (OCT2) | 8 | 14.71 | 1.84 | 22.09 | 2.76 | 6.91 | 0.86 | 14.45 | 1.81 |
| SLC22A6 (OAT1) | ND | ND | ND | ND | ND | ND | ND | ND | ND |
| SLC22A8 (OAT3) | ND | ND | ND | ND | ND | ND | ND | ND | ND |
| SLC47A1 (MATE1) | 3.78 | 3.52 | 0.93 | 4.85 | 1.28 | 1.87 | 0.5 | 1.55 | 0.41 |
| SLC47A2 (MATE2K) | 0.79 | 4.69 | 5.98 | 2.15 | 2.74 | 2.31 | 2.94 | 4.88 | 6.21 |
| SLC5A2 (SGLT2) | ND | 0.88 | ND | 0.63 | 0.71 | 2.03 | 2.3 | 3.02 | 3.43 |

Figure 6A:
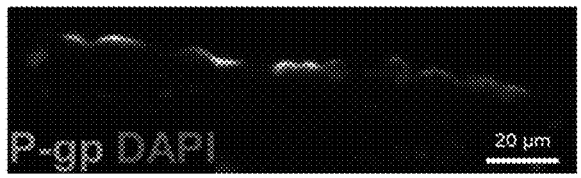
FIGS. 6A-6E are micrographs and a graph (FIG. 6E) showing P-gp transporter localization and function.
Figure 6B:
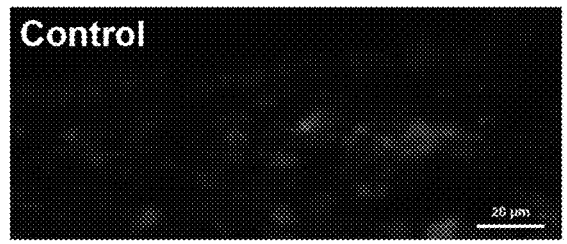
Figure 6C:
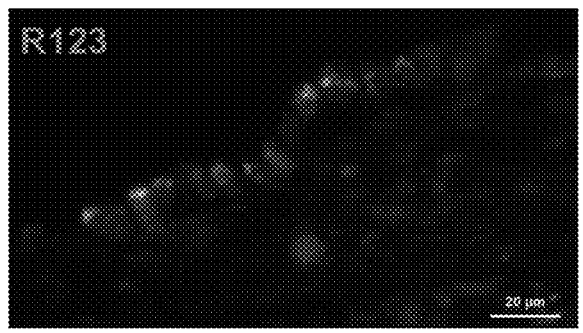
Figure 6D:
Figure 6E:
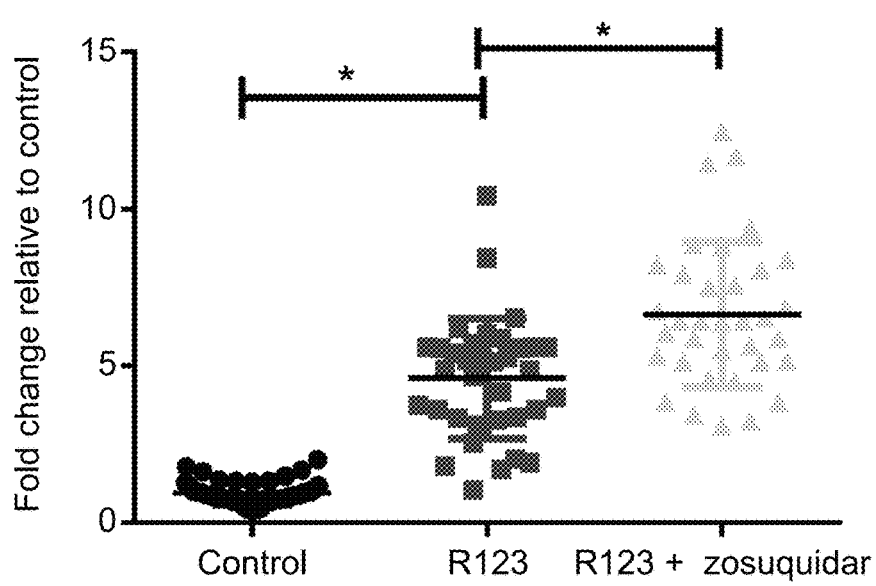

(OAT3), SLC47A1 (MATE1), SLC47A2 (MATE2K), and SLC5A2 (SGLT2) expression relative to GAPDH and normalized to KRT18 between days 3 and 30 of culture. Data shown is the average relative quantification (RQ) compared to GAPDH and normalized to KRT18 and the fold change compared to day 3 for 2 tissues per time point. For SGLT2, fold change shown is relative to day 12. ND, not detected.

culture, 3D PT tissues were stained with antibodies against P-gp (FIG. 6A and (Brenner, 2008)). To evaluate P-gp function, 3D PT tissues were loaded with rhodamine 123 (R123) in the presence or absence of zosuquidar, a P-gp inhibitor. Following uptake, tissues were washed and cryo-sectioned to detect the presence of R123 in the RPTEC of the PT model. Tissues treated with buffer alone exhibited no green fluorescence (control), while tissues treated with R123 exhibited punctate fluorescent expression in the cytoplasm of the RPTEC. Upon blocking P-gp-mediated efflux with zosuquidar, an increase in accumulated fluorescence was observed in the epithelium with the RPTEC monolayer fluorescing uniformly throughout the cytoplasm (FIG. 6B). Image quantification showed that tissues exposed to R123 exhibited a 4-fold increase over control tissues, while treatment with R123 plus zosuquidar resulted in a 6-fold increase in fluorescence over control tissues and a significant increase compared to R123-treatment alone (FIG. 6C). Thus the 3D PT tissues exhibited stable expression of renal transporters over time, and functional activity of the endogenous substrate transporter SGLT2 and the xenobiotic transporter P-gp were verified.

Example 14—Assessment of Cisplatin Nephrotoxicity Using 3D PT Tissues

Figure 7A:
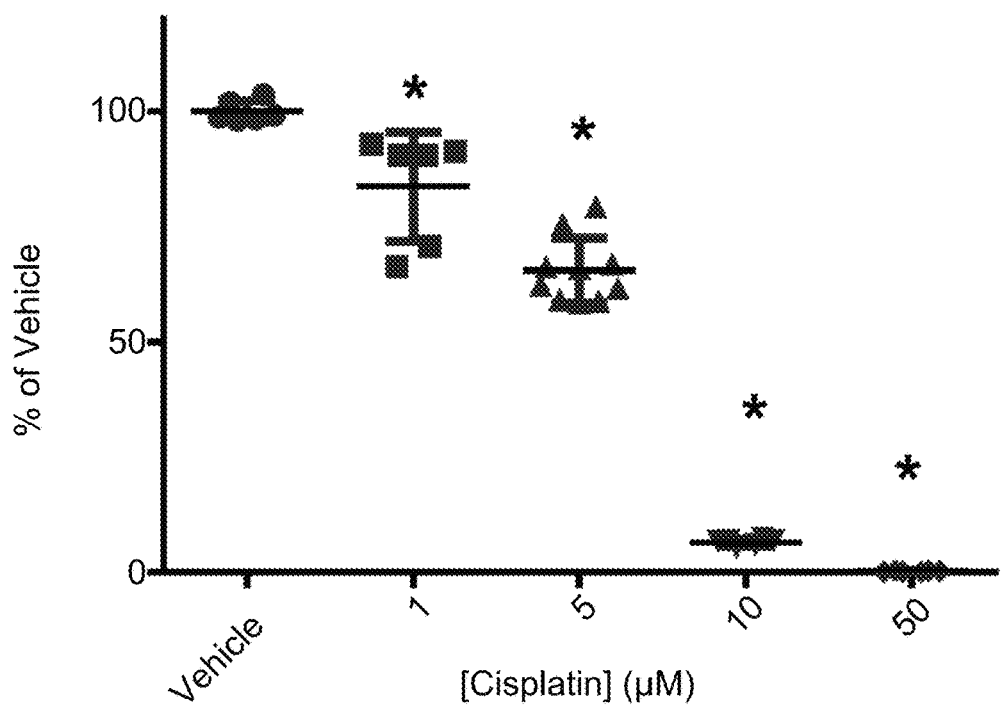
FIGS. 7A and 7B are graphs showing that cisplatin decreases overall viability and epithelial function in 3D PT tissues. Tissues were treated daily for 7 days with increasing doses of cisplatin.
Figure 7B:
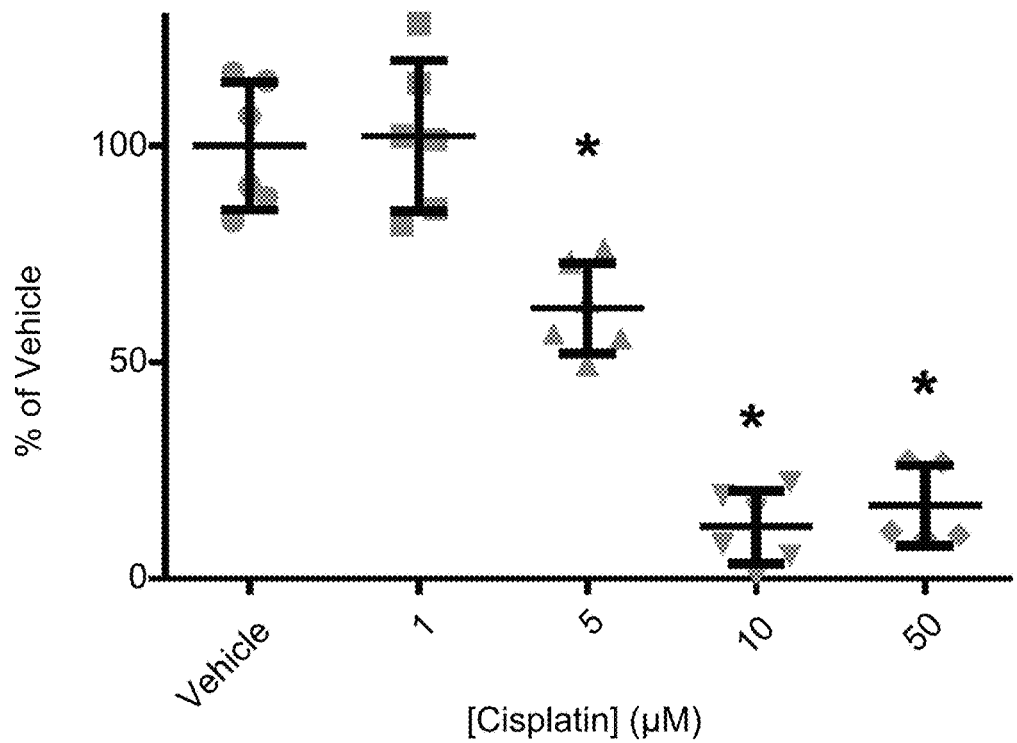

Cisplatin is a chemotherapeutic agent with multiple mechanisms of action that lead to nephrotoxicity, including generation of reactive oxygen species and formation of toxic glutathione conjugates following concentration of the molecule in RPTEC by renal uptake transporters including OCT2 (Hanigan and Devarajan, 2003; Yonezawa et al., 2005). In addition, cisplatin has been reported to lead to tubulointerstitial fibrosis (Guinee et al., 1993). To assess whether the 3D PT tissues could manifest cisplatin toxicity, tissues were exposed daily to cisplatin followed by measurement of overall viability, levels of GGT activity, release of LDH, and histological analysis. Tissues treated with cisplatin exhibited a significant decrease in ALAMARBLUE metabolism at doses as low as 1 µM, with an LD 50 value of 5.72 µM and complete loss of viability at 10 µM (FIG. 7A). A similar pattern was observed for GGT activity in response to cisplatin, with 5 µM cisplatin causing a nearly 50% reduction in GGT activity, indicating a significant effect on the RPTEC of the 3D PT model (FIG. 7B).

Figure 8A:
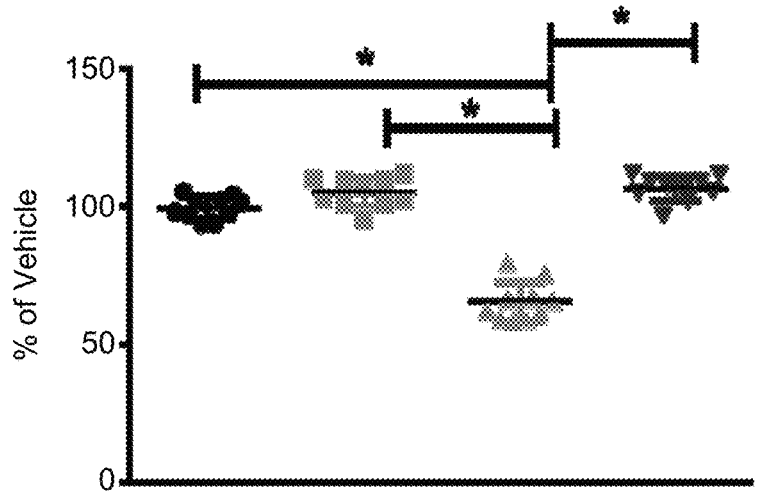
FIGS. 8A-8C are graphs showing rescue of cisplatin-induced toxicity by OCT2 inhibition. 3D PT tissues were dosed daily for 7 days with vehicle, cimetidine alone, 5 µM cisplatin, or cisplatin with cimetidine.
Figure 8B:
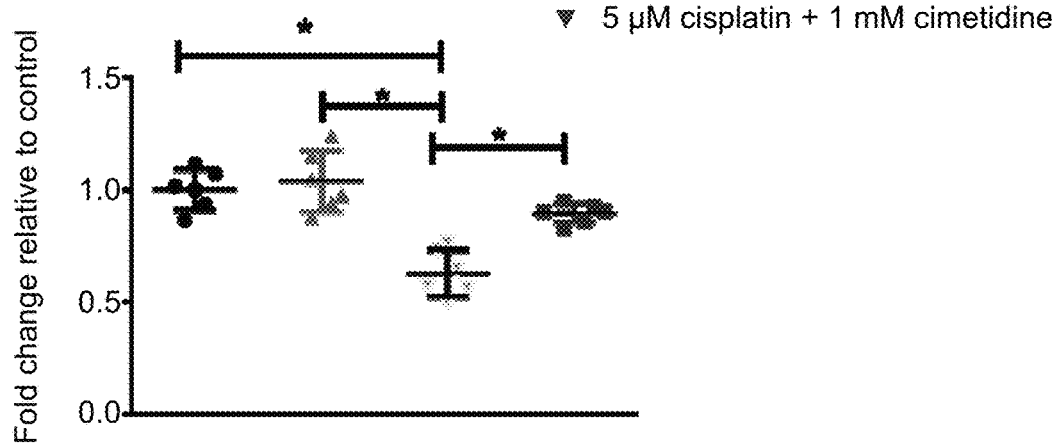
Figure 8C:
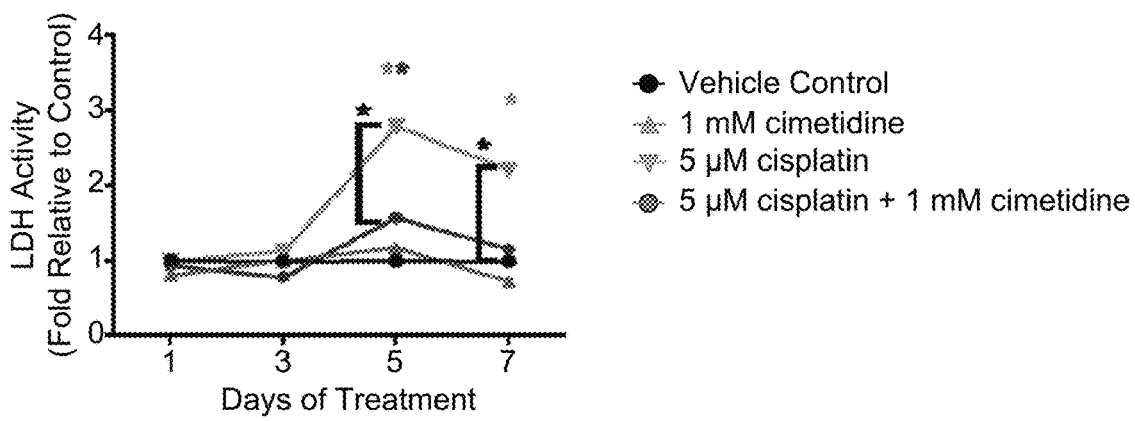

To evaluate the role of OCT2-mediated transport in the cisplatin-induced toxicity, tissues were treated with cisplatin in the presence of cimetidine, an OCT2 inhibitor. As shown in FIG. 8A, no loss of viability was observed in tissues treated with cimetidine alone compared to the vehicle control. Tissues treated with 5 µM cisplatin exhibited a nearly 50% decrease in viability (FIG. 7A and FIG. 8A), and tissues treated with a combination of cisplatin and cimetidine exhibited viability levels indistinguishable from vehicle or cimetidine-only controls. This protective effect of cimetidine was also observed in the GGT activity levels from tissues treated with cisplatin or cisplatin plus cimetidine (FIG. 8B). LDH release, indicative of toxicity, peaked at treatment day 5 in tissues treated with 5 µM cisplatin alone, with an observed 3-fold increase over vehicle controls (FIG. 8C). Tissues treated with cisplatin plus cimetidine did not exhibit the same damage response, showing only slightly elevated levels of LDH release compared to vehicle at day 5 and indistinguishable levels versus control-treated tissues by day 7 (FIG. 8C).

Figure 9A:
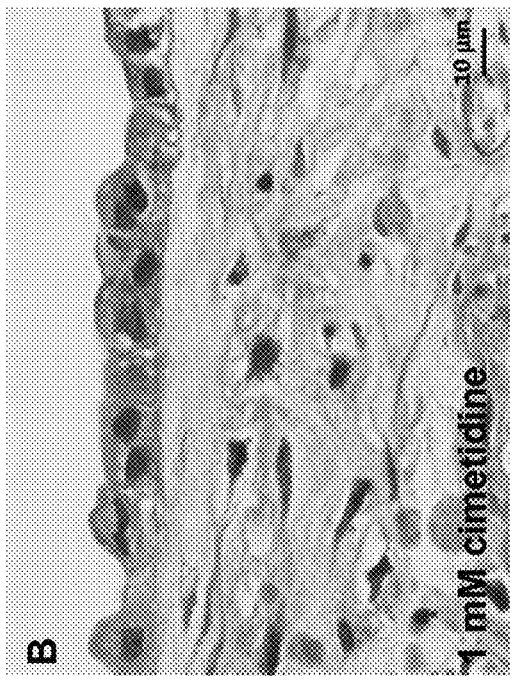
FIGS. 9A-9D are micrographs showing histological analysis of cisplatin toxicity. Representative H&E images are shown for tissues dosed daily for 7 days with vehicle (FIG. 9A), 1 mM cimetidine (FIG. 9B), 5 µM cisplatin (FIG. 9C), or 5 µM cisplatin+1 mM cimetidine (FIG. 9D).
Figure 9B:
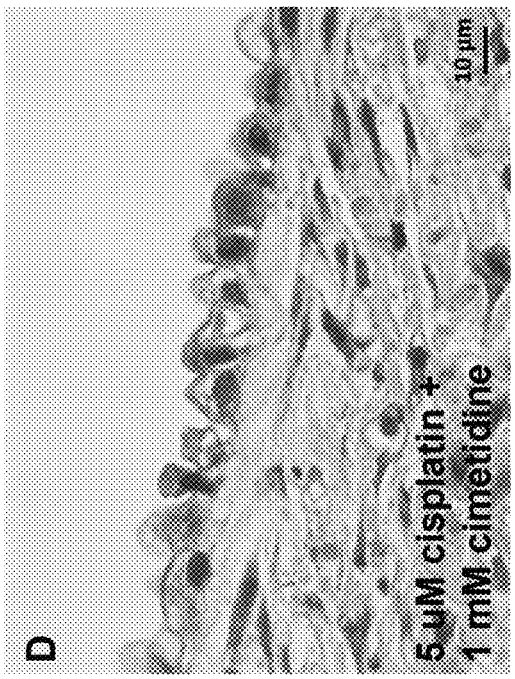
Figure 9C:
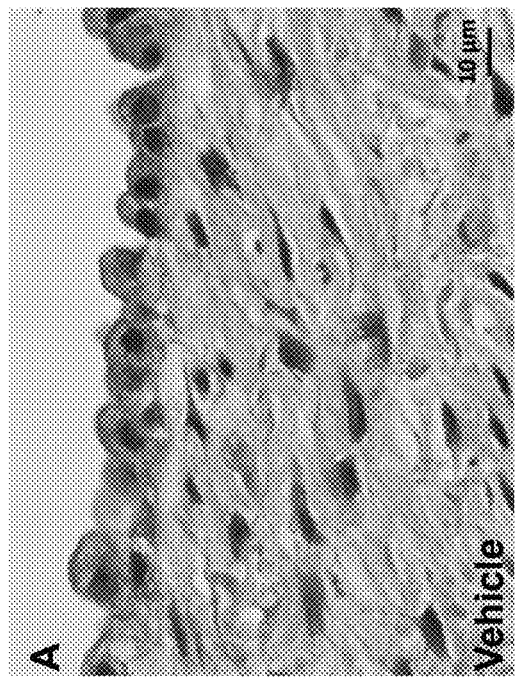
Figure 9D:
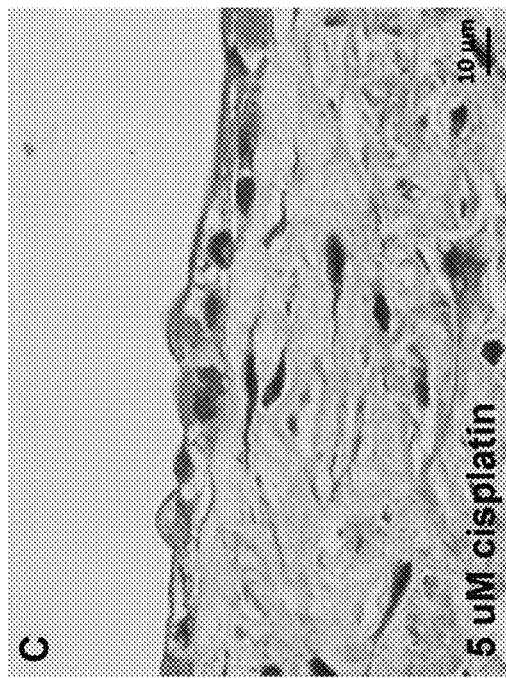
Figure 10A:
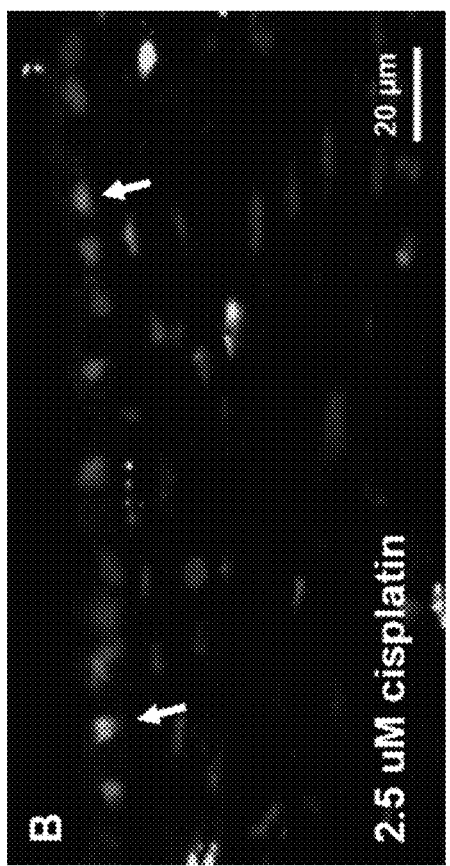
FIGS. 10A-10D are micrographs showing the proliferation of RPTEC in response to damage. Tissues were dosed daily for 7 days with vehicle (FIG. 10A), 2.5 µM cisplatin (FIG. 10B), 5 µM cisplatin (FIG. 10C), or 5 µM cisplatin+1 mM cimetidine (FIG. 10D) and stained with an antibody against proliferating cell nuclear antigen (PCNA). Proliferating cells are marked with white arrows.
Figure 10B:
Figure 10C:
Figure 10D:
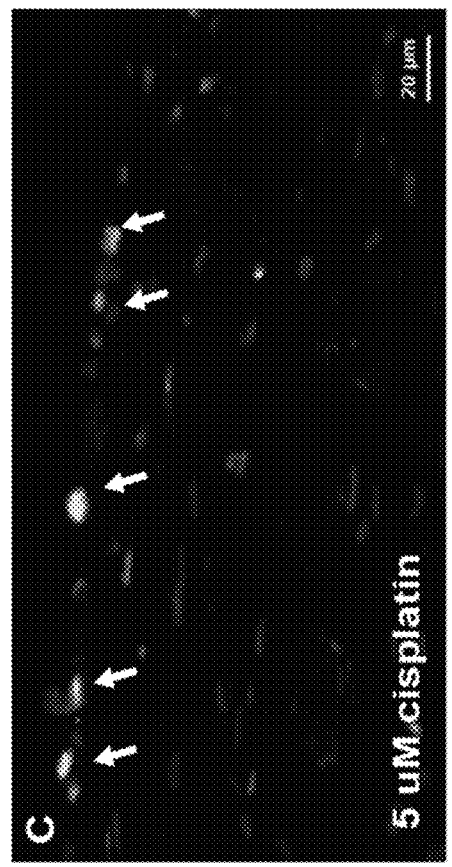
Figure 11A:
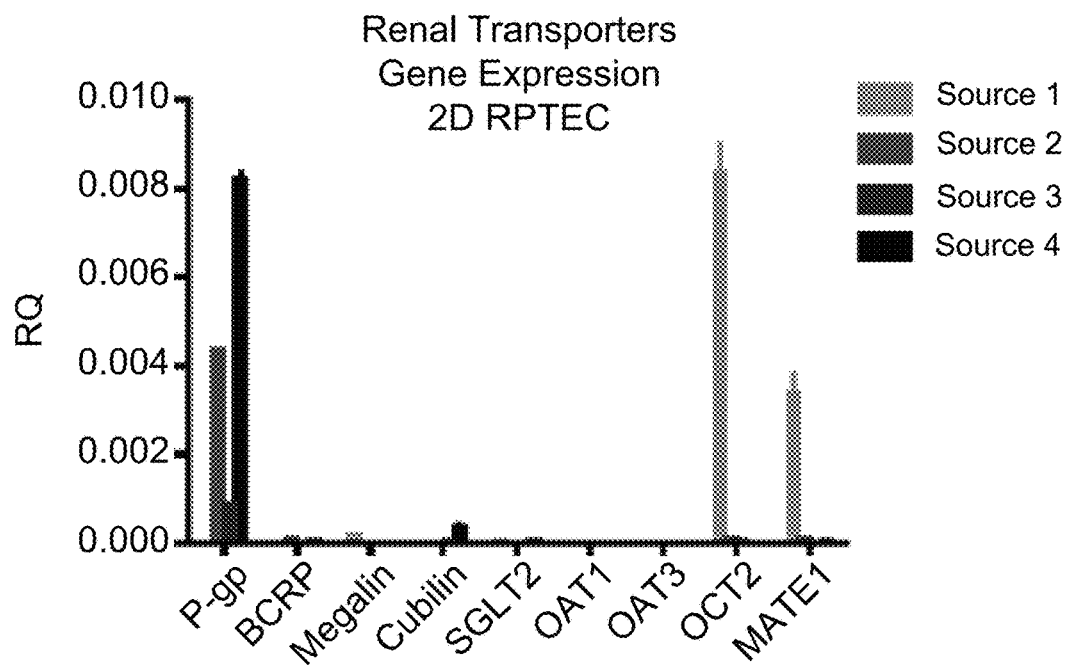
FIGS. 11A-11E are a bar graph (FIG. 11A) and micrographs showing transporter gene expression and cell morphology for 2D primary human RPTEC.
Figure 11B:
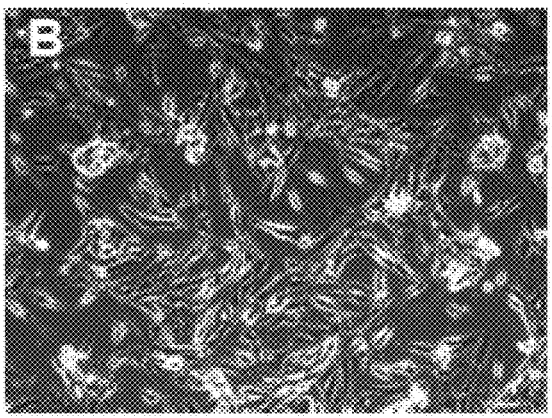
Figure 11C:
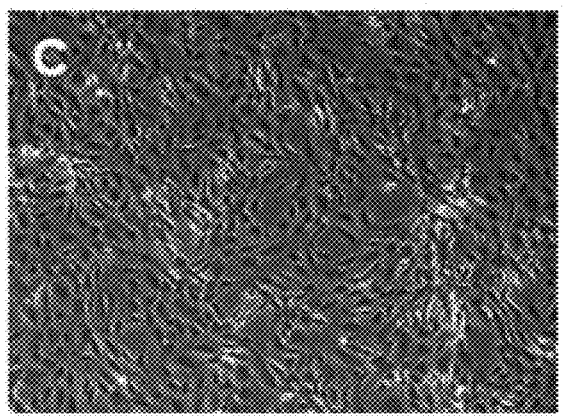
Figure 11D:
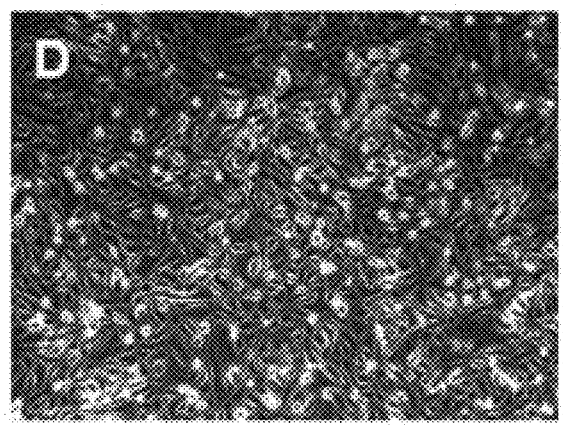
Figure 11E:
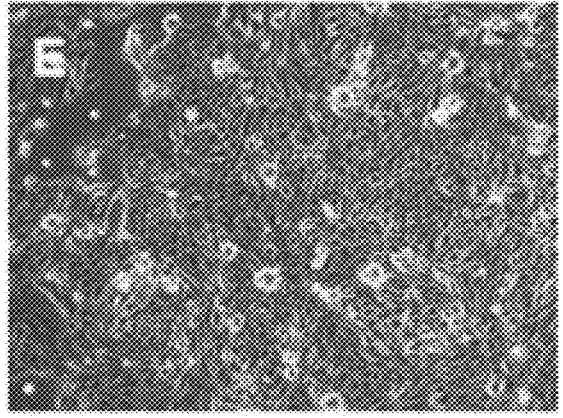

Histological analysis by H&E staining confirmed the loss of epithelial viability in response to cisplatin (FIGS. 9A-9D). Vehicle or cimetidine-only tissues exhibited healthy, columnar RPTEC with round nuclei (FIGS. 9A and B), while tissues treated with 5 µM cisplatin exhibited a more squamous morphology and loss of nuclei (FIG. 9C). Tissues treated with cisplatin plus cimetidine exhibited a substantial improvement in epithelial morphology versus cisplatin alone, with partial restoration of nuclear localization and columnar RPTEC (FIG. 9D). To evaluate RPTEC proliferation in response to damage induced by cisplatin, tissues were stained for proliferating cell nuclear antigen (PCNA). Vehicle or cimetidine-treated control tissues exhibited low levels of RPTEC proliferation; however, a dose-dependent proliferative response was observed in tissues treated with cisplatin (FIGS. 10A-10D). This increased proliferation in the RPTEC of 3D PT tissues was decreased by co-administration of cimetidine. Thus, the 3D PT tissues were able to recapitulate nephrotoxicity after exposure to clinically-relevant doses of cisplatin and confirm the role of the OCT2 transporter as a mechanism of nephrotoxicity induction.

Example 15—Assessment of Complications of Diabetes

EXVIVE Human Kidney Tissue (Organovo, San Diego, CA) is a fully human 3D bioprinted tissue comprised of an apical layer of polarized primary renal proximal tubule epithelial cells (RPTECs) supported by a collagen IV-rich tubulointerstitial interface of primary renal fibroblasts and endothelial cells. After culturing for 14 days, Healthy EXVIVE kidney tissues were either untreated (control) or were exposed to a high concentration of glucose (1000 mg/dL=10 g/L) for an additional 14 days to mimic the high levels of urine glucose seen in diabetic patients.

The tissues were then formalin fixed, embedded, sectioned, and stained with hemotoxylin and eosin (H&E) to look for changes in cellular and nuclear morphology. As shown in FIGS. 12B and 12D, high glucose treatment leads to the generation of glycogenated nuclei in the epithelial cells layer (as shown by the arrows). The glycogenated nuclei are characterized by nuclei with a "hollowed out" appearance due to the storage of glycogen, with condensation of chromatin around the nuclear membrane and the presence of a prominent nucleolus (see insert in FIG. 12D). The presence of glycogenated nuclei has been observed in diabetic patient and rodent models.

Example 15 shows that an isolated, 3D printed proximal tubule disorder model can be successfully induced to exhibit the desired phenotype without the proximal tubule's usual support system inducing this phenotype. The usual support system of the proximal tubules would include, by way of example, the glomeruli, the Bowman's capsule, and the surrounding perfusion system for the proximal tubules. In a diabetic patient, high concentrations of glucose may accumulate in the glomeruli, which may gradually contribute to the dysfunction of the glomeruli. This gradual dysfunction of the glomeruli eventually results in a leakage of excess glucose into the proximal tubules. As such, the proximal tubules may begin to develop an acute or chronic diabetic disorder displaying the presence of a glycogenated nuclei. Example 15 also displays the presence of glycogenated nuclei, which shows that an isolated, 3D bioprinted proximal tubule disorder model can be successfully induced to exhibit the desired disorder phenotype without the proximal tubule's usual support system inducing this phenotype.

Example 16—Assessment of Crystalline Deposits

Healthy EXVIVE kidney tissues were either untreated (control) or exposed to a nephrotoxic agent.

Figure 13C:
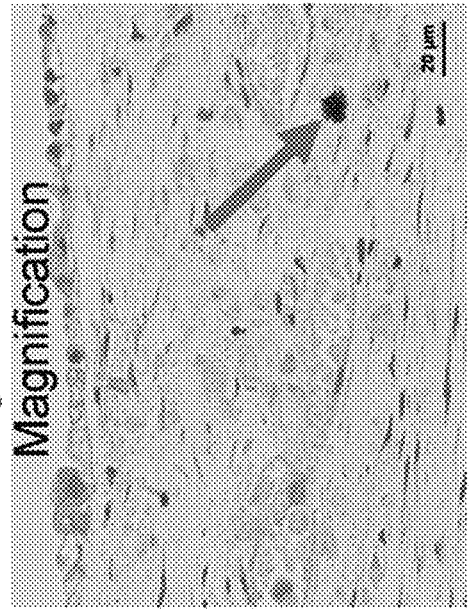
FIGS. 13A-13C are micrographs showing the histological characterization of EXVIVE kidney tissues.
Figure 13A:
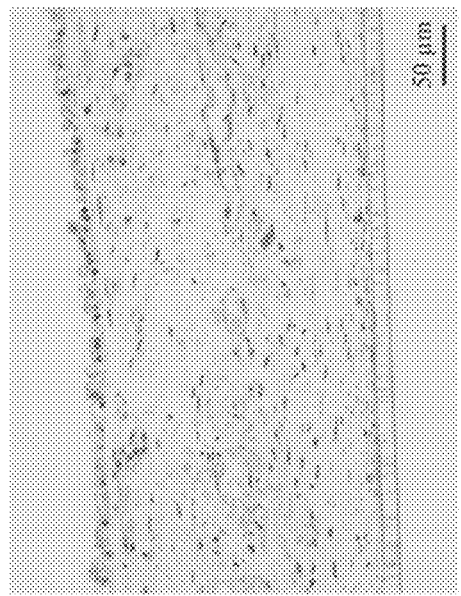
Figure 13B:
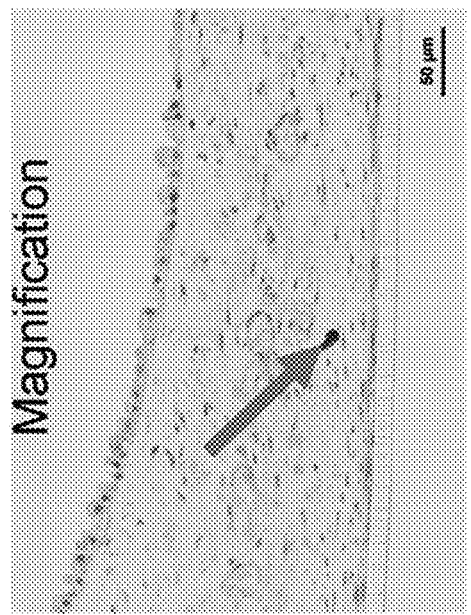

The tissues were then formalin fixed, embedded, sectioned, and then stained to look for calcium oxalate deposits. Calcium oxalate is a known component of kidney stones. As shown in FIGS. 13B and 13C, exposure of the kidney tissues to a nephrotoxic agent produces treatment-dependent deposits (as shown by the arrows).

Example 17—Renal Fibrosis—EXVIVE Human Kidney Tissue Treated with TGFβ

Figure 14A:
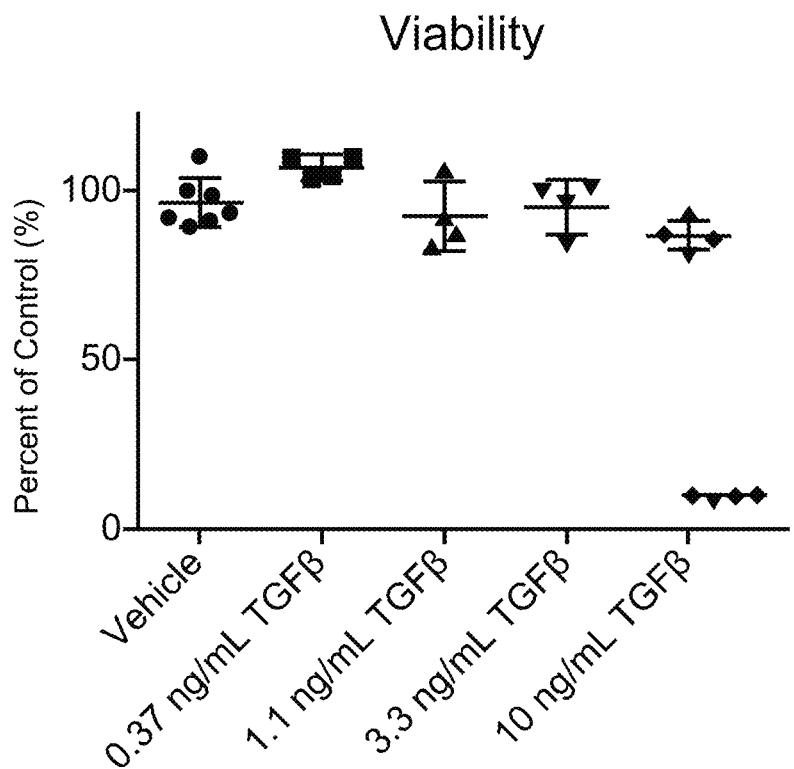
FIGS. 14A-14B are graphs that depict viability and the epithelial cell functions in a Renal Fibrosis-induced EXVIVE Human Kidney Tissue that was treated with TGFβ.
Figure 14B:
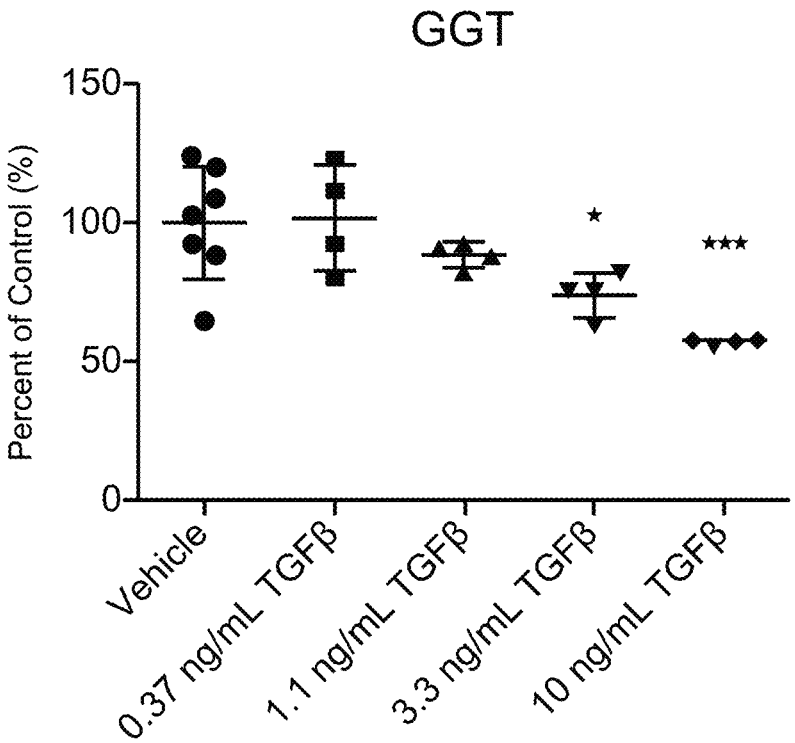

As described in this present disclosure, the EXVIVE Human Kidney Tissue (Organovo, San Diego, CA) is a fully human three-dimensional (3D), bioprinted tissue comprised of an apical layer of polarized primary renal proximal tubule epithelial cells (RPTECs) supported by a collagen IV-rich tubulointerstitial interface of primary renal fibroblasts and endothelial cells. As renal fibrosis is a common downstream effect of drug-induced injury, the EXVIVE Human Kidney Tissue was treated with Transforming Growth Factor β (TGFβ or TGFbeta), a key player of the fibrotic response, for purposes of evaluating tubulointerstitial fibrosis. Thus, to induce renal fibrosis, a healthy EXVIVE Human Kidney Tissue was treated with TGFβ, a key player of the fibrotic response. In particular, each healthy EXVIVE Human Kidney Tissue was dosed daily for seven days with vehicle control, 0.37 ng/ml TGFβ, 1.1 ng/ml TGFβ, 3.3 ng/ml TGFβ, or 10 ng/ml TGFβ, respectively. Subsequently, after the EXVIVE Human Kidney Tissue was treated with TGFβ, an assessment of the viability and epithelial cell functions of this EXVIVE Human Kidney Tissue was conducted. FIG. 14A shows the analysis of Resazurin conversion as measure of overall tissue metabolic activity and cell health. No statistically significant differences were detected between treatment groups. FIG. 14B shows the analysis of gamma glutamyl transfer (GGT) activity as a measure of epithelial cell function. Statistically significant reduction in RPTEC function was detected with higher doses of TGFβ. Data shown is the average of 3 tissue samples per condition and is represented as the fold change relative to the vehicle control. *p<0.05; ***p<0.001 for each condition compared to vehicle control.

Figure 15:
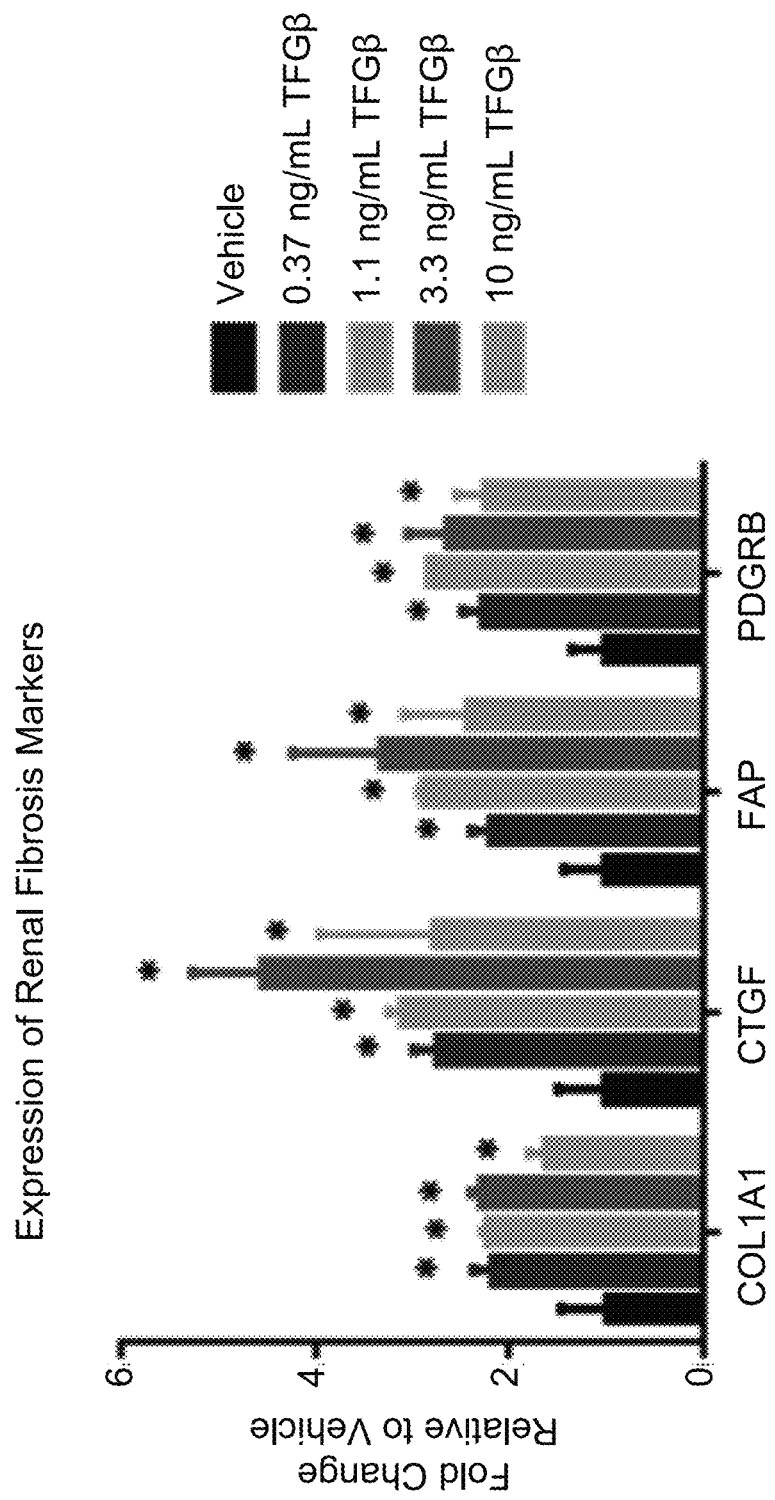
FIG. 15 is a bar graph that shows in the EXVIVE Human Kidney Tissue treated with TGFβ, TGFβ induces fibrosis-related gene expression.

Fibrosis-related gene expression was also assessed on this EXVIVE Human Kidney Tissue treated with TGFβ. FIG. 15 shows gene expression analysis by semi-quantitative RTPCR showed induction of the fibrotic markers collagen I (COL1A1), connective tissue growth factor (CTGF), fibroblast-activating protein (FAP), or platelet-derived growth factor receptor beta (PDGFRB). Data shown is the average of 3 tissue samples per condition. *p<0.0001 for each condition compared to vehicle control.

Figure 16F:
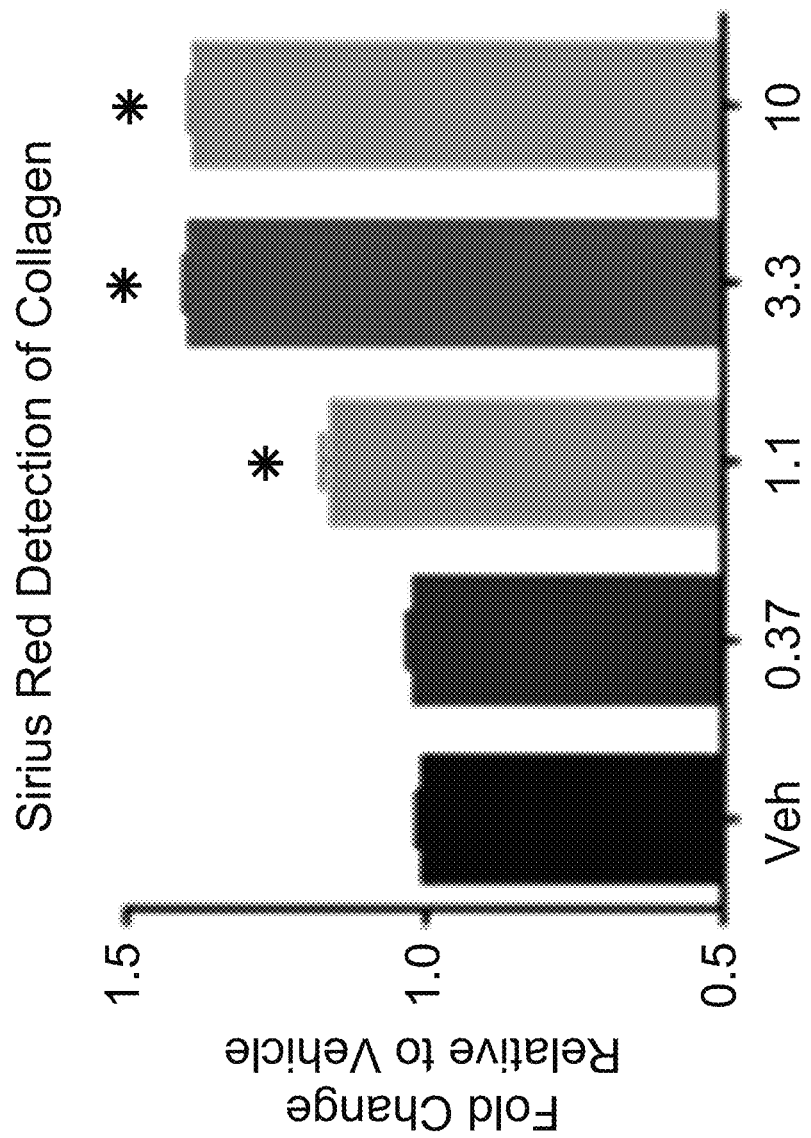
FIG. 16F is a bar graph that shows in the EXVIVE Human Kidney Tissue treated with TGFβ, TGFβ induces tissue thickening and increased extracellular matrix deposition.

In the EXVIVE Human Kidney Tissue treated with TGFβ, it was also shown that TGFβ induces tissue thickening and increased extracellular matrix deposition. FIG. 16A shows representative Gomori's Trichrome stains for ECM deposition. As shown in FIG. 16A, increased TGFβ induced an increase in the extracellular matrix deposition. FIG. 16B shows quantification of Sirius red-stained collagen in tissue sections. Data represents the average of 4 technical replicates per tissue, 3 tissues per condition and is represented as the fold change relative to the vehicle control following normalization to total protein content as measured by Fast Green staining. *p<0.05 for each condition compared to vehicle control.

Example 17 (FIGS. 14-16) show that renal interstitial fibrosis can be induced in the EXVIVE Human Kidney Tissue by treating with TGFβ. Following treatment of EXVIVE Human Kidney Tissue with TGFβ for 7 days, an increase in the expression of fibrosis-related genes (FIG. 15), extensive ECM deposition in the interstitium (FIG. 16A), and loss of epithelial cell function at the highest dose (FIG. 14B) were shown. This is a significant technical advancement in the state-of-the-art because these results demonstrate the extended capabilities of the EXVIVE Human Kidney Tissue to mount measurable responses at the biochemical, transcriptional, and histological levels consistent with renal injury and interstitial fibrosis, a disease phenotype not achievable in traditional systems of epithelial cell monolayer culture with limited longevity. The EXVIVE Human Kidney Tissue could therefore enable applications aimed at understanding mechanisms of disease progression, evaluating drug-induced renal fibrosis, and investigation of intervention strategies toward the development of novel anti-fibrotic drugs.

Example 18—EXVIVE Human Kidney Tissue Treated with Cisplatin

Cisplatin was used to induce nephrotoxicity. As previously described in FIGS. 7-10, cisplatin can induce nephrotoxicity. Each healthy EXVIVE Human Kidney Tissue was dosed daily with 5, 10, or 25 µM cisplatin, respectively. As described in this present disclosure, the EXVIVE Human Kidney Tissue (Organovo, San Diego, CA) is a fully human three-dimensional (3D), bioprinted tissue comprised of an apical layer of polarized primary renal proximal tubule epithelial cells (RPTECs) supported by a collagen IV-rich tubulointerstitial interface of primary renal fibroblasts and endothelial cells.

Figure 17:
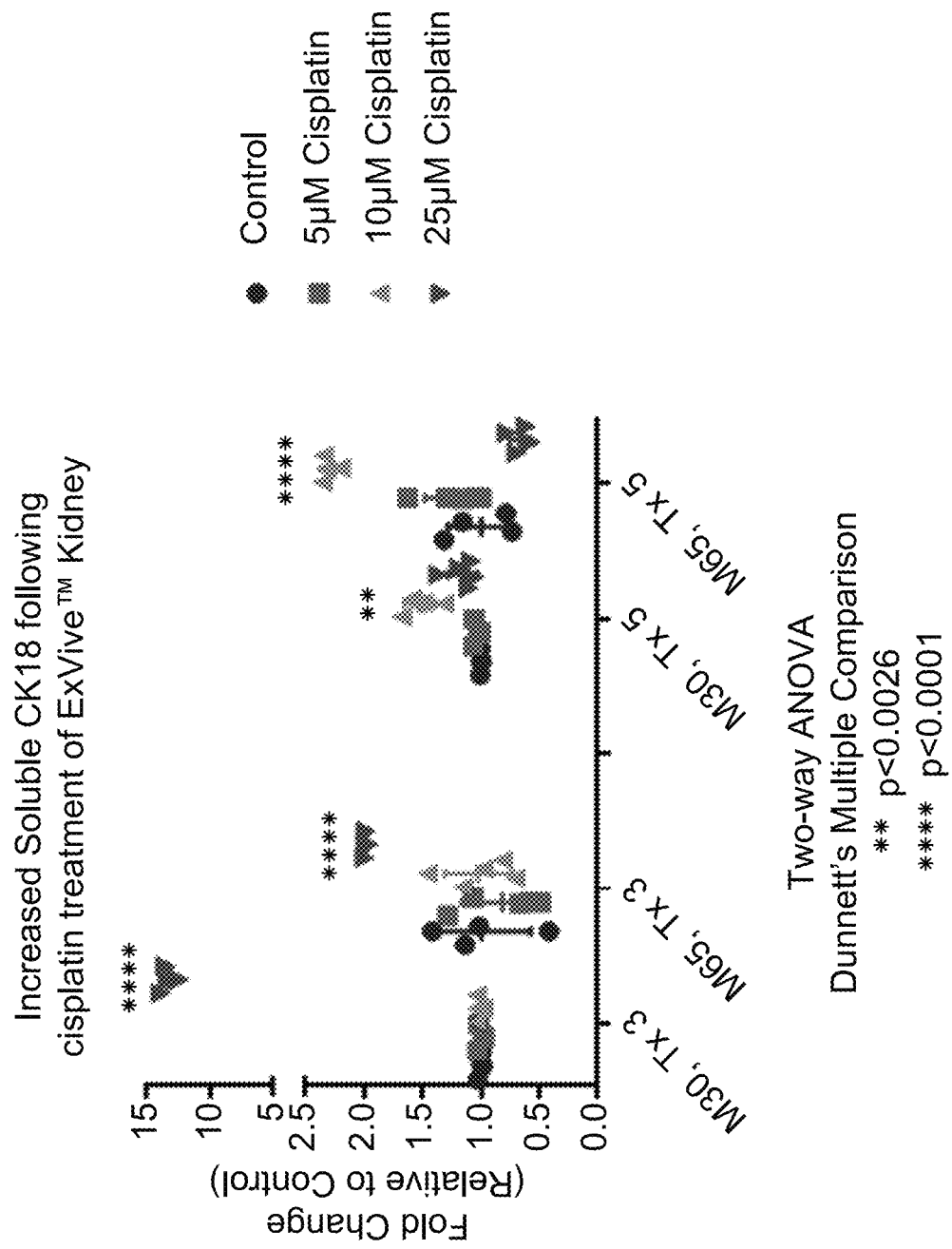
FIG. 17 is a micrograph that show increased soluble cytokeratin 18 (CK18) following cisplatin treatment with the EXVIVE Human Kidney Tissue.

Following treatments (Tx) 3 and 5, media supernatants were collected and analyzed for cytokeratin 18 fragments M30 and M65, as shown in FIG. 17. As shown in FIG. 17, there was increased soluble CK18 following cisplatin treatment of the EXVIVE Human Kidney Tissue. Cytokeratin 18 (CK18) is a surface marker produced in epithelial cells. Secreted cleavage products from CK18 differ based on the mechanism of cell death and can be measured from spent media samples with solid-phase sandwich enzyme ELISA (Diapharma, West Chester, OH). The M30 CK18 fragment is produced by enzymatic caspase activity stemming from apoptosis, while the M65 CK18 fragment is released from dead cells (apoptotic and necrotic). This ELISA assay provides the ability to distinguish the magnitude of an epithelial specific injury within in tissue comprised of multiple cell types. In tandem, M30 and M65 helps to determine mechanism of epithelial cell death.

Example 19—Detection of Transporter Protein Expression in EXVIVE Human Kidney Tissue FIGS. 18A-I show human renal cortex samples (KT1 and KT2), EXVIVE Human Kidney Tissue (3D-1 and 3D-2), and plated 2D RPTEC cells (2D RPTEC lot 1105) were analyzed for transporter expression by LC-MS/MS. As described in this present disclosure, the EXVIVE Human Kidney Tissue (Organovo, San Diego, CA) is a fully human three-dimensional (3D), bioprinted tissue comprised of an apical layer of polarized primary renal proximal tubule epithelial cells (RPTECs) supported by a collagen IV-rich tubulointerstitial interface of primary renal fibroblasts and endothelial cells. Peptides unique for each transporter were selected based on in silico selection criteria. Total membrane isolation was performed on tissue/cell samples prior to analysis. Each bar represents transporter peptide peak area normalized to total sample protein and to spiked human serum albumin internal standard. Note that FIGS. 18A-I describe protein expression of transporters, whereas FIG. 11 describes gene expression of transporters.

All transporters analyzed were detectable in renal cortex samples, EXVIVE Human Kidney Tissue, and plated 2D RPTECs. The transporters measured are critical for drug disposition within the human kidney. As a result, these transporters have been identified by regulatory approval bodies, such as the United States Food and Drug Administration (FDA) and the European Medicines Agency (EMA) as critical transporters to evaluate for drug safety in the human kidney.

DISCUSSION

To date, very few systems have been developed to study the human renal tubulointerstitial interface in vitro. A variety of systems for 3D culture of RPTEC in isolation have been developed, including culturing cells in MATRIGEL, culturing cells as organoids on a variety of scaffolds such as hyaluronic acid or silk, and culture of RPTEC in microfluidic devices ("kidney on a chip") (Joraku et al., 2009; Subramanian et al., 2010; Astashkina et al., 2012; Jang et al., 2013). However, these systems lack direct contact between the epithelium and relevant interstitial cell types, including fibroblasts and endothelial cells, that play both a structural role in orienting the epithelium as well as providing a source of growth factors critical for the continued health and organization of the epithelium (Lemley and Kriz, 1991; Kaissling and Le Hir, 2008; Meran and Steadman, 2011). Without these supportive cell types, RPTEC rapidly lose their native phenotype in culture, thus preventing the ability to perform the chronic, low dose exposure studies necessary to predict how a molecule will perform in the clinic. The goal of this study was to use 3D bioprinting to build and characterize a model in which a renal interstitium supported the continued growth and maintenance of healthy epithelia. The renal fibroblasts and endothelial cells provided a robust source of endogenously-produced extracellular matrix, which enabled tissue formation without the use of exogenous scaffolding as well as supported the formation of open networks of endothelial cells in the interstitial layer and a collagen-rich basement membrane underlying the epithelium. The endothelial networks form open spaces in the interstitium that may allow better access of media and nutrients to the entirety of the tissue. While the interstitial layer is thicker than the native human renal interstitium, the combination of the renal fibroblasts with the endothelial cells does enable a cellular density more reminiscent of the in vivo tissue, which contains fibroblast-like cells immediately adjacent to the epithelium (Lemley and Kriz, 1991).

3D PT tissues were evaluated for their ability to recapitulate physiologically-relevant aspects of the in vivo proximal tubule, including reconstitution of the intrarenal RAS and barrier functions. The human PT expresses ACE at the apical surface of RPTEC in order to convert angiotensin I to angiotensin II (Schulz et al., 1988; Ichihara et al., 2004), which then plays a critical role in regulating sodium transport to influence hypertension through feedback onto the renal microvasculature and glomerulus (Kobori et al., 2007). The 3D PT model was able to demonstrate angiotensin II conversion in response to angiotensin I stimulation (FIG. 4B). Future experiments exploring the RAS in the 3D PT model could potentially be used to separate the effects of new therapeutics for hypertension on the glomerulus versus the PT, particularly with regard to mitigating nephrotoxicity as a result of hypertension. Another important function of the PT is to serve as an epithelial barrier controlling the movement of specific types of molecules across the monolayer. The PT is the primary site of re-uptake of water and solutes following glomerular filtration, and as such, must form a more permeable barrier than that observed more distally in the nephron (Ussing et al., 1974; Greger, 1996). Monolayer cultures of renal epithelial such as LLC-PK1 and MDCK cells have been shown to exhibit higher TEER values of 100-200 $\Omega$*cm2, while in vivo tubules exhibit values between 6.6 and 11.6 $\Omega$*cm2 (Boulpaep and Seely, 1971; Liang et al., 1999). In this study, 3D PT tissues exhibited TEER values of 18.1 $\Omega$*cm2 (Table 3), which more closely matches values measured in vivo for PT barrier formation. Monolayer epithelial cultures with tight barrier function and high TEER values (>100 $\Omega$*cm2) exhibit a Papp of $0.5-1\times10^{-6}$ cm/s for Lucifer yellow (Tran et al., 2004). The average Papp value for Lucifer yellow in 3D PT tissues was $2.97\times10^{-6}$ cm/s, indicating transcellular or paracellular transport through the tissues and confirming the leaky barrier function noted by TEER measurements (Table 3). One possible cause for this is the presence of the extracellular matrix-rich interstitium underlying the RPTEC, which may support the formation of a leaky barrier through formation of a physiologically-relevant basement membrane structure.

Primary human RPTEC provide the advantage of expressing a variety of transporters known to play a role in drug-induced kidney injury; however, these cells can be cultured for a limited time (<14 days) before undergoing senescence or epithelial to mesenchymal transition and concomitant loss of renal transporter expression and function (FIGS. 11A-11E). In contrast, culturing these cells in a 3D context on an interstitial layer enabled retention of epithelial cell viability and function for at least 30 days in culture while retaining gene expression of many renal transporters such as cubilin and megalin, MATE1 and MATE2K, OCT2, BCRP, and P-gp (Tables 1 and 5). Furthermore, polarized distribution and functional activity of P-gp and SGLT2 were confirmed in 3D PT tissues by transport of a glucose analog and R123, respectively (FIGS. 5A-B and FIGS. 6A-6E). The continued expression and function of renal transporters in the 3D PT tissues allows the possibility of performing chronic dosing studies to assess human nephrotoxicity coupled with detailed analysis of molecular mechanisms of action.

A human 3D multi-cellular renal tissue composed of distinct epithelial and interstitial cell compartments provides a unique test platform for evaluating new drug entities for potential nephrotoxicity, allowing for the assessment of biochemical, transcriptional, and histological endpoints across multiple cell types and anatomical locations ex vivo. To provide initial proof-of-concept data that this model may be used for nephrotoxicity testing, 3D PT tissues were exposed to the classical nephrotoxin cisplatin. 3D PT tissues exhibited an LD50 value of 5.72 µM (FIG. 7A), consistent with previously reported values for in vitro and ex vivo cisplatin toxicity (Tay et al., 1988; Katsuda et al., 2010). While several mechanisms likely play a role in cisplatin-mediated nephrotoxicity, including generation of reactive oxygen species and creation of toxic intermediates through glutathione conjugation, these mechanisms occur after cisplatin has been taken up by RPTECs (Hanigan and Devarajan, 2003). This uptake is thought to occur primarily through the action of the OCT2 renal transporter, although other transporters such as the copper transporters (CTR1 and 2) may play a role as well (Ciarimboli et al., 2005). In the current study, inhibition of the OCT2 transporter by cimetidine successfully protected against cisplatin-induced loss of viability and epithelial function (FIGS. 8A-8C and FIGS. 9A-9D). This mechanism is clinically relevant, as polymorphisms in OCT2 that influence its function are predictive of cisplatin-induced AKI, and animal models that lack OCT2 expression exhibit decreased sensitivity to cisplatin (Ciarimboli et al., 2005; Ciarimboli et al., 2010). In response to AKI, the PT epithelium has demonstrated a high capacity for compensatory proliferation and repopulation in vivo (Nadasdy et al., 1994). Analogously, we observed a dose-dependent increase in proliferating RPTEC in 3D PT tissues exposed to cisplatin, which was reduced in tissues treated with cimetidine (FIGS. 10A-10D). In humans, cimetidine therapy or the presence of loss-of-function mutations in OCT2 correlated with decreased urinary cystatin C following cisplatin administration, demonstrating the possible utility of this therapy as an ameliorative during chemotherapy (Zhang and Zhou, 2012).

In summary, we have designed and validated a new in vitro human 3D tissue model capable of preserving RPTEC function over an extended time in culture and enabling quantitative detection of PT nephrotoxicity occurring by specific mechanisms. These data suggest that 3D PT tissues could positively impact the pre-clinical drug discovery pipeline, helping to prevent costly failures in late stage clinical trials. Use of primary human RPTECs from multiple donors, including those from patients with acute or chronic kidney disease, may enable better understanding of how drugs may perform clinically across a specific patient population. Additional studies across a panel of nephrotoxic compounds with differing mechanisms of action will help to further elucidate the value of the system for screening new chemical entities. The inclusion of a tubulointerstitial interface in the model allows for exploration of complex, multifactorial disease processes like fibrosis, as well as assessing the capacity of the RPTEC to repopulate and regenerate during or after drug-induced injury. In addition, the system may enable the parallel investigation of biomarkers that may be useful in noninvasively detecting early kidney injury.

ABBREVIATIONS 3D, three-dimensional; ACE, angiotensin-converting enzyme; AGT, angiotensinogen; AGTR1, angiotensin receptor type I; AKI, acute kidney injury; DPBS, Dulbecco's phosphate buffered saline; H&E, hematoxylin and eosin; HUVEC, human umbilical vein endothelial cell; LDH, lactate dehydrogenase; OCT, organic cation transporter; Papp, passive permeability; PCNA, proliferating cell nuclear antigen; PT, proximal tubule; R123, rhodamine 123; RAS, renin-angiotensin system; RFU, relative fluorescence units; RPTEC, renal proximal tubule epithelial cell; TEER, transepithelial electrical resistance.

REFERENCE CITATIONS

Astashkina, A. I., Mann, B. K., Prestwich, G. D., and Grainger, D. W. (2012). A 3-D organoid kidney culture model engineered for high-throughput nephrotoxicity assays. *Biomaterials* 33(18), 4700-4711. doi: 10.1016/j.biomaterials.2012.02.063.

Baer, P. C., Wegner, B., and Geiger, H. (2004). Effects of mycophenolic acid on IL-6 expression of human renal proximal and distal tubular cells in vitro. *Nephrol. Dial. Transplant* 19, 47-52.

Banu, N. and Meyers, C. M. (1999). IFN-gamma and LPS differentially modulate class II MHC and B7-1 expression on murine renal tubular epithelial cells. *Kidney Int.* 55(6), 2250-2263.

Basile, D. P., Rovak, J. M., Martin, D. R., and Hammerman, M. R. (1996). Increased transforming growth factor-beta 1 expression in regenerating rat renal tubules following ischemic injury. *Am. J. Physiol.* 270(3), F500-F509.

Boulpaep, E. L., and Seely, J. F. (1971). Electrophysiology of proximal and distal tubules in the autoperfused dog kidney. *Am. J. Physiol.* 221(4), 1084-1096.

Brenner, B. M. (2008). Brenner and Rector's The Kidney. Philadelphia, PA: Saunders Elsevier.

Bryant, D. M., and Mostov, K. E. (2008). From cells to organs: building polarized tissue. *Nat. Rev. Mol. Cell. Biol.* 9(11), 887-901. doi: 10.1038/nrm2523.

Chen, Y., Zhang, J., Li, J., Zhao, T., Zou, L, Tang, Z., Zhang, X., and Wu, Y. (2006). Roles of toll-like receptors in C—C chemokine production by renal tubular epithelial cells. *J. Immunol.* 169, 2016-2033.

Choudhury, D., and Ahmed, Z. (2006). Drug-associated renal dysfunction and injury. *Nat. Clin. Pract. Nephrol.* 2(2), 80-91. doi: 10.1038/ncpneph0076.

Ciarimboli, G., Deuster, D., Knief, A., Sperling, M., Holtkamp, M., Edemir, B., et al. (2010). Organic cation transporter 2 mediates cisplatin-induced oto- and nephrotoxicity and is a target for protective interventions. *Am. J. Pathol.* 176(3), 1169-1180. doi: 10.2353/ajpath.2010.090610.

Ciarimboli, G., Ludwig, T., Lang, D., Pavenstadt, H., Koepsell, H., Piechota, H. J., et al. (2005). Cisplatin nephrotoxicity is critically mediated via the human organic cation transporter 2. *Am. J. Pathol.* 167(6), 1477-1484. doi: 10.1016/50002-9440(10)61234-5.

Clarke, L. L. (2009). A guide to Ussing chamber studies of mouse intestine. *Am J Physiol Gastrointest Liver Physiol* 296(6), G1151-1166. doi: 10.1152/ajpgi.90649.2008.

Farris A. B., Adams C. D., Brousaides N., Della Pelle P. A., Collins A. B., Moradi E., Smith R. N., Grimm P. C., and Colvin R. B. (2011). Morphometric and visual evaluation of fibrosis in renal biopsies. *J. Am. Soc. Nephrol.* 22(1), 176-86. doi: 10.1681/ASN.2009091005.

Farris, A. B., Colvin, R. B. (2012). Renal interstitial fibrosis: Mechanisms and Evaluation. *Curr. Opin. Nephrol. Hypertens.* 21(3), 289-300. doi:10.1097/MNH.0b013e3283521cfa.

Ferrell, N., Ricci, K. B., Groszek, J., Marmerstein, J. T., and Fissell, W. H. (2012). Albumin handling by renal tubular epithelial cells in a microfluidic bioreactor. *Biotechnol. Bioeng.* 109(3), 797-803. doi:10.1002/bit.24339.

Forgacs, G., Jakab, K., Neagu, A., and Mironov, V. (2012). Self-assembling cell aggregates and methods of making engineered tissue using the same. United States patent application 2012/0288938.

Gesualdo, L., Ranieri, E., Monno, R., Rossiello, M. R., Colucci, M., Semeraro, N., Grandaliano, G., and Schena, F. P. (1999). Angiotensin IV stimulates plasminogen activator inhibitor-1 expression in proximal tubular epithelial cells. *Kidney Int.* 56, 461-470.

Godoy, P., Hewitt, N. J., Albrecht, U., Andersen, M. E., Ansari, N., Bhattacharya, S., et al. (2013). Recent advances in 2D and 3D in vitro systems using primary hepatocytes, alternative hepatocyte sources and non-parenchymal liver cells and their use in investigating mechanisms of hepatotoxicity, cell signaling and ADME. *Arch. Toxicol.* 87(8), 1315-1530. doi: 10.1007/s00204-013-1078-5.

Granata, S., Gassa, A. D., Tornei, P., Lupo, A., and Zaza, G. (2015). Mitochondria: a new therapeutic target in chronic kidney disease. *Nutrition & Metabolism* 12:49.

Greger, R. (1996). "Comprehensive Human Physiology: From Cellular Mechanisms to Integration," ed. R.a.W. Greger, U. (Heidelberg: Springer-Verlag).

Griffith, L. G., Wells, A., and Stolz, D. B. (2014). Engineering liver. *Hepatology* 60(4), 1426-1434. doi: 10.1002/hep.27150.

Guinee, D. G., Jr., van Zee, B., and Houghton, D. C. (1993). Clinically silent progressive renal tubulointerstitial disease during cisplatin chemotherapy. *Cancer* 71(12), 4050-4054.

Hanigan, M. H., and Devarajan, P. (2003). Cisplatin nephrotoxicity: molecular mechanisms. *Cancer Ther.* 1, 47-61.

Ichihara, A., Kobori, H., Nishiyama, A., and Navar, L. G. (2004). Renal renin-angiotensin system. *Contrib. Nephrol.* 143, 117-130.

Ishikura, H., Takahashi, C., Kanagawa, K., Hirata, H., Imai, K., and Yoshiki, T. (1991). Cytokine regulation of ICAM-1 expression on human renal tubular epithelial cells in vitro. *Transplantation* 51(6), 1272-1275.

Jakab, K., Norotte, C., Damon, B., Marga, F., Neagu, A., Besch-Williford, C. L., et al. (2008). Tissue engineering by self-assembly of cells printed into topologically defined structures. *Tissue Eng. Part A* 14(3), 413-421. doi: 10.1089/tea.2007.0173.

Jakab, K., Norotte, C., Marga, F., Murphy, K., Vunjak-Novakovic, G., and Forgacs, G. (2010). Tissue engineering by self-assembly and bio-printing of living cells. *Biofabrication* 2(2), 022001. doi: 10.1088/1758-5082/2/2/022001.

Jang, K. J., Mehr, A. P., Hamilton, G. A., McPartlin, L. A., Chung, S., Suh, K. Y., et al. (2013). Human kidney proximal tubule-on-a-chip for drug transport and nephrotoxicity assessment. *Integr. Biol. (Camb)* 5(9), 1119-1129. doi: 10.1039/c3ib40049b.

Joraku, A., Stern, K. A., Atala, A., and Yoo, J. J. (2009). In vitro generation of three-dimensional renal structures. *Methods* 47(2), 129-133. doi: 10.1016/j.ymeth.2008.09.005.

Kaissling, B., and Le Hir, M. (2008). The renal cortical interstitium: morphological and functional aspects. *Histochem. Cell Biol.* 130(2), 247-262. doi: 10.1007/s00418-008-0452-5.

Kamiie, J., Ohtsuki, S., Iwase, R., Ohmine, K., Katsukura, Y., Yanai, K., et al. (2008). Quantitative atlas of membrane transporter proteins: development and application of a highly sensitive simultaneous LC/MS/MS method combined with novel in-silico peptide selection criteria. *Pharm. Res.* 25, 1469-1483.

Katsuda, H., Yamashita, M., Katsura, H., Yu, J., Waki, Y., Nagata, N., et al. (2010). Protecting cisplatin-induced nephrotoxicity with cimetidine does not affect antitumor activity. *Biol. Pharm. Bull.* 33(11), 1867-1871.

King, S. M., Quartuccio, S. M., Vanderhyden, B. C., and Burdette, J. E. (2013). Early transformative changes in normal ovarian surface epithelium induced by oxidative stress require Akt upregulation, DNA damage and epithelial-stromal interaction. *Carcinogenesis* 34(5), 1125-1133. doi: 10.1093/carcin/bgt003.

Kleinknecht, D., Landais, P., and Goldfarb, B. (1987). Drug-associated acute renal failure. A prospective collaborative study of 81 biopsied patients. *Adv. Exp. Med. Biol.* 212, 125-128.

Kobori, H., Nangaku, M., Navar, L. G., and Nishiyama, A. (2007). The intrarenal renin-angiotensin system: from physiology to the pathobiology of hypertension and kidney disease. *Pharmacol. Rev.* 59(3), 251-287. doi: 10.1124/pr.59.3.3.

Kumar, S. (2004). *Chapter 2: Measurement of caspase activity in cells undergoing apoptosis.* Methods in Molecular Biology, vol. 228. Totowa, NJ: Humana Press Inc.

Kunz-Schughart, L. A., Schroeder, J. A., Wondrak, M., van Rey, F., Lehle, K., Hofstaedter, F., et al. (2006). Potential of fibroblasts to regulate the formation of three-dimensional vessel-like structures from endothelial cells in vitro. *Am. J. Physiol. Cell Physiol.* 290(5), C1385-1398. doi: 10.1152/ajpcell.00248.2005.

Lemley, K. V., and Kriz, W. (1991). Anatomy of the renal interstitium. *Kidney Int.* 39(3), 370-381.

Li, D., Zou, L., Feng, Y., Xu, G., Gong, Y., Zhao, G., Ouyang, W., Thurman, J. M., and Chao, W. (2016). Complement factor B production in renal tubular cells and its role in sodium transporter expression during polymicrobial sepsis. *Crit. Care Med.* 44(5), e289-e299.

Li, W., Hartwig, S., and Rosenblum, N. D. (2014). Developmental origins and functions of stromal cells in the normal and diseased mammalian kidney. *Dev. Dyn.* 243 (7), 853-863. doi: 10.1002/dvdy.24134.

Liang, M., Ramsey, C. R., and Knox, F. G. (1999). The paracellular permeability of opossum kidney cells, a proximal tubule cell line. *Kidney Int.* 56(6), 2304-2308. doi: 10.1046/j.1523-1755.1999.00787.x.

Lin, Z., and Will, Y. (2012). Evaluation of drugs with specific organ toxicities in organ-specific cell lines. *Toxicol. Sci.* 126(1), 114-127. doi: 10.1093/toxsci/kfr339.

Loghman-Adham, M., Kiu Weber, C. I., Ciorciaro, C., Mann, J., and Meier, M. (2012). Detection and management of nephrotoxicity during drug development. *Expert Opin. Drug Saf* 11(4), 581-596. doi: 10.1517/14740338.2012.691964.

Lohr, J. W., Willsky, G. R., and Acara, M. A. (1998). Renal drug metabolism. *Pharmacol. Rev.* 50(1), 107-141.

Melenhorst, W. B. W. H., Mulder, G. M., Xi, Q., Hoenderop, J. G. J., Kimura, K., Eguchi, S., and van Goor, H. (2008). Epidermal Growth Factor Receptor Signaling in the Kidney. *Hypertension* 52, 987-993.

Meran, S., and Steadman, R. (2011). Fibroblasts and myofibroblasts in renal fibrosis. *Int. J. Exp. Pathol.* 92(3), 158-167. doi: 10.1111/j.1365-2613.2011.00764.x.

Moll, S., Ebeling, M., Weibel, F., Farina, A., Araujo Del Rosario, A., Hoflack, J. C., et al. (2013). Epithelial cells as active player in fibrosis: findings from an in vitro model. PLoS One 8(2), e56575.

Mulay, S. R., Evan, A., and Anders, H.-J. (2014). Molecular mechanisms of crystal-related kidney inflammation and injury. Implications for cholesterol embolism, crystalline nephropathies and kidney stone disease. *Nephrol. Dial. Transplant.* 29:507-514.

Murphy, K., Dorfman, S., Bauwens, L., Sohn, G., Smith, N., Leigh-Lancaster, C., Law, R. J., and McDonald, T. (2015). Devices, systems, and methods for the fabrication of tissue. U.S. Patent Application Publication No. 2015/0057786.

Murphy, K., Khatiwala, C., Dorfman, S., Shepherd, B., Presnell, S., Robbins, J. (2013). Engineered tissues for in vitro research uses, arrays thereof, and methods of making the same. U.S. Patent Application Publication No. 2013/0190210A1.

Nadasdy, T., Laszik, Z., Blick, K. E., Johnson, L. D., and Silva, F. G. (1994). Proliferative activity of intrinsic cell populations in the normal human kidney. *J. Am. Soc. Nephrol.* 4(12), 2032-2039.

Nagle, M. A., Truong, D. M., Dnyanmote, A. V., Ahn, S. Y., Eraly, S. A., Wu, W., et al. (2011). Analysis of three-dimensional systems for developing and mature kidneys clarifies the role of OAT1 and OAT3 in antiviral handling. *J. Biol. Chem.* 286(1), 243-251. doi: 10.1074/jbc.M110.139949.

Nguyen, D. L. G., King, S. M., and Presnell, S. C. (2016). Engineered renal tissues, arrays thereof, and methods of making the same. U.S. Patent Application Publication No. 2016/0097039.

Norotte, C., Marga, F. S., Niklason, L. E., and Forgacs, G. (2009). Scaffold-free vascular tissue engineering using bioprinting. *Biomaterials* 30(30), 5910-5917. doi: 10.1016/j.biomaterials.2009.06.034.

Okada, H., Kikuta, T., Kobayashi, T., Inoue, T., Kanno, Y., Takigawa, M., Sugaya, T., Kopp, J. B., and Suzuki, H. (2005). Connective tissue growth factor expressed in tubular epithelium plays a pivotal role in renal fibrogenesis. *J. Am. Soc. Nephrol.* 16(1), 133-143.

Okada, H., Kikuta, T., Inoue, T., Kanno, Y., Ban, S., Sugaya, T., Takigawa, M., and Suzuki, H. (2006). Dexamethasone induces connective tissue growth factor expression in renal tubular epithelial cells in a mouse strain-specific manner. *Am. J. Pathol.* 168(3), 737-747.

Ozbolat, I. T., and Hospodiuk, M. (2016). Current advances and future perspectives in extrusion-based bioprinting. *Biomaterials* 76, 321-343. doi: 10.1016/j.biomaterials.2015.10.076.

Paulsson, M. (1992). Basement membrane proteins: structure, assembly, and cellular interactions. *Crit. Rev. Biochem. Mol. Biol.* 27(1-2), 93-127. doi: 10.3109/10409239209082560.

Prasad, B., and Unadkat, J. D. (2014). Optimized approaches for quantification of drug transporters in tissues and cells by MRM proteomics. *AAPS J.* 16, 634-648.

Rahman, M., Shad, F., and Smith, M. C. (2012). Acute kidney injury: a guide to diagnosis and management. *Am. Fam. Physician* 86(7), 631-639.

Rampersad, S. N., (2012). Multiple applications of alamar blue as an indicator of metabolic function and cellular health in cell viability bioassays. *Sensors* 12(9): 12347-12360. doi: 10.3390/s120912347.

Redfern, W. S. (2010). Impact and frequency of different toxicities throughout the pharmaceutical life cycle. *The Toxicologist* 114(S1).

Schulz, W. W., Hagler, H. K., Buja, L. M., and Erdos, E. G. (1988). Ultrastructural localization of angiotensin I-converting enzyme (EC 3.4.15.1) and neutral metalloendopeptidase (EC 3.4.24.11) in the proximal tubule of the human kidney. *Lab. Invest.* 59(6), 789-797.

Sonomura, K., Okigaki, M., Taikou, K., Matsuoka, E., Shiotsu, Y., Adachi, T., Kado, H., Ishida, R., Kusaba, T., Matsubara, H., and Mori, Y. (2012). The kinase Pyk2 is involved in renal fibrosis by means of mechanical stretch-induced growth factor expression in renal tubules. *Kidney Int.* 81, 449-457.

Stokman, G., Stroo, I., Claessen, N., Teske, G. J. D., Weening, J. J., Leemans, J. C., and Florquin, S. (2010). Stem cell factor expression after renal ischemia promotes tubular epithelial survival. *PLoS ONE* 5(12), e14386.

Subramanian, B., Rudym, D., Cannizzaro, C., Perrone, R., Zhou, J., and Kaplan, D. L. (2010). Tissue-engineered three-dimensional in vitro models for normal and diseased kidney. *Tissue Eng. Part A* 16(9), 2821-2831. doi: 10.1089/ten.TEA.2009.0595.

Tang, J. and Zhuang, S. (2015). Epigenetics in acute kidney injury. *Curr. Opin. Nephrol. Hypertens.* 24(4):351-358.

Taniyama, Y., Sato, K., Sugawara, A., Uruno, A., Ikeda, Y., Kudo, M., Ito, S., and Takeuchi, K. (2001). Renal tubule-specific transcription and chromosomal localization of rat thiazide-sensitive Na—Cl transporter gene. *J. Biol. Chem.* 276, 26260-26268.

Tasnim, F., and Zink, D. (2012). Cross talk between primary human renal tubular cells and endothelial cells in cocultures. *Am. J. Physiol. Renal Physiol.* 302(8), F1055-1062. doi: 10.1152/ajprenal.00621.2011.

Tay, L. K., Bregman, C. L., Masters, B. A., and Williams, P. D. (1988). Effects of cis-diamminedichloroplatinum(II) on rabbit kidney in vivo and on rabbit renal proximal tubule cells in culture. *Cancer Res.* 48(9), 2538-2543.

Tran, T. T., Mittal, A., Gales, T., Maleeff, B., Aldinger, T., Polli, J. W., et al. (2004). Exact kinetic analysis of passive transport across a polarized confluent MDCK cell monolayer modeled as a single barrier. *J. Pharm. Sci.* 93(8), 2108-2123. doi: 10.1002/jps.20105.

Tsuboi, N., Yoshikai, Y., Matsuo, S., Kikuchi, T., Iwami, K. I., Nagai, Y., Takeuchi, O., Akira, S., and Matseguchi, T. (2002). Roles of toll-like receptors in C—C chemokine production by renal tubular epithelial cells. *J. Immunology* 169, 2026-2033.

Ussing, H. H., Erlij, D., and Lassen, U. (1974). Transport pathways in biological membranes. *Annu. Rev. Physiol.* 36, 17-49. doi: 10.1146/annurev.ph.36.030174.000313.

Vaidya, V. S., Ferguson, M. A., and Bonventre, J. V. (2008). Biomarkers of acute kidney injury. *Annu. Rev. Pharmacol. Toxicol.* 48, 463-493. doi: 10.1146/annurev.pharmtox.48.113006.094615.

Vesey, D. A., Qi, W., Chen, X., Pollock, C. A., and Johnson, D. W. (2009). Isolation and primary culture of human proximal tubule cells. *Methods Mol. Biol.* 466, 19-24. doi: 10.1007/978-1-59745-352-3_2.

Wang, W.-M., Zhang, H.-D., Jin, Y.-M., Zhu, B.-B., and Chen, N. (2009). PPAR-γ agonists inhibit TGF-β1 induced chemokine expression in human tubular epithelial cells. *Acta Pharmacol. Sin.* 30(1): 107-112.

Weng, Z., Patel, A. B., Panagiotidou, S., and Theoharides, T. C. (2015). The novel flavone tetramethoxyluteolin is a potent inhibitor of human mast cells. *J. Allergy Clin. Immunol.* 135(4), 1044-1052.e5. doi:10.1016/j.jaci.2014.10.032.

Wieser, M., Stadler, G., Jennings, P., Streubel, B., Pfaller, W., Ambros, P., et al. (2008). hTERT alone immortalizes epithelial cells of renal proximal tubules without changing their functional characteristics. *Am. J. Physiol. Renal Physiol.* 295(5), F1365-1375. doi: 10.1152/ajprenal.90405.2008.

Yonezawa, A., Masuda, S., Nishihara, K., Yano, I., Katsura, T., and Inui, K. (2005). Association between tubular toxicity of cisplatin and expression of organic cation transporter rOCT2 (Slc22a2) in the rat. *Biochem. Pharmacol.* 70(12), 1823-1831. doi: 10.1016/j.bcp.2005.09.020.

Zeisberg, M., and Kalluri, R. (2015). Physiology of the renal interstitium. *Clin. J. Am. Soc. Nephrol.* 10(10), 1831-1840. doi: 10.2215/CJN.00640114.

Zhang, J., and Zhou, W. (2012). Ameliorative effects of SLC22A2 gene polymorphism 808 G/T and cimetidine on cisplatin-induced nephrotoxicity in Chinese cancer patients. *Food. Chem. Toxicol.* 50(7), 2289-2293. doi: 10.1016/j.fct.2012.03.077.

Zoja, C., Morigi, M., and Remuzzi, G. (2003). Proteinuria and Phenotypic Change of Proximal Tubular Cells. *J. Am. Soc. Nephrol.* 14: S36-S41.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

All patents, patent applications and publications cited herein are fully incorporated by reference herein.

What is claimed is:

1. A model of a renal disorder, comprising a three-dimensional, engineered, bioprinted, biological renal tubule model comprising:
   (a) a layer of renal interstitial tissue, the renal interstitial tissue comprising renal fibroblasts and endothelial cells; and
   (b) a layer of renal epithelial tissue, the renal epithelial tissue comprising renal tubular epithelial cells, to form the three-dimensional, engineered, biological renal tubule model;
   provided that the renal interstitial tissue comprises an interstitial bio-ink, and the renal epithelial tissue comprises an epithelial bio-ink,
   wherein the model comprises a phenotype characteristic of a renal disorder in a renal tubule,
   wherein the phenotype is induced by contacting the renal tubule model with a toxin, a potential toxic agent, an antimicrobial agent, a metal, or an environmental agent, and
   wherein the fibroblasts and endothelial cells are present in a ratio at which the renal tubule model is planar six days post-printing and prior to the contacting.

2. The model of claim 1, wherein the renal tubular epithelial cells are polarized.

3. The model of claim 1, wherein the layer of renal interstitial tissue possesses an apical and basolateral surface.

4. The model of claim 1, wherein the renal tubule model further comprises a layer of basement membrane between the renal interstitial tissue layer and the renal epithelial tissue layer.

5. The model of claim 4, wherein the layer of renal epithelial tissue is in continuous contact with the layer of basement membrane and wherein the layer of basement membrane is in continuous contact with the layer of renal interstitial tissue.

6. The model of claim 1, wherein the layer of renal epithelial tissue comprises a monolayer over 80% or more of its surface area.

7. The model of claim 1, wherein the renal tubular epithelial cells are the only cells present in the layer of renal epithelial tissue and/or the fibroblasts and endothelial cells are the only cells present in the layer of renal interstitial tissue.

8. The model of claim 1, wherein the fibroblasts and endothelial cells are present in the layer of renal interstitial tissue at a ratio of about 50:50 fibroblasts to endothelial cells.

9. The model of claim 1, wherein the layer of renal interstitial tissue or layer of renal epithelial tissue is between 70%-100% living cells by volume.

10. The model of claim 1, wherein the renal tubule model further comprises a biocompatible membrane.

11. The model of claim 1, wherein the renal tubule model is at least two cell layers thick.

12. The model of claim 1, wherein a plurality of the renal tubule models are configured to form an array.

13. The model of claim 12, wherein the array is present in the wells of a microtiter plate.

14. The model of claim 1, wherein the phenotype includes at least one of contraction, curling, expansion, necrosis, apoptosis, tubular regeneration, compensatory proliferation, epithelial-mesenchymal transition, inflammation, ischemia, ischemia/reperfusion, reactive oxygen species, changes in the mitochondria, changes to cell morphology, changes to nuclear morphology, hyperproliferation, alterations in gene expression, secretion of biomarkers, epigenetic modifications, crystal deposition, cyst formation, a change to a cellular function, angiogenesis, hypoxia, extracellular matrix deposition, or death of surrounding tissue.

* * * * *